US007332311B2

(12) United States Patent
Lardizabal et al.

(10) Patent No.: US 7,332,311 B2
(45) Date of Patent: Feb. 19, 2008

(54) FATTY ACYL-COA: FATTY ALCOHOL ACYLTRANSFERASES

(75) Inventors: Kathryn D. Lardizabal, Woodland, CA (US); James G. Metz, Longmont, CO (US); Michael W. Lassner, Foster City, CA (US)

(73) Assignee: Calgene LLC, Davis, CA (US)

( * ) Notice: Subject to any disclaimer, the term of this patent is extended or adjusted under 35 U.S.C. 154(b) by 633 days.

(21) Appl. No.: 10/418,146

(22) Filed: Apr. 18, 2003

(65) Prior Publication Data

US 2003/0228668 A1 Dec. 11, 2003

Related U.S. Application Data

(63) Continuation of application No. 09/454,685, filed on Dec. 3, 1999, now abandoned, which is a continuation-in-part of application No. 09/205,815, filed on Dec. 4, 1998, now Pat. No. 6,492,509, which is a continuation-in-part of application No. 09/092,562, filed on Jun. 5, 1998, now Pat. No. 6,596,538, and a continuation of application No. 08/265,047, filed on Jun. 23, 1994, now Pat. No. 5,679,881.

(60) Provisional application No. 60/048,651, filed on Jun. 5, 1997.

(51) Int. Cl.
| | |
|---|---|
| C12P 7/64 | (2006.01) |
| C12P 21/06 | (2006.01) |
| C12N 9/10 | (2006.01) |
| C12N 9/12 | (2006.01) |
| C12N 5/10 | (2006.01) |
| C12N 5/14 | (2006.01) |
| C12N 1/21 | (2006.01) |
| C07K 14/00 | (2006.01) |

(52) U.S. Cl. ............... 435/134; 435/69.1; 435/325; 435/252.3; 435/410; 435/191; 435/193; 536/23.2; 536/23.6; 530/350

(58) Field of Classification Search ............... 435/134, 435/69.1, 325, 252.3, 410, 191, 193; 536/23.2, 536/23.6; 530/350
See application file for complete search history.

(56) References Cited

U.S. PATENT DOCUMENTS

| | | |
|---|---|---|
| 5,370,996 A | 12/1994 | Metz et al. |
| 5,403,918 A | 4/1995 | Metz |
| 5,411,879 A | 5/1995 | Pollard et al. |
| 5,420,034 A | 5/1995 | Kridl et al. |
| 5,445,947 A | 8/1995 | Metz et al. |
| 5,679,881 A | 10/1997 | Lardizabal et al. |
| 5,723,747 A | 3/1998 | Lassner et al. |
| 5,728,412 A | 3/1998 | Fujii et al. |

FOREIGN PATENT DOCUMENTS

| | | |
|---|---|---|
| WO | WO9116421 | 10/1991 |
| WO | WO9214816 | 9/1992 |
| WO | WO9310241 | 5/1993 |
| WO | WO9515387 | 6/1995 |
| WO | WO9533055 | 12/1995 |
| WO | WO9855632 | 12/1998 |

OTHER PUBLICATIONS

Seffernick et al., J. Bacteriol. 183(8):2405-2410, 2001.*
Witkowski et al., Biochemistry 38:11643-11650, 1999.*
Branden et al., Introduction to Protein Structure, Garland Publishing Inc., New York, p. 247, 1991.*
Abstract: National Plant Lipid Cooperative—*Plant Lipid Symposium* 1993, Minneapolis, Minnesota.
Andersson et al., "Purification of Diacylglycerol: Acyltransferase from Rat Liver to Near Homogeneity", *Journal of Lipid Research*, 35(3):535-545 (1994).
Bork, "Go Hunting in Sequence Databases but Watch Out for the Traps", *TIG*, 12(10):425-427(1996).
Bork, P., "Powers and Pitfalls in Sequence Analysis: The 70% Hurdle", *Genome Research*, 10:398-400 (2000).
Brenner, S., "Errors in Genome Annotation", *TIG*, 15(4):132-133 (1999).
Broun et al., "Catalytic Plasticity of Fatty Acid Modification Enzymes Underlying Chemical Diversity of Plant Lipids", *Science*, 282:1315-1317 (1998).
Canevascini et al., "Tissue-Specific Expression and Promoter Analysis of the Tobacco *ltp* 1 Gene" *Plant Physiology*, 112:513-524 (1996).
Chopra et al., "Metabolic Engineering of Plant Lipids", *Journal of Plant Biochemistry and Biotechnology*, 5(2):63-68 (1996).
Doerks, "Protein Annotation: Detective Work for Function Prediction", *TIG* 14(6):248-250 (1998).
Feng et al., "Abstract: F16P7-T7 IGF *Arabidopsis thaliana* Genomic Clone F19P7", *EMBL Sequence Accession No. B09476* (May 15, 1997).
Garver et al., "Abstract: Partial Purification Characterization of Acyl-CoA: Alcohol Transacylase in Subcellular Organelles from Developing Jojoba Cotyledons (*Simmondsia chinensis*)" (1991), Ph.D. Thesis from New Mexico State University.

(Continued)

*Primary Examiner*—Delia M. Ramirez
(74) *Attorney, Agent, or Firm*—Chunping Li; Arnold & Porter LLP

(57) ABSTRACT

By this invention, nucleic acid sequences encoding for fatty acyl-CoA:fatty alcohol acyltransferase (wax synthase) are provided, wherein said wax synthase is active in the formation of a wax ester from fatty alcohol and fatty acyl-CoA substrates. Of special interest are nucleic acid sequences obtainable from a jojoba embryo wax synthase having an apparent molecular mass of approximately 33 kD. Also considered are amino acid and nucleic acid sequences obtainable from wax synthase proteins and the use of such sequences to provide transgenic host cells capable of producing wax esters.

13 Claims, 6 Drawing Sheets

OTHER PUBLICATIONS

Garver et al., "A High Performance Liquid Chromatography-Based Radiometric Assay for Acyl-CoA: Alcohol Transacylase from Jojoba", *Analytical Biochemistry*, 207:335-340 (1992).

Hamilton et al., "A Monocot Pollen-Specific Promoter Contains Separable Pollen-Specific and Quantitative Elements", *Plant Molecular Biology*, 38:663-669 (1998).

International Search Report, PCT/US99/28678 (1999).

International Search Report, PCT/US98/11590 (1998).

Kamisaka et al., "Activation of Detergent-Solubilized Diacylglycerol Acyltransferase by Anionic Phospholipids", *Journal of Biochemistry*, 119:523-530 (1996).

Kamisaka et al., "Characterization of the Diacylglycerol Acyltransferase Activity in the Membrane Fraction from a Fungus", *Lipids*, 28(7):583-587 (1993).

Kamisaka et al., "Characterization of the Diacylglycerol Acyltransferase Activity in the Lipid Body Fraction from an Oleaginous Fungus", *Journal of Biochemistry*, 116:1295-1301 (1994).

Kamisaka et al., "Purification and Characterization of Diacylglycerol Acyltransferase from the Lipid Body Fraction of an Oleaginous Fungus", *Journal of Biochemistry*, 121:1107-1114 (1997).

Klein et al., "Transformation of Microbes, Plants and Animals by Particle Bombardment", *Bio/Technology*, 10:286-291 (1992).

Kwanyuen et al., "Isolation and Purification of Diacylglycerol Acyltransferase from Germinating Soybean Cotyledons", *Biochimica et Biophysica Acta*, 877:238-245 (1986).

Kwanyuen et al., "Subunit and amino acid composition of diacylglycerol acyltransferase from germinating soybean cotyledons", *Biochimica et biophysica acta*, 1039:67-72 (1990).

Lardizabal et al., "Purification of a Jojoba Embryo Wax Synthase, Cloning of its cDNA, and Production of High Levels of Wax in Seeds of Transgenic *Arabidopsis*", *Plant Physiology*, 122:645-655 (2000).

Lassner et al., "A Jojoba β-Ketoacyl-CoA Synthase cDNA Complements the Canola Fatty Acid Elongation Mutation in Transgenic Plants", *The Plant Cell*, 8:281-292 (1996).

Li et al., "*Arabidopsis* Rho-related GTPases: Differential Gene Expression in Pollen and Polar Localization in Fission Yeast", *Plant Physiology*, 118:407-417 (1998).

Metz et al., "Purification of a Jojoba Embryo Fatty Acyl-Coenzyme a Reductase and Expression of its cDNA in High Erucic Acid Rapeseed" *Plant Physiology*, 122:635-644 (2000).

Nakamura et al., "*Arabidopsis thaliana* Genomic DNA Chromosome 5, P1 Clone MTE17", EMBL Sequence Database, Jun. 19, 1998.

Nakamura et al., GenBank Accession No. AB015479, Jun. 17, 1998.

Ohlrogge et al., "Studies on Biosynthesis of Waxes on Developing Jojoba Seed Tissue", *Lipids*, 13(3):203-210 (1978).

Pollard et al., "Studies on Biosynthesis of Waxes by Developing Jojoba Seed II. The Demonstration of Wax Biosynthesis by Cell-Free Homogenates" *Lipids*, 14(7):651-662 (1979).

Polokoff et al., "Solubilization, Partial Purification and Characterization of Rat Liver Microsomal Diacylglycerol Acyltransferase", *Biochimica et Biophysica Acta*, 618:129-142 (1980).

Pushnik et al., Abstract: The Southwest Consortium Fourth Annual Meeting, Feb. 7, 1989.

Routaboul et al., "The *TAG1* Locus of *Arabidopsis* Encodes for a Diacylglycerol Acyltransferase", *Plant Physiol Biochem.*, 37(11):831-40 (1999).

Shockey et al., "Abstract: Identification and Characterization of Lipid Biosynthetic Enzymes in Developing Seed of Jojoba (*Simmondsia chinensis*, Link) (Liquid Wax)" (1996) Ph.D. Thesis from New Mexico State University.

Shockey et al., Photoaffinity Labeling of Developing Jojoba Seed Microsomal Membranes with a Photoreactive Analog of Acyl-Coenzyme A (Acyl-CoA), *Plant Physiol*, 107:155-160 (1995).

Smith et al., "The Challenges of Genome Sequence Annotation of 'The Devil is in the Details'", *Nature Biotechnology* 15:1222-1223 (1997).

Smith et al., "Obesity Resistance and Multiple Mechanisms of Triglyceride Synthesis in Mice Lacking Dgat", *Nature*, 25(1):87-90 (2000).

Van de Loo et al., "An oleate 12-hydroxylase from *Ricinus cummunis* L. is a fatty acyl desaturase homolog", *Proc. Natl. Acad. Sci. USA*, 92:6743-6747 (1995).

Venter et al., "The Sequence of the Human Genome", *Science*, 291:1304-1351 (2001).

Wildner et al., Abstract: The Southwest Consortium Fifth Annual Meeting, Apr. 22-24, 1990, Las Cruces, New Mexico.

Woese et al., "Conservation of Primary Structure in 16S Ribosomal RNA",*Nature* 254:83-85 (1975).

Wu et al.,"Studies of Biosynthesis of Waxes by Developing Jojoba Seed: III, Biosynthesis of Wax Esters from Acyl-CoA and Long Chain Alcohols", *Lipids*, 16(12):897-902 (1981).

Zou et al., "The *Arabidopsis thaliana TAG1* Mutant has a Mutation in a Diacylglycerol Acyltransferase Gene", *The Plant Journal*, 19(6):645-53 (1999).

Nakamura et al., "Structural Analysis of *Arabidopsis thaliana* Chromosome 5. VII. Sequence Features of the Regions of 1,013,767 bp Covered by Sixteen Physically Assigned P1 and TAC Clones", *DNA Research*, 5:297-308 (1998).

\* cited by examiner

| STRAIN ID | %FAME | | STRAIN ID | %FAME |
|---|---|---|---|---|
| 9708-01 | 34.5% | | 9712-30 | 31.1% |
| 9708-03 | 33.5% | | 9712-18 | 30.6% |
| 9708-04 | 34.1% | | 9712-16 | 31.1% |
| 9708-05 | 35.1% | | 9712-24 | 31.5% |
| 9708-06 | 36.1% | | 9712-22 | 31.5% |
| 9708-07 | 27.3% | | 9712-26 | 31.8% |
| 9708-08 | 34.1% | | 9712-20 | 32.6% |
| 9708-09 | 28.9% | | 9712-17 | 32.7% |
| 9708-10 | 34.3% | | 9712-28 | 33.6% |
| 9708-11 | 31.4% | | 9712-33 | 34.1% |
| 9708-12 | 31.0% | | 9712-29 | 34.1% |
| 9708-13 | 29.6% | | 9712-07 | 34.2% |
| 9708-14 | 30.0% | | 9712-10 | 34.2% |
| 9708-15 | 32.9% | | 9712-23 | 34.2% |
| 9708-16 | 31.3% | | 9712-06 | 34.6% |
| 9708-17 | 26.8% | | 9712-32 | 35.4% |
| 9708-18 | 36.2% | | 9712-05 | 35.4% |
| 9708-19 | 28.7% | | 9712-19 | 35.8% |
| 9708-20 | 29.6% | | 9712-27 | 36.0% |
| 9708-20 | 29.8% | | 9712-31 | 36.1% |
| 9708-21 | 34.4% | | 9712-21 | 36.3% |
| 9708-23 | 24.9% | | 9712-04 | 37.1% |
| 9708-24 | 27.1% | | 9712-34 | 37.1% |
| 9708-26 | 29.5% | | 9712-02 | 37.3% |
| 9708-27 | 34.3% | | 9712-25 | 37.4% |
| | | | 9712-08 | 37.8% |
| | | | 9712-15 | 38.0% |
| | | | 9712-03 | 38.3% |
| | | | 9712-11 | 38.8% |
| Control | 34.8% | | 9712-12 | 38.9% |
| Control | 35.4% | | 9712-14 | 41.8% |

FIGURE 6

FATTY ACYL-COA: FATTY ALCOHOL ACYLTRANSFERASES

CROSS-REFERENCE TO RELATED APPLICATIONS

This application is a continuation of U.S. patent application Ser. No. 09/454,685, filed Dec. 3, 1999, now abandoned which is a continuation-in-part of U.S. patent application Ser. No. 09/205,815, filed Dec. 4, 1998, now U.S. Pat. No. 6,492,509 which is a continuation-in-part of U.S. patent application Ser. No. 09/092,562, filed Jun. 5, 1998, now U.S. Pat. No. 6,596,538 which claims the benefit of U.S. Patent Application No. 60/048,651, filed Jun. 5, 1997, and which is a continuation of U.S. patent application Ser. No. 08/265,047, filed Jun. 23, 1994, now U.S. Pat. No. 5,679,881. U.S. patent application Ser. No. 09/454,685, filed Dec. 3, 1999 is herein incorporated by reference in its entirety.

INCORPORATION OF SEQUENCE LISTING

A paper copy of the Sequence Listing and a computer readable form of the sequence listing on diskette, containing the file named 16518105SEQLIST.txt, which is 46,576 bytes in size (measured in MS-DOS), and which was created on Friday, Mar. 21, 2003.

TECHNICAL FIELD

The present invention is directed to enzymes, methods to purify, and obtain such enzymes, amino acid and nucleic acid sequences related thereto, and methods of use for such compositions in genetic engineering applications.

INTRODUCTION

Background

Through the development of plant genetic engineering techniques, it is possible to transform and regenerate a variety of plant species to provide plants which have novel and desirable characteristics. One area of interest for such plant genetic engineering techniques is the production of valuable products in plant tissues. Such applications require the use of various DNA constructs and nucleic acid sequences for use in transformation events to generate plants which produce the desired product. For example, plant functional promoters are required for appropriate expression of gene sequences, such expression being either in the whole plant or in selected plant tissues. In addition, selective marker sequences are often used to identify the transformed plant material. Such plant promoters and selectable markers provide valuable tools which are useful in obtaining the novel plants.

A desirable goal which involves such genetic engineering techniques, is the ability to provide crop plants having a convenient source of wax esters. Wax esters are required in a variety of industrial applications, including pharmaceuticals, cosmetics, detergents, plastics, and lubricants. Such products, especially long chain wax esters have previously been available from the sperm whale, an endangered species, or more recently, from the desert shrub, jojoba. Neither of these sources provides a convenient supply of wax esters. Thus, in order to obtain a reliable source of such compounds, transformation of crop plants, which are easily manipulated in terms of growth, harvest and extraction of products, is desirable.

In order to obtain such transformed plants, however, the genes responsible for the biosynthesis of the desired wax ester products must first be obtained. Wax ester production results from the action of at least two enzymatic activities, fatty acyl reductase and fatty acyl:fatty alcohol acyltransferase, or wax synthase. In addition, a β-ketoacyl-Coenzyme A synthase may also be involved in wax biosynthesis by providing very long chain fatty acyl-CoA substrates for the reductase and wax synthase enzymatic reaction. Preliminary studies with such enzymes and extensive analysis and purification of a fatty acyl reductase, indicate that these proteins are associated with membranes, however the enzyme responsible for the fatty acyl:fatty alcohol ligation reaction in wax biosynthesis has not been well characterized. Thus, further study and ultimately, purification of this enzyme is needed so that the gene sequences which encode the enzymatic activity may be obtained.

It is desirable, therefore, to devise a purification protocol whereby the wax synthase protein may be obtained and the amino acid sequence determined and/or antibodies specific for the wax synthase obtained. In this manner, library screening, polymerase chain reaction (PCR) or immunological techniques may be used to identify clones expressing a wax synthase protein. Clones obtained in this manner can be analyzed so that the nucleic acid sequences corresponding to wax synthase activity are identified. The wax synthase nucleic acid sequences may then be utilized in conjunction with fatty acyl reductase proteins, either native to the transgenic host cells or supplied by recombinant techniques, for production of wax esters in host cells.

SUMMARY OF THE INVENTION

By this invention, nucleic acid sequences encoding fatty acyl-CoA:fatty alcohol O-acyltransferase protein (fatty alcohol acyltransferase, E.C.2.3.1.75), are provided, wherein said protein is active in the formation of wax esters from fatty alcohol and fatty acyl substrates. This fatty acyl-CoA:fatty alcohol O-acyltransferase is also referred to herein as "wax synthase". The wax synthase of this invention may be active with a variety of fatty acyl and fatty alcohol substrates, including acyl-CoAs and acyl-ACPs. The carbon chain length of these substrates may vary, although a given wax synthase may show preference for acyl and alcohol substrates having a specific chain length or may be active with acyl and alcohol substrates having a wide range with respect to carbon chain length. The wax synthases are preferably obtained from plant sources.

Preferably, the wax synthase of this invention has activity towards at least those acyl and alcohol substrates having a chain length of from 8 to 30 carbons, more preferably from 8 to 28 carbons. In addition, having obtained the wax synthase protein of this invention, further manipulations are now possible as described in further detail below. These manipulations may lead to production or discovery of other related wax synthases.

Thus, the present invention is directed to fatty acyl-CoA: fatty alcohol O-acyltransferase (also referred to herein as wax synthase), and in particular to wax synthase polynucleotides. The polynucleotides of the present invention include those derived from plant sources.

One aspect of the present invention relates to oligonucleotides which include partial or complete wax synthase encoding sequences.

It is also an aspect of the present invention to provide recombinant DNA constructs which can be used for transcription or transcription and translation (expression) of wax synthase. In particular, constructs are provided which are capable of transcription or transcription and translation in host cells. Particularly preferred constructs are those capable of transcription or transcription and translation in plant cells.

In another aspect of the present invention, methods are provided for production of wax synthase in a host cell or progeny thereof. In particular, host cells are transformed or transfected with a DNA construct which can be used for transcription or transcription and translation of wax synthase. The recombinant cells which contain wax synthase are also part of the present invention.

In a further aspect, the present invention relates to methods of producing a wax ester in a host cell or progeny thereof. In particular, host cells are transformed or transfected with a DNA construct which can be used for transcription or transcription and translation of wax synthase in a host cell having fatty alcohol and fatty acid substrates. The wax ester so produced find use in a variety of applications including pharmaceuticals, cosmetics, detergents, plastics, food applications and lubricants. In particular, the wax esters can be used in food applications as a low calorie fat.

In addition, the wax esters can be used as sources for the production of fatty alcohols and fatty acyl products. The wax esters can be subjected to hydrolysis conditions to produce fatty alcohols and fatty acyl products for use in a variety of applications, including, detergents, lubricants, corrosion inhibition, plasticiers, cosmetics, emulsifiers, and for use in pharmaceutical compositions.

In yet a further aspect of the present invention, methods of using polynucleotide and polypeptide sequences of the present invention to alter the oil content of a host cell are provided. In particular the methods involve growing a host cell having a recombinant nucleic acid construct comprising a promoter and a nucleic acid sequence which encodes an acyltransferase active in the formation of a wax ester. Such methods can be used in the production of host cells with modified oil/protein ratios.

The modified plants, seeds and oils obtained by the expression or suppression of the wax synthase proteins are also considered part of the invention.

BRIEF DESCRIPTION OF THE DRAWINGS

FIG. 6 provides the results of fatty acid methyl ester (FAME) analysis for oils obtained from *Arabidopsis* plants transformed with ATWS1 (SEQ ID NO: 3)(lines 9708) and ATWS2 (SEQ ID NO: 5)(lines 9712).

DETAILED DESCRIPTION OF THE INVENTION

Figure 1:
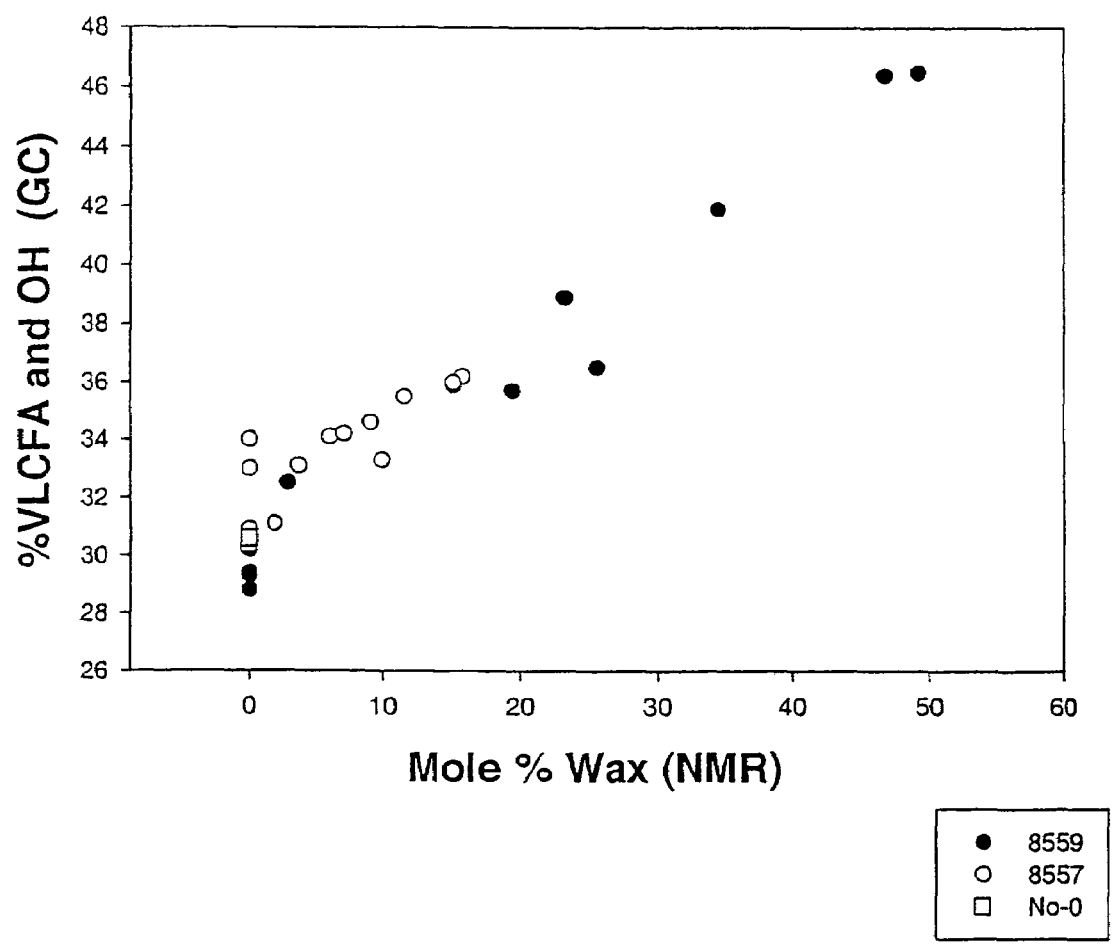
FIG. 1 A calculation of the contribution of wax synthase to the production of very long chain fatty acids (VLCFAs).

In accordance with the subject invention, nucleic acid sequences are provided which encode for amino acids, such as a protein, polypeptide or peptide fragment, which are active in catalyzing the esterification of a fatty alcohol by a fatty acyl group to produce a wax ester. Such proteins are known as fatty acyl-CoA:fatty alcohol acyltransferase (E.C.2.3.1.75). The acyl-CoA:alcohol acyltransferase of this invention is also referred to hereafter as "wax synthase".

Although typically referred to as an acyl-CoA:alcohol acyltransferase, the wax synthases of this invention may demonstrate activity towards a variety of acyl substrates, including fatty acyl-CoA and fatty acyl-ACP molecules. In addition, both the acyl and alcohol substrates acted upon by the wax synthase may have varying carbon chain lengths and degrees of saturation, although the wax synthase may demonstrate preferential activity towards certain molecules.

Many different organisms produce wax esters from alcohol and acyl substrates and are desirable sources of a wax synthase protein of this invention. For example, plants produce epidermal, or cuticular wax (Kolattukudy (1980) in *The Biochemistry of Plants* (Stumpf, P. K. and Conn, E. E., eds.) Vol. 4, p. 571-645), and the desert shrub, jojoba (Ohlrogge et al. (*Lipids* (1978) 13:203-210), as well as *Murraya koenigii* (Kartha, (1969) *Chemistry and Industry* 4:1342-1343 and Kartha, et al. (1972) *Chemistry and Industry* 891-892), produce a seed storage wax. Wax synthesis has also been observed in various species of bacteria, such as *Acinetobacter* (Fixter et al. (1986) *J. Gen. Microbiol.* 132: 3147-3157) and *Micrococcus* (Lloyd (1987) *Microbios* 52:29-37), and by the unicellular orgnanism, *Euglena* (Khan and Kolattukudy (1975) *Arch. Biochem. Biophys.* 170:400-408). In addition, wax production and wax synthase activity have been reported in microsomal preparations from bovine meibomian glands (Kolattukudy et al. (1986) *J. Lipid Res.* 27:404-411), avian uropygial glands, and various insect and marine organisms. Consequently, many different wax esters which will have various properties may be produced by the wax synthases of this invention, and the activity of the enzyme and type of wax ester produced may depend upon the available substrate or the substrate specificity of the particular wax synthase of interest.

To obtain a reliable source of a wax synthase protein for use in esterification reactions, it is desirable to isolate nucleic acid sequences associated with the wax synthase such that these sequences may be cloned into host cells for the production of the wax synthase enzyme. For example, one may clone nucleic acid sequences encoding a wax synthase protein into vectors for expression in *E. coli* cells to provide a ready source of the wax synthase protein. The wax synthase protein so produced may also be used to raise antibodies against wax synthase proteins for use in identification and purification of related wax synthase proteins from various sources, especially from plants. In addition, further study of the wax synthase protein may lead to site-specific mutagenesis reactions to further characterize and improve its catalytic properties or to alter its fatty alcohol or fatty acyl substrate specificity. A wax synthase with altered substrate specificity may find application in conjunction with other FAS enzymes.

Prior to the instant invention, nucleic acid and amino acid sequences of wax synthase proteins were not known. Thus, in order to obtain the nucleic acid sequences associated with wax synthase, it was necessary to first purify the protein from an available source and determine at least partial amino acid sequence so that appropriate probes useful for isolation of wax synthase nucleic acid sequences could be prepared.

The desert shrub, *Simmondsia chinensis* (jojoba) was identified as a source of a candidate wax synthase protein. Initial studies reveal that the jojoba wax synthase is an integral membrane protein and hydrophobic in nature. In general, membrane associated proteins are difficult to purify as they tend to lose enzymatic activity when they are solubilized, i.e. separated from the membrane environment in which they normally function. Techniques that have been used to solubilize integral membrane proteins include addition of detergents or organic solvents to a preparation of a suitable membrane fraction. Further conventional purification techniques, such as precipitation, ion-exchange, gel-filtration and affinity chromatography may then be utilized, assuming the desired protein still retains functional activity that can be measured using a specific enzymatic assay.

Typically, as a first step towards obtaining a solubilized membrane protein, a microsomal membrane preparation which comprises wax synthase activity is desired. Standard microsomal membrane preparations utilize differential centrifugation of a cell-free homogenate (CFH) to yield a membrane fraction which is free of whole cells, nuclei and soluble protein. (See, for example Mooré et al. (1987) *Biological Membranes: A Practical Approach*, pp. 37-72, eds. Finalay and Evans.) With oilseeds, initial centrifugation steps typically yield a pellet, supernatant and a floating fat pad, and microsomal membranes may then be recovered by further centrifugation of the supernatant.

A protocol is described in U.S. Pat. No. 5,403,918, whereby a jojoba membrane fraction was obtained with good recovery of enzyme activity associated with fatty acylreductase, another enzyme involved in the formation of wax esters in jojoba. The method also provides membrane fractions having wax synthase activity as described in detail in the examples which follow. In addition, microsomal membrane preparations from jojoba are also described in Lassner et al. (supra). Other procedures are known to those in the art and may be utilized to obtain similar membrane preparations. In addition, methods to assay for wax synthase activity in such preparations are described in Example 1.

A critical stage for further enzyme characterization and purification is that of obtaining solubilized wax synthase protein that is separated from its native lipid bilayer membrane environment, but retains substantial amounts of measurable wax synthase enzymatic activity. The removal of integral membrane proteins from the lipid bilayer is typically accomplished using amphiphilic detergents in aqueous solution, although organic solvents have also been used in a few cases. Many different detergents and methods of solubilization of membrane proteins are known to those skilled in the art, and are also reviewed by Neugebauer (*Methods Enzymol.* (1990) 182:239-253) and Hjelmiland (*Methods Enzymol.* (1990) 182:253-264).

Often, detergents which are used to solubilize membrane proteins are found to inhibit the enzymatic activity of a desired protein. Several detergents were tested for solubilization of jojoba wax synthase, including CHAPS (3-[(3-cholamidopropyl)-dimethyl-ammonio]-1-propane-sulfonate), which was demonstrated in U.S. Pat. No. 5,403,918 to be useful in purification of a fatty acyl reductase from jojoba. All were found to inhibit wax synthase enzymatic activity. Although strong inhibition by CHAPS was observed at concentrations above the CMC, it was found that addition of phospholipids, such as L-phosphatidyl choline, and adjustment of the CHAPS concentration from 1.0% to 0.2%, i.e. to below the CMC, results in reconstitution of a portion of the wax synthase activity. The primary requirement for reconstitution of wax synthase activity is the presence of phospholipids during the removal or dilution of the detergent, so that the wax synthase protein is incorporated into phospholipid vesicles. This differs from the protocol developed for reconstitution of jojoba reductase activity, which does not require addition of phospholipids. Thus, if phospholipids are present in a wax synthase preparation, such as that from a microsomal membrane fraction, activity may be detected simply by removal or dilution of detergent. However, in further purified wax synthase preparations, phospholipids must be added to detect activity. Optimum activity recovery is obtained when a ratio of CHAPS to PL is 2.8/1 (w/w) in the assay. A method to reconstitute and assay wax synthase activity in solubilized wax synthase preparations is described in Example 1.

Having obtained solubilized wax synthase protein, it can be seen that further experiments to characterize the enzyme as to substrate specificity, cofactor requirements and possible activity inhibiting agents may now be conducted. For example, it has been found that the jojoba wax synthase of this invention has a broad range of acyl substrates, including acyl-ACP and acyl-CoA molecules. In addition, the acyl and fatty alcohol substrates may have a broad size range with respect to carbon chain length. For example, activity was tested using substrates having carbon chain lengths of from C12 to C24, and all were shown to be utilized by the enzyme. In addition, activity was shown with fatty acyl and fattyalcohols having varying degrees of unsaturation.

Chromatography techniques may be utilized to provide enriched preparations of plant wax synthase. One such purification step involves chromatography over an immobilized reactive dye matrix, such as the Cibacron Blue F3GA (Blue A) used in this invention. The jojoba wax synthase activity binds to such a column when loaded in a buffer containing approximately 0.3M NaCl, while greater than approximately 85% of other protein passes through or is removed in subsequent washes. As described in U.S. Pat. No. 5,403,918, reductase activity is also bound to the Blue A column under such conditions. It is demonstrated herein that approximately 70% of the wax synthase activity loaded to a Blue A column can be recovered by elution with a 2.0M NaCl buffer wash. The jojoba reductase and β-ketoacyl-CoA synthase (KCS) proteins are also present in this Blue A eluate.

Further purification of the Blue A eluate is obtained by loading the sample onto a cyrstalline hydroxyapatite (HA) column. Wax synthase activity does not bind to the column and is found in the flow through and wash. The majority of the reductase and KCS activities bind to the column, as does the majority of the protein in the sample. The HA fraction enriched in wax synthase activity can be used for size exclusion chromatography, and using a Superdex 75 size exclusion column, the jojoba wax synthase protein is estimated to have a molecular weight of 48 kD.

Using such purification techniques, the jojoba wax synthase protein can be recovered as a substantially purified protein preparation and the amino acid sequence can be obtained. Similarly, due to the hydrophobic nature of the fatty alcohol substrates of wax synthase enzymes, other wax synthases would also be predicted to be associated with membranes in their native cells, and thus purification techniques described herein for jojoba wax synthase, may also be useful in recovery of purified preparation of other wax synthase proteins.

For example, *Euglena gracilis* produces waxes through the enzymatic actions of a fatty acyl-CoA reductase and a fatty acyl-CoA alcohol transacylase, or wax synthase. Typically, waxes having carbon chain lengths ranging from 24-32 are detected in this organism. As described above for jojoba, the *Euglena* wax synthase enzyme may be solubilized using a CHAPS/NaCl solution, and a partially purified wax synthase preparation is obtained by dye-ligand, HA and size exclusion chromatography.

*Acinetobacter* species are also known to produce wax ester compositions, although the mechanism is not well defined. As described herein a fatty acyl-CoA alcohol transacylase, or wax synthase activity is detected in *Acinetobacter* species. The wax synthase activity is solubilized in CHAPS/NaCl, enriched by Blue A column chromatography and may be further purified using such techniques as size exclusion chromatography.

In order to obtain nucleic acid sequences encoding the wax synthase of the present invention, the band containing the purified protein is cut out of an SDS gel to use in amino acid sequencing reactions. In gel digestion was used as opposed to more convenient methods, such as transfer of the protein to nitrocellulose or polyvinylidenedifluoride (PVDF) membranes due to the fact that conditions under which the jojoba wax synthase protein could be blotted and bound to such membranes have not been discovered. A commercial laboratory, W. M. Keck Foundation/Yale University, was provided with gel slices containing purified jojoba wax synthase protein for use in determining amino acid sequences of the jojoba protein by in-gel digest and subsequent protein sequencing. The peptide sequences generated in this manner may be used in PCR gene isolation techniques and cDNA library screening as described in more detail in the following examples.

Further experiments to confirm the identity of the wax synthase may also be desirable, such as expression of the protein in *E. coli*. The wax synthase may then act on fatty acyl and fatty alcohol substrates in such cells to produce wax esters which may be detected by various analytical methods. If the host cells do not contain the alcohol substrate of the wax synthase, activity may be verified by assaying cell extracts. Alternatively, wax synthase protein may be prepared by in vitro translation using wax synthase nucleic acid sequences and commercially available translation kits. Addition of microsomal membrane preparations to the in vitro translation sample may be necessary to obtain active wax synthase protein if membrane insertion is critical to activity. Other testing may include immunological assays, whereby antibodies specific for the candidate protein are prepared and found to inhibit wax synthase activity in protein preparations.

Thus, as described in more detail in the examples below, nucleic acid sequences are isolated using amino acid sequences determined for the proteins associated with wax synthase activity, both to confirm the identity of a wax synthase protein and to provide for transcription of the sequences and/or expression of the protein in host cells, either prokaryotic or eukaryotic.

As the wax synthase is a membrane bound protein, it may be desirable to express a candidate protein in a plant cell in order to verify the activity. Electroporation or bombardment of plant tissue for transient expression may be useful for this purpose. Ultimately, stable plant expression in a plant which produces substrates recognized by this enzyme is desired. If a plant targeted for transformation with wax synthase sequences does not naturally contain the fatty alcohol and fatty acyl ester substrates of this enzyme, a plant extract may be prepared and assayed for wax synthase activity by adding substrates of the wax synthase to the extract. Constructs and methods for transformation of plant hosts with wax synthase sequences are discussed in more detail below.

The wax synthase nucleic acids of this invention may be genomic or cDNA and may be isolated from cDNA or genomic libraries or directly from isolated plant DNA. As described in more detail in the examples below, a method for obtaining nucleic acid sequence for the jojoba wax synthase by PCR from primers specific for the disclosed jojoba wax synthase peptides is provided herein.

Wax synthase nucleic acid sequences of this invention include those corresponding to the jojoba wax synthase protein, as well as sequences obtainable from the jojoba protein or nucleic acid sequences. By "corresponding" is meant nucleic acid sequences, either DNA or RNA, including those which encode jojoba wax synthase protein or a portion thereof, regulatory sequences found 5' or 3' to said encoding sequences which direct the transcription or transcription and translation (expression) of the wax synthase in jojoba embryos, intron sequences not present in the cDNA, as well as sequences encoding any leader or signal peptide of a precursor wax synthase protein that may be required for insertion or retention into the endoplasmic reticulum membrane, which may or may not be found in the mature wax synthase enzyme.

By sequences "obtainable" from the jojoba sequence or protein, is intended any nucleic acid sequences associated with a desired wax synthase protein that may be synthesized from the jojoba wax synthase amino acid sequence, or alternatively identified in a different organism, and isolated using as probes jojoba wax synthase nucleic acid sequences or antibodies prepared against the jojoba wax synthase protein. In this manner, it can be seen that sequences of these other wax synthases may similarly be used to isolate nucleic acid sequences associated with wax synthase proteins from additional sources.

Thus, another aspect of the present invention relates to isolated wax synthase polynucleotides. The polynucleotide sequences of the present invention include isolated polynucleotides that encode the polypeptides of the invention having a deduced amino acid sequence selected from the group of sequences set forth in the Sequence Listing and to other polynucleotide sequences closely related to such sequences and variants thereof.

The invention provides a polynucleotide sequence identical over its entire length to each coding sequence as set forth in the Sequence Listing. The invention also provides the coding sequence for the mature polypeptide or a fragment thereof, as well as the coding sequence for the mature polypeptide or a fragment thereof in a reading frame with other coding sequences, such as those encoding a leader or secretory sequence, a pre-, pro-, or prepro-protein sequence. The polynucleotide can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

The invention also includes polynucleotides of the formula:

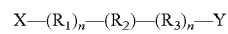

wherein, at the 5' end, X is hydrogen, and at the 3' end, Y is hydrogen or a metal, $R_1$ and $R_3$ are any nucleic acid residue, n is an integer between 1 and 3000, preferably between 1 and 1000 and $R_2$ is a nucleic acid sequence of the invention, particularly a nucleic acid sequence selected from the group set forth in the Sequence Listing and preferably SEQ ID NOs: 1,3,5,7,9,11,13,15, and 19 In the formula, $R_2$ is oriented so that its 5' end residue is at the left, bound to $R_1$, and its 3' end residue is at the right, bound to $R_3$. Any stretch of nucleic acid residues denoted by either R group, where R is greater than 1, may be either a heteropolymer or a homopolymer, preferably a heteropolymer.

The invention also relates to variants of the polynucleotides described herein that encode for variants of the polypeptides of the invention. Variants that are fragments of the polynucleotides of the invention can be used to synthesize full-length polynucleotides of the invention. Preferred embodiments are polynucleotides encoding polypeptide variants wherein 5 to 10, 1 to 5, 1 to 3, 2, 1 or no amino acid residues of a polypeptide sequence of the invention are substituted, added or deleted, in any combination. Particularly preferred are substitutions, additions, and deletions that are silent such that they do not alter the properties or activities of the polynucleotide or polypeptide.

Further preferred embodiments of the invention that are at least 50%, 60%, or 70% identical over their entire length to a polynucleotide encoding a polypeptide of the invention, and polynucleotides that are complementary to such polynucleotides. More preferable are polynucleotides that comprise a region that is at least 80% identical over its entire length to a polynucleotide encoding a polypeptide of the invention and polynucleotides that are complementary thereto. In this regard, polynucleotides at least 90% identical over their entire length are particularly preferred, those at least 95% identical are especially preferred. Further, those with at least 97% identity are highly preferred and those with at least 98% and 99% identity are particularly highly preferred, with those at least 99% being the most highly preferred.

Preferred embodiments are polynucleotides that encode polypeptides that retain substantially the same biological function or activity as the mature polypeptides encoded by the polynucleotides set forth in the Sequence Listing.

The invention further relates to polynucleotides that hybridize to the above-described sequences. In particular, the invention relates to polynucleotides that hybridize under stringent conditions to the above-described polynucleotides. As used herein, the terms "stringent conditions" and "stringent hybridization conditions" mean that hybridization will generally occur if there is at least 95% and preferably at least 97% identity between the sequences. An example of stringent hybridization conditions is overnight incubation at 42° C. in a solution comprising 50% formamide, 5×SSC (150 mM NaCl, 15 mM trisodium citrate), 50 mM sodium phosphate (pH 7.6), 5× Denhardt's solution, 10% dextran sulfate, and 20 micrograms/milliliter denatured, sheared salmon sperm DNA, followed by washing the hybridization support in 0.1×SSC at approximately 65° C. Other hybridization and wash conditions are well known and are exemplified in Sambrook, et al., Molecular Cloning: A Laboratory Manual, Second Edition, Cold Spring Harbor, N.Y. (1989), particularly Chapter 11.

The invention also provides a polynucleotide consisting essentially of a polynucleotide sequence obtainable by screening an appropriate library containing the complete gene for a polynucleotide sequence set for in the Sequence Listing under stringent hybridization conditions with a probe having the sequence of said polynucleotide sequence or a fragment thereof; and isolating said polynucleotide sequence. Fragments useful for obtaining such a polynucleotide include, for example, probes and primers as described herein.

As discussed herein regarding polynucleotide assays of the invention, for example, polynucleotides of the invention can be used as a hybridization probe for RNA, cDNA, or genomic DNA to isolate full length cDNAs or genomic clones encoding a polypeptide and to isolate cDNA or genomic clones of other genes that have a high sequence similarity to a polynucleotide set forth in the Sequence Listing. Such probes will generally comprise at least 15 bases. Preferably such probes will have at least 30 bases and can have at least 50 bases. Particularly preferred probes will have between 30 bases and 50 bases, inclusive.

The coding region of each gene that comprises or is comprised by a polynucleotide sequence set forth in the Sequence Listing may be isolated by screening using a DNA sequence provided in the Sequence Listing to synthesize an oligonucleotide probe. A labeled oligonucleotide having a sequence complementary to that of a gene of the invention is then used to screen a library of cDNA, genomic DNA or mRNA to identify members of the library which hybridize to the probe. For example, synthetic oligonucleotides can be prepared which correspond to the wax synthase EST sequences. The oligonucleotides can be used as primers in polymerase chain reaction (PCR) techniques to obtain 5' and 3' terminal sequence of wax synthase genes. Alternatively, where oligonucleotides of low degeneracy can be prepared from particular wax synthase peptides, such probes may be used directly to screen gene libraries for wax synthase gene sequences. In particular, screening of cDNA libraries in phage vectors is useful in such methods due to lower levels of background hybridization.

Typically, a wax synthase sequence obtainable from the use of nucleic acid probes will show 60-70% sequence identity between the target wax synthase sequence and the encoding sequence used as a probe. However, lengthy sequences with as little as 50-60% sequence identity can also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20-50% deviation (i.e., 50-80% sequence homology) from the sequences used as probe. Oligonucleotide probes can be considerably shorter than the entire nucleic acid sequence encoding a wax synthas enzyme, but should be at least about 10, preferably at least about 15, and more preferably at least about 20 nucleotides. A higher degree of sequence identity is desired when shorter regions are used as opposed to longer regions. It may thus be desirable to identify regions of highly conserved amino acid sequence to design oligonucleotide probes for detecting and recovering other related wax synthase genes. Shorter probes are often particularly useful for polymerase chain reactions (PCR), especially when highly conserved sequences can be identified. (See, Gould, et al., *PNAS USA* (1989) 86:1934-1938.).

Another aspect of the present invention relates to wax synthase polypeptides. Such polypeptides include isolated polypeptides set forth in the Sequence Listing, as well as polypeptides and fragments thereof, particularly those polypeptides which exhibit wax synthase activity and also those polypeptides which have at least 50%, 60% or 70% identity, preferably at least 80% identity, more preferably at least 90% identity, and most preferably at least 95% identity to a polypeptide sequence selected from the group of sequences set forth in the Sequence Listing, and also include portions of such polypeptides, wherein such portion of the polypeptide preferably includes at least 30 amino acids and more preferably includes at least 50 amino acids.

"Identity", as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" can be readily calculated by known methods including, but not limited to, those described in *Computational Molecular Biology*, Lesk, A. M., ed., Oxford University Press, New York (1988); *Biocomputing: Informatics and Genome Projects*, Smith, D. W., ed., Academic Press, New York, 1993; *Computer Analysis of Sequence Data, Part I*, Griffin, A. M. and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., Stockton Press, New York (1991); and Carillo, H., and Lipman, D., SIAM *J Applied Math*, 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., *Nucleic Acids Research* 12(1):387 (1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology*, 12: 76-80 (1994); Birren, et al., *Genome Analysis*, 1: 543-559 (1997)). The BLAST X program is publicly available from NCBI and other sources (*BLAST Manual*, Altschul, S., et al., NCBI NLM NIH, Bethesda, Md. 20894; Altschul, S., et al., *J. Mol. Biol.*, 215:403-410 (1990)). The well known Smith Waterman algorithm can also be used to determine identity.

Parameters for polypeptide sequence comparison typically include the following:

Algorithm: Needleman and Wunsch, *J. Mol. Biol.* 48:443-453 (1970)

Comparison matrix: BLOSSUM62 from Hentikoff and Hentikoff, *Proc. Natl. Acad. Sci USA* 89:10915-10919 (1992)

Gap Penalty: 12

Gap Length Penalty: 4

A program which can be used with these parameters is publicly available as the "gap" program from Genetics Computer Group, Madison Wis. The above parameters along with no penalty for end gap are the default parameters for peptide comparisons.

Parameters for polynucleotide sequence comparison include the following:

Algorithm: Needleman and Wunsch, J. Mol. Biol. 48:443-453 (1970)

Comparison matrix: matches=+10; mismatches=0

Gap Penalty: 50

Gap Length Penalty: 3

A program which can be used with these parameters is publicly available as the "gap" program from Genetics Computer Group, Madison Wis. The above parameters are the default parameters for nucleic acid comparisons.

The invention also includes polypeptides of the formula:

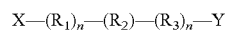

$$X—(R_1)_n—(R_2)—(R_3)_n—Y$$

wherein, at the amino terminus, X is hydrogen, and at the carboxyl terminus, Y is hydrogen or a metal, $R_1$ and $R_3$ are any amino acid residue, n is an integer between 1 and 1000, and $R_2$ is an amino acid sequence of the invention, particularly an amino acid sequence selected from the group set forth in the Sequence Listing and preferably SEQ ID NOs: 2, 4, 6, 8, 10, 12, 14, and 16. In the formula, $R_2$ is oriented so that its amino terminal residue is at the left, bound to $R_1$, and its carboxy terminal residue is at the right, bound to $R_3$. Any stretch of amino acid residues denoted by either R group, where R is greater than 1, may be either a heteropolymer or a homopolymer, preferably a heteropolymer.

Polypeptides of the present invention include isolated polypeptides encoded by a polynucleotide comprising a sequence selected from the group of a sequence contained in the Sequence Listing set forth herein.

The polypeptides of the present invention can be mature protein or can be part of a fusion protein.

Fragments and variants of the polypeptides are also considered to be a part of the invention. A fragment is a variant polypeptide which has an amino acid sequence that is entirely the same as part but not all of the amino acid sequence of the previously described polypeptides. The fragments can be "free-standing" or comprised within a larger polypeptide of which the fragment forms a part or a region, most preferably as a single continuous region. Preferred fragments are biologically active fragments which are those fragments that mediate activities of the polypeptides of the invention, including those with similar activity or improved activity or with a decreased activity. Also included are those fragments that antigenic or immunogenic in an animal, particularly a human.

Variants of the polypeptide also include polypeptides that vary from the sequences set forth in the Sequence Listing by conservative amino acid substitutions, substitution of a residue by another with like characteristics. In general, such substitutions are among Ala, Val, Leu and Ile; between Ser and Thr; between Asp and Glu; between Asn and Gln; between Lys and Arg; or between Phe and Tyr. Particularly preferred are variants in which 5 to 10; 1 to 5; 1 to 3 or one amino acid(s) are substituted, deleted, or added, in any combination.

Variants that are fragments of the polypeptides of the invention can be used to produce the corresponding full length polypeptide by peptide synthesis. Therefore, these variants can be used as intermediates for producing the full-length polypeptides of the invention.

The polynucleotides and polypeptides of the invention can be used, for example, in the transformation of host cells, such as plant host cells, as further discussed herein.

The invention also provides polynucleotides that encode a polypeptide that is a mature protein plus additional amino or carboxyl-terminal amino acids, or amino acids within the mature polypeptide (for example, when the mature form of the protein has more than one polypeptide chain). Such sequences can, for example, play a role in the processing of a protein from a precursor to a mature form, allow protein transport, shorten or lengthen protein half-life, or facilitate manipulation of the protein in assays or production. It is contemplated that cellular enzymes can be used to remove any additional amino acids from the mature protein.

A precursor protein, having the mature form of the polypeptide fused to one or more prosequences may be an inactive form of the polypeptide. The inactive precursors generally are activated when the prosequences are removed. Some or all of the prosequences may be removed prior to activation. Such precursor protein are generally called proproteins.

For immunological screening, antibodies to the jojoba wax synthase can be prepared by injecting rabbits or mice with the purified protein. Methods of preparing antibodies are well known to those in the art, and companies which specialize in antibody production are also available. Either monoclonal or polyclonal antibodies can be produced, although typically polyclonal antibodies are more useful for gene isolation.

To screen desired plant species, Western analysis is conducted to determine that a related protein is present in a crude extract of the desired plant species, that cross-reacts with the antibodies to the jojoba wax synthase. This is accomplished by immobilization of the plant extract proteins on a membrane, usually nitrocellulose, following electrophoresis, and incubation with the antibody. Many different systems for detection of the antibody/protein complex on the nitrocellulose filters are available, including radiolabeling of the antibody and second antibody/enzyme conjugate systems. Some of the available systems have been described by Oberfelder (*Focus* (1989) BRL/Life Technologies, Inc. 11:1-5). If initial experiments fail to detect a related protein, other detection systems and blocking agents may be utilized. When cross-reactivity is observed, genes encoding the related proteins can be isolated by screening expression libraries representing the desired plant species. Expression libraries can be constructed in a variety of commercially available vectors, including lambda gt11, as described in Maniatis, et al. (supra).

The clones identified as described above using DNA hybridization or immunological screening techniques are then purified and the DNA isolated and analyzed using known techniques. In this manner, it is verified that the clones encode a related wax synthase protein. Other wax synthases may be obtained through the use of the "new" wax synthase in the same manner as the jojoba wax synthase was used.

Alternatively, databases containing nucleic acid and amino acid sequences from various organisms may be searched with the sequences of the present invention to identify similar sequences. Surprisingly, using the jojoba wax synthase protein sequence to search a database containing DNA sequences from *Arabidopsis*, an approximately 12 Kb sequence containing at least seven repeats of an open reading frame with high similarity to the jojoba sequence are identified. The deduced amino acid sequences demonstrate a high level of homology to the jojoba wax synthase amino acid sequence. For example, amino acid sequence comparisons between jojoba wax synthase and the sequences obtained from the *Arabidopsis* homologues reveals an identity ranging from about 36% to about 44% between the amino acids. Thus, as shown herein, homologous similarity (identity+similarity) of at least 52% is shown in protein sequence comparisons between the jojoba and *Arabidopsis* sequences.

It will be recognized by one of ordinary skill in the art that wax synthase nucleic acid sequences of this invention may be modified using standard techniques of site specific mutation or PCR, or modification of the sequence may be accomplished in producing a synthetic nucleic acid sequence. These modified sequences are also considered wax synthase nucleic acid sequence of this invention. For example, wobble positions in codons may be changed such that the nucleic acid sequence encodes the same amino acid sequence, or alternatively, codons can be altered such that conservative amino acid substitutions result. In either case, the peptide or protein maintains the desired enzymatic activity and is thus considered part of the instant invention.

A nucleic acid sequence of a wax synthase enzyme of this invention may be a DNA or RNA sequence, derived from genomic DNA, cDNA, mRNA, or may be synthesized in whole or in part. The gene sequences may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene (that portion of the gene which encodes the wax synthase protein) may be synthesized using codons preferred by a selected host. Host-preferred codons may be determined, for example, from the codons used most frequently in the proteins expressed in a desired host species.

The nucleic acid sequences associated with wax synthase proteins will find many uses. For example, recombinant constructs can be prepared which can be used as probes or will provide for expression of the wax synthase protein in host cells. Depending upon the intended use, the constructs may contain the sequence which encodes the entire wax synthase, or a portion thereof. For example, critical regions of the wax synthase, such as an active site may be identified. Further constructs containing only a portion of the wax synthase sequence which encodes the amino acids necessary for a desired wax synthase activity may thus be prepared.

Useful systems for expression of the wax synthase sequences of this invention include prokaryotic cells, such as *E. coli*, yeast cells, and plant cells, both vascular and nonvascular plant cells being desired hosts. In this manner, the wax synthase protein may be produced to allow further studies, such as site-specific mutagenesis of encoding sequences to analyze the effects of specific mutations on reactive properties of the wax synthase protein.

The DNA sequence encoding a wax synthase of this invention may be combined with foreign DNA sequences in a variety of ways. By "foreign" DNA sequences is meant any DNA sequence which is not naturally found joined to the wax synthase sequence, including DNA sequences from the same organism which are not naturally found joined to wax synthase sequences. Both sense and antisense constructs utilizing wax synthase encoding sequences are considered, wherein sense sequence may be used for expression of wax synthase in a host cell, and antisense sequences may be used to decrease the endogenous levels of a homologous wax synthase protein naturally produced by a target organism. In addition, the wax synthase gene sequences of this invention may be employed in a foreign host in conjunction with all or part of the sequences normally associated with the wax synthase, such as regulatory or membrane targeting sequences.

In its component parts, a DNA sequence encoding wax synthase is combined in a recombinant construct having, in the 5' to 3' direction of transcription, a transcription initiation control region capable of promoting transcription and translation in a host cell, the nucleic acid sequence encoding wax synthase and a transcription termination region. Depending upon the host, the regulatory regions will vary, and may include regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli, B. subtilis, Sacchromyces cerevisiae*, including genes such as beta-galactosidase, T7 polymerase, tryptophan E and the like.

For the most part, the recombinant constructs will involve regulatory regions functional in plants which provide for expression of the wax synthase gene to produce functional wax synthase protein. The open reading frame, coding for the plant wax synthase or a functional fragment thereof will be joined at its 5' end to a transcription initiation regulatory region such as the wild-type sequence naturally found 5' upstream to the wax synthase structural gene. Numerous other promoter regions from native plant genes are available which provide for a wide variety of constitutive or regulatable expression of structural gene sequences.

In addition to sequences from native plant genes, other sequences can provide for constitutive gene expression in plants, such as regulatory regions associated with *Agrobacterium* genes, including regions associated with nopaline synthase (Nos), mannopine synthase (Mas), or octopine synthase (Ocs) genes. Also useful are regions which control expression of viral genes, such as the 35S and 19S regions of cauliflower mosaic virus (CaMV). The term constitutive as used herein does not necessarily indicate that a gene is expressed at the same level in all cell types, but that the gene is expressed in a wide range of cell types, although some variation in abundance is often detectable. Other useful transcriptional initiation regions preferentially provide for transcription in certain tissues or under certain growth conditions, such as those from napin, seed or leaf ACP, the small subunit of RUBISCO, and the like.

In embodiments wherein the expression of the wax synthase protein is desired in a plant host, the use of all or part of the complete plant wax synthase gene may be desired, namely the 5' upstream non-coding regions (promoter) together with the structural gene sequence and 3' downstream non-coding regions may be employed. If a different promoter is desired, such as a promoter native to the plant host of interest or a modified promoter, i.e., having transcription initiation regions derived from one gene source and translation initiation regions derived from a different gene source or enhanced promoters, such as double 35S CaMV promoters, the sequences may be joined together using standard techniques. Additionally, 5' untranslated regions from highly expressed plant genes may be useful to provide for increased expression of the wax synthase proteins described herein.

The DNA constructs which provide for wax synthase expression in plants may be employed with a wide variety of plant life, particularly, plants which produce the fatty acyl-CoA substrates of the wax synthase enzyme, such as *Brassica*. Other plants of interest produce desirable fatty acyl substrates, such as medium or long chain fatty acyl molecules, and include but are not limited to rapeseed (Canola varieties), sunflower, safflower, cotton, *Cuphea*, soybean, peanut, coconut and oil palms, and corn. Of particular interest is the use of such constructs in high erucic acid varieties of rapeseed *Brassica* (HEAR) for production of long-chain liquid waxes. Further uses envisioned for HEAR plants includes the production of varieties containing substantially increased levels of erucic acid as the result of providing an additional wax "sink" for the erucic acid, which is normally stored in the seed TAG.

As to the fatty alcohol substrate of the wax synthase enzyme, other than jojoba, seed plants are not known to produce large quantities of fatty alcohols, although small amounts of this substrate may be available to the wax synthase enzyme. Therefore, in conjunction with the wax synthase constructs of this invention, it is desirable to provide the target host cell with the capability to produce fatty alcohols from the fatty acyl molecules present in the host cells. For example, a plant fatty acyl reductase and methods to provide for expression of the reductase enzymes in plant cells are described in U.S. Pat. No. 5,370,996. The nucleic acid sequence and translated amino acid sequence of the jojoba reductase is provided in FIG. 1 of that patent. Thus, by providing both the wax synthase and reductase proteins to the host plant cell, wax esters may be produced from the fatty alcohol and fatty acyl substrates. Furthermore, expression of β-ketoacyl-CoA synthase in conjunction with expression of wax synthase and reductase proteins is considered in the present invention. In this manner, the production of very long chain fatty acid substrates of these enzymes may be increased in the target plant species.

In addition to the jojoba reductase, reductase enzymes from other organisms may be useful in conjunction with the wax synthases of this invention. Other potential sources of reductase enzymes include *Euglena, Acinetobacter, Micrococus*, certain insects and marine organisms, and specialized mammalian or avian tissues which are known to contain wax esters, such as bovine meibomian glands or ovian uropygial glands. Other potential sources of reductase proteins may be identified by their ability to produce fatty alcohols or, if wax synthase is also present, wax esters.

The wax synthase and reductase sequences may be provided during the same transformation event, or alternatively, two different transgenic plant lines, one having wax synthase constructs and the other having reductase constructs may be produced by transformation with the various constructs. These plant lines may then be crossed using known plant breeding techniques to provide wax synthase and reductase containing plants for production of wax ester products.

Furthermore, other nucleic acid sequences encoding for enzymes involved in the formation of very long chain fatty acids may also find use in the DNA constructs of the present invention for the production of wax esters in a plant host. Such nucleic acid sequences are known in the art and are as described in U.S. Pat. No. 5,679,881. For example, as described in the examples below, the wax synthase of the present invention is used in plant expression constructs in conjunction with nucleic acid sequences encoding for a fatty acid elongase (described in U.S. Pat. No. 5,679,881, the entirety of which is incorporated herein by reference) and an acyl-CoA reductase (described in U.S. Pat. No. 5,403,918, the entirety of which is incorporated herein by reference). Such plant expression constructs provide for the production of wax esters in transgenic *Arabidopsis thaliana* plants.

For applications leading to wax ester production, 5' upstream non-coding regions obtained from genes regulated during seed maturation are desired, especially those preferentially expressed in plant embryo tissue, such as regions derived from ACP, oleosin (Lee and Huang (1991) *Plant Physiol.* 96:1395-1397) and napin regulatory regions. Transcription initiation regions which provide for preferential expression in seed tissue, i.e., which are undetectable in other plant parts, are considered desirable for wax ester production in order to minimize any disruptive or adverse effects of the gene product in other plant parts. Further, the seeds of such plants may be harvested and the lipid reserves of these seeds recovered to provide a ready source of wax esters. Thus, a novel seed product may be produced in oilseed plants which, absent transformation with wax synthase constructs as described herein, are not known to produce wax esters as a component of their seed lipid reserves.

Such "seed-specific promoters" may be obtained and used in accordance with the teachings of U.S. Pat. No. 5,420,034, and U.S. Pat. No. 5,430,194. In addition, where plant genes, such as the jojoba reductase and wax synthases are expressed, it may be desirable to use the entire plant gene, including 5' and 3' regulatory regions and any introns that are present in the encoding sequence, for expression of the jojoba genes in a transformed plant species, such as *Arabidopsis* or *Brassica*.

Regulatory transcription termination regions may be provided in recombinant constructs of this invention as well. Transcription termination regions may be provided by the DNA sequence encoding the plant wax synthase or a convenient transcription termination region derived from a different gene source, especially the transcription termination region which is naturally associated with the transcription initiation region. The transcript termination region will contain at least about 0.5 kb, preferably about 1-3 kb of sequence 3' to the structural gene from which the termination region is derived.

Where expression of the wax synthase, as well as other genes involved in wax synthesis, is to be directed in other plant tissues, additional promoters may find use in the constructs of the present invention. For example, where preferential expression of the genes in the pollen is desired, promoter regions, for example, Rop1At (Li, et al. (1998) *Plant Phyiol.* 118:407-417) and others described by Hamilton, et al. (1998) *Plant Mol Biol.* 38(4)663-669 may be employed. Where preferential expression in the epidermis is desired, promoter regions such as Ntltp1 (Canevascini, et al. (1996) *Plant Physiol.* 112:513-524) may be employed.

Additional plant gene regions may be used to optimize expression of wax synthase and reductase genes in plant tissues. For example, 5' untranslated regions of highly expressed genes, such as that of the small subunit (SSU) of RuBP-carboxylase, inserted 5' to DNA encoding sequences may provide for enhanced translation efficiency. Portions of the SSU leader protein encoding region (such as that encoding the first 6 amino acids) may also be used in such constructs. In addition, for applications where targeting to plant plastid organelles is desirable, transit peptide encoding sequences from SSU or other nuclear-encoded chloroplast proteins may be used in conjunction with wax synthase and reductase sequences.

Depending on the method for introducing the DNA expression constructs into the host cell, other DNA sequences may be required. Importantly, this invention is applicable to dicotyledons and monocotyledons species alike and will be readily applicable to new and/or improved transformation and regeneration techniques.

In developing the recombinant construct, the various components of the construct or fragments thereof will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the recombinant construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Similarly, genes encoding enzymes providing for production of a compound identifiable by color change, such as GUS, or luminescence, such as luciferase are useful. Depending upon the number of different host species the expression construct or components thereof are introduced, one or more markers may be employed, where different conditions for selection are used for the different hosts.

In addition to the sequences providing for transcription of wax synthase sequences, the DNA constructs of this invention may also provide for expression of an additional gene or genes, whose protein product may act in conjunction with the wax synthase to produce a valuable end product. For example, as discussed above, DNA constructs which provide for expression of wax synthase and a fatty acyl reductase so that wax esters may produced in transformed hosts, are considered in this invention. The constructs may also provide for the expression of a third gene encoding, for example β-ketoacyl-CoA synthase (KCS). Furthermore, production of different wax esters having varying carbon chain lengths and degrees of saturation is desired and may be provided by transforming host plants having fatty alcohol or fatty acyl substrates of varying chain lengths. Such plants may be provided, for example, by methods described in the published international patent application number PCT WO 91/16421, which describes various thioesterase genes and methods of using such genes to produce fatty acyl substrates having varying chain lengths in transformed plant hosts.

Furthermore, to optimize the production of wax esters in oilseed plant hosts, one may wish to decrease the production of the triacylglyceride oils that are normally produced in the seeds of such plants. One method to accomplish this is to antisense a gene critical to this process, but not necessary for the production of wax esters. Such gene targets include diacylglycerol acyltransferase, and other enzymes which catalyse the synthesis of triacylglycerol. Additionally, it may be desirable to provide the oilseed plants with enzymes which may be used to degrade wax esters as a nutrient source, such as may be isolated from jojoba or various other wax producing organisms. In this manner, maximal production of wax esters in seed plant hosts may be achieved.

In addition, by engineering wax synthesis systems into plants which normally do not produce wax, it may be possible to increase the production of novel fatty acids. For example, there may be intrinsic limitations in oilseed triacylglyceride and phospholipid synthesis which prefer specific fatty acids for a given position on the glycerol backbone. Therefore, plants engineered to produce a given "exotic" fatty acid may be limited in the amount of that fatty acid produced due to the limitations of positions on the glycerol backbone. Thus, by introducing a wax synthesis system into a plant, it may be possible to increase the amount of an "exotic" fatty acid produced by providing an alternative fatty acid sink. Furthermore, it is also possible to increase the amount of an "exotic" fatty acid using a wax synthesis system derived from a source which accumulates wax esters which are composed of such fatty acids. For example, by utilizing a wax synthase from *Euglena*, it is possible to increase the amount of C12 fatty acids.

Furthermore, the introduction of a wax synthesis system into oil producing plants may allow for a further increase in the amount of oil produced as a component of the host cell. By expressing a wax synthesis system in an oil producing plant tissue, such as an oil seed, it is possible to further increase the amount of oil produced in such a tissue, by utilizing the native oil production, such as through triacylglycerol synthesis, and the introduced wax synthesis.

The wax esters produced in the methods described herein may be harvested using techniques for wax extraction from jojoba or by various production methods used to obtain oil products from various oilseed crops. The waxes thus obtained will find application in many industries, including pharmaceuticals, cosmetics, detergents, plastics, food applications and lubricants. Applications will vary depending on the chain length and degree of saturation of the wax ester components. For example, long chain waxes having a double bond in each of the carbon chains are liquid at room temperature, whereas waxes having saturated carbon chain components, may be solid at room temperature, especially if the saturated carbon chains are longer carbon chains.

The wax esters so produced can be used as a source for obtaining fatty alcohols for use in a variety of applications. Methods for the production of fatty alcohols from wax esters are known in the art, and are described for example by Duncan, et al. (1974) *J. Am. Oil Chem. Soc.* 51(12):534-536. Fatty alcohols find use in a variety of applications known to the skilled artisan, and include but are not limited to detergents, lubricants, corrosion inhibition, plasticiers, cosmetics, emulsifiers, and for use in pharmaceutical compositions. The fatty alcohols produced can be saturated or unsaturated, and preferably include short chain fatty alcohols, medium chain fatty alcohols and long chain fatty alcohols, most preferred are medium and long chain fatty alcohols, most especially preferred are long chain fatty alcohols.

Furthermore, production of transgenic plants which produce wax esters in the epidermal cell layer provides for enhanced tolerance to various environmental stresses, such as drought tolerance, as well as pathogen and insect tolerances. Such roles for epicuticular waxes are known in the art, and are reviewed, for example, by Post-Beittenmiller (1996) *Annu. Rev. Plant Physiol. Plant Mol. Biol.* 47:405-430 and Jeffree (1986) *Insects and the Plant Surface* (Southwood and Juniper, eds.) 23-64 (Edward Arnold).

The method of transformation is not critical to the instant invention; various methods of plant transformation are currently available. As newer methods are available to transform crops, they may be directly applied hereunder. For example, many plant species naturally susceptible to *Agrobacterium* infection may be successfully transformed via tripartite or binary vector methods of *Agrobacterium* mediated transformation. Other sequences useful in providing for transfer of nucleic acid sequences to host plant cells may be derived from plant pathogenic viruses or plant transposable elements. In addition, techniques of microinjection, DNA particle bombardment, electroporation have been developed which allow for the transformation of various monocot and dicot plant species.

The invention now being generally described, it will be more readily understood by reference to the following examples, which are included for purposes of illustration only and are not intended to limit the invention unless so stated.

EXAMPLES

Example 1

Wax Synthase Assays

Methods to assay for wax synthase activity in microsomal membrane preparations or solubilized protein preparations are described.

A. Radiolabeled Material

The substrate generally used in the wax synthase assays, [1-$^{14}$C]palmitoyl-CoA, is purchased from Amersham® (Arlington Heights, Ill.). Other chain length substrates were synthesized in order to perform chain length specification studies. Long chain [1-$^{14}$C]fatty acids (specific activity 51-56 Ci/mole), namely 11-cis-eicosenoic acid, 13-cis-docosenoic acid and 15-cis-tetracosenoic acid are prepared by the reaction of potassium [$^{14}$C]cyanide with the corresponding alcohol mesylate, followed by the base hydrolysis of the alcohol nitrile to the free fatty acid. The free fatty acids are converted to their methyl esters with ethereal diazomethane, and purified by preparative silver nitrate thin layer chromatography (TLC). The fatty acid methyl esters are hydrolyzed back to the free fatty acids. Radiochemical purity is assessed by three TLC methods: normal phase silica TLC, silver nitrate TLC, and C18 reversed phase TLC. Radiochemical purity as measured by these methods was 92-98%. Long chain [1-$^{14}$C]acyl-CoAs are prepared from the corresponding [1-$^{14}$C]free fatty acids by the method of Young and Lynen (*J. Bio. Chem.* (1969) 244:377), to a specific activity of 10 Ci/mole. [1-$^{14}$C]hexadecanal is prepared by the dichromate oxidation of [1-$^{14}$C]hexadecan-1-ol, according to a micro-scale modification of the method of Pletcher and Tate (*Tet. Lett.* (1978) 1601-1602). The product is purified by preparative silica TLC, and stored as a hexane solution at −70° C. until use.

B. Assay for Wax Synthase Activity in a Microsomal Membrane Preparation

Wax synthase activity in a microsomal membrane preparation is measured by incubation of 40 µM [1-$^{14}$C]acyl-CoA (usually palmitoyl-CoA, sp. act. 5.1-5.6 mCi/mmol) and 200 mM oleyl alcohol with the sample to be assayed in a total volume of 0.25 ml. The incubation mixture also contains either 25 mM HEPES (4-[2-hydroxyethyl]-1-piperazineethane-sulfonic acid), pH 7.5, as the buffering agent with 20% w/v glycerol, 1 mM DTT, 0.5M NaCl or 25 mM Tricine-NaOH, pH 7.8, as the buffering agent with 0.28M NaCl, 10% glycerol, and 2 mM β-mercaptoethanol. Initial studies were performed with the first buffer system, when the pH was chosen to accommodate the preference of the acyl-CoA reductase enzyme. Membrane preparations were later changed to the second buffer system to accommodate the higher pH optimum of wax synthase.

A substrate mixture is prepared in a glass vial, with oleyl alcohol being added immediately before use, and is added to samples. Incubation is carried out at 30° C. for up to one hour. The assay is terminated by placing the assay tube on ice and immediately adding 0.25 ml isopropanol:acetic acid (4:1 v/v). Unlabeled wax esters (0.1 mg) and oleyl alcohol (0.1 mg) are added as carriers. The [$^{14}$C] lipids are extracted by the scaled-down protocol of Hara and Radin (*Anal. Biochem.* (1978) 90:420). Two ml of hexane/isopropanol (3:2, v/v) is added to the terminated assay. The sample is vortexed, 1 ml of aqueous sodium sulphate solution (6.6% w/v) is added, and the sample is again vortexed.

C. Assay for Solubilized Wax Synthase Activity

Solubilized wax synthase is assayed using up to 50 µl sample in a 250 µl assay that contains 40 µM 1-$^{14}$C-16:0 CoA (5 Ci/mol), 200 µM 18:1-OH, 0.07% soybean phospholipid. (Sigma, P-3644), 0.2% CHAPS, 280 mM NaCl, 25 mM Tricine-NaOH, pH 7.8, 2 mM β-ME and 5.6% glycerol. Phospholipid (50 mg/ml in 0.5% CHAPS) is added directly to the sample, which is in 1% CHAPS, then diluted by a cocktail containing the remaining assay components. Reconstitution of activity is presumed to be based on the incorporation of wax synthase into the phospholipid vesicles. Wax synthase is sensitive to detergent and requires the amount of phospholipid (PL) and detergent (CHAPS) to be balanced at 2.8/1 (CHAPS/PL, w/w) in the assay for maximal activity. Assays for wax synthase activity in samples concentrated by ultra-filtration require a readjustment of the sample volume assayed because of the concentration of CHAPS. Introducing too much CHAPS into the assay results in inhibition of activity. If samples are concentrated by ultrafiltration, the optimum volume of sample to be assayed may be reestablished by performing a concentration curve of % CHAPS in the assay using a small amount of sample and assaying at a fixed concentration of phospholipid and sodium chloride. Wax synthase is less sensitive to changes in PL concentration than it is to changes in CHAPS concentration.

D. Analysis of Assay Products

For analyzing the products of either the microsomal membrane preparation wax synthase assay or the solubilized wax synthase assay, two protocols have been developed. One protocol, described below as "extensive assay" is more time-consuming, but yields more highly quantitative results. The other protocol, described below as "quick assay" also provides a measure of wax synthase activity, but is faster, more convenient and less quantitative.

1. Extensive Analysis: Following addition of the sodium sulphate and vortexing the sample, the upper organic phase is removed and the lower aqueous phase is washed with 4 ml hexane/isopropanol (7:2 v/v). The organic phases are pooled and evaporated to dryness under nitrogen. The lipid residue is resuspended in a small volume of hexane, and an aliquot is assayed for radioactivity by liquid scintillation counting. The remainder of the sample can be used for. TLC analysis of the labeled classes and thereby give a measure of total wax produced.

For lipid class analysis the sample is applied to a silica TLC plate, and the plate is developed in hexane/diethyl ether/acetic acid (80:20:1 or 70:30:2 v/v/v). The distribution of radioactivity between the lipid classes, largely wax esters, free fatty acids, fattyalcohols, and polar lipids at the origin, is measured using an AMBIS® radioanalytic imaging system (AMBIS® Systems Inc., San Diego, Calif.). If necessary the individual lipid classes can be recovered from the TLC plate for further analysis. Reversed-phase TLC systems using C18 plates developed in methanol have also been used for the analysis.

2. Quick Analysis: Following addition of the sodium sulfate and vortexing the sample, a known percentage of the organic phase is removed and counted via liquid scintillation counting. This calculation is used to estimate the total counts in the organic phase. Another portion of the organic phase is then removed, dryed down under nitrogen, redissolved in hexane and spotted on TLC plates and developed and scanned as described for the detailed assay. In this manner the percentage of the total counts which are incorporated into wax is determined.

Example 2

Further Studies to Characterize Wax Synthase Activity

A. Seed Development and Wax Synthase Activity Profiles

Embryo development was tracked over two summers on five plants in Davis, Calif. Embryo fresh and dry weights were found to increase at a fairly steady rate from about day 80 to about day 130. Lipid extractions reveal that when the embryo fresh weight reaches about 300 mg (about day 80), the ratio of lipid weight to dry weight reaches the maximum level of 50%.

Wax synthase activity was measured in developing embryos as described in Example 1B. As the jojoba seed coats were determined to be the source of an inhibiting factor(s), the seed coats were removed prior to freezing the embryos in liquid nitrogen for storage at −70° C.

Development profiles for wax synthase activities as measured in either a cell free homogenate or a membrane fraction, indicate a large induction in activity which peaks at approximately 110-115 days after anthesis. Embryos for enzymology studies were thus harvested between about 90 to 110 days postanthesis, a period when the wax synthase activity is high, lipid deposition has not reached maximum levels, and the seed coat is easily removed. The highest rate of increase of wax synthase activity is seen between days 80 and 90 postanthesis. Embryos for cDNA library construction were thus harvested between about 80 to 90 days postanthesis when presumably the rate of synthase of wax synthase protein would be maximal. Correspondingly, the level of mRNA encoding wax synthase would be presumed to be maximal at this stage.

B. Microsomal Membrane Preparation

Jojoba embryos are harvested at approximately 90-110 days after flowering, as estimated by measuring water content of the embryos (45-70%). The outer shells and seed coats are removed and the cotyledons quickly frozen in liquid nitrogen and stored at −70° C. for future use. For initial protein preparation, frozen embryos are powdered by pounding in a steel mortar and pestle at liquid nitrogen temperature. In a typical experiment, 70 g of embryos are processed.

The powder is added, at a ratio of 280 ml of solution per 70 g of embryos, to the following high salt solution: 3M NaCl, 0.3M sucrose, 100 mM HEPES, 2 mM DTT, and the protease inhibitors, 1 mM EDTA, 0.7 mg/ml leupeptin, 0.5 mg/ml pepstatin and 17 mg/ml PMSF. A cell free homogenate (CFH) is formed by dispersing the powdered embryos in the buffer with a tissue homogenizer (Kinematica, Switzerland; model PT10/35) for approximately 30 sec. and then filtering through three layers of Miracloth (CalBioChem, LaJolla, Calif.). The filtrate is centrifuged at 100,000×g for one hour.

The resulting sample consists of a pellet, supernatant and a floating fat pad. The fat pad is removed and the supernatant fraction is collected and dialyzed overnight (with three changes of the buffering solution) versus a solution containing 1M NaCl, 100 mM HEPES, 2 mM DTT and 0.5M EDTA. The dialyzate is centrifuged at 200,000×g for 1½ hour to yield a pellet, DP2. The pellet is suspended in 25 mM HEPES and 10% glycerol, at ¹⁄₂₀ of the original CFH volume, to yield the microsomal membrane preparation.

Activity is assayed as described in Example 1. Recovery of wax synthase activity is estimated at 34% of the original activity in the cell free homogenate. Wax synthase activity in this preparation is stable when stored at −70° C. ps C. Substrate Specificity Acyl-CoA and alcohol substrates having varying carbon chain lengths and degrees of unsaturation were added to microsomal membrane fractions prepared as described above to determine the range of substrates recognized by the jojoba wax synthase.

Acyl-CoA and alcohol substrates having varying carbon chain lengths and degrees of unsaturation were added to microsomal membrane fractions prepared as described in Example 3A to determine the range of substrates recognized by the jojoba wax synthase. Assays were performed as described in Example 1B using the Tricine buffer system with the following change, both acyl-CoA and alcohol concentrations were 40 µM instead of the 200 µM alcohol concentration normally used. Acyl-CoA's were prepared as 2.5 mM stocks (in 1.25 mM Na Acetate buffer pH 4.8 and 1.5% CHAPS) and 4 µl of these stocks were used in a 250 µl assay making the final CHAPS concentration 0.024%. Without the addition of detergent, the long-chain saturated acyl-CoA's would not dissolve in the buffer. Alcohols were prepared as 25 mM stocks in 2-methoxyethanol and 0.4 µl of the stock was used in a 250 µl assay. To evaluate the acyl-CoA specificity, 1-$^{14}$C-hexadecanol (10.3 mCi/mmol, Sigma 31,326-2) was used as substrate. The purchased 1-$^{14}$C-hexadecanol was only 62% pure and had to be further purified by thin layer chromatography prior to use. The product was spotted onto a glass silica gel TLC plate and migrated in hexane:diethyl ether:acetic acid (70:30:2). Unlabeled alcohol was spotted in outside lanes and used to identify the migration level of the radiolabeled product. The TLC plate was briefly exposed to iodine vapors to identify the location of the alcohol. The 1-$^{14}$C-hexadecanol spot was scraped from the TLC plate and transferred to a new vial. The product was eluted from the silica with hexane:isopropanol and the organic extract was filtered to remove silica. The filtered solvent was transferred to a new vial where the solvent was evaporated to dryness. The final product was resuspended in 2-methoxyethanol at a concentration of 0.15 µCi/µl. The final product appeared to be 100% pure by TLC in the solvent system above. The 1-$^{14}$C-16:0-CoA was as described in Example 1. Results of these experiments are presented in Table 1 below.

TABLE 1

| Structure | Acyl Group | pmol/min/mg Alcohol Group |
|---|---|---|
| 8:0 | 147.5 | 2656.3 |
| 10:0 | 197.8 | 2396.8 |
| 12:0 | 345.5 | 5663.4 |
| 14:0 | 1584.6 | 4919.1 |
| 16:0 | 1533.8 | 5250.6 |
| 18:0 | 1693.8 | 2557.9 |
| 20:0 | 1373.2 | 1666.4 |
| 22:0 | 1196.6 | 1555.9 |
| 24:0 | 1308.3 | 2582.0 |
| 18:1 9-c | 821.9 | 12623.8 |
| 18:1 9-t | nd | 12600.2 |
| 18:1 11-c | nd | 12147.6 |
| 18:1 11-t | nd | 13739.4 |
| 18:2 9-c, 12-c | 198.8 | 11344.2 |
| 18:3 9-2, 12-c, 15-c | 516.1 | nd |
| 20:1 11-c | 3880.1 | 6172.4 |
| 22:1 13-c | 916.8 | 2783.0 |
| 22:1 13-t | nd | 1862.0 |
| 24:1 15-c | 1794.0 | 1576.3 |

For comparison purposes it is desirable to evaluate acyl-CoA's and alcohol's at equivalent concentrations, however, in practicality there is an endogenous pool of alcohol present in jojoba microsomal fractions of unknown concentration. This pool dilutes the $^{14}$C labeled hexadecanol used to evaluate the acyl-CoA's rendering some of the waxes formed undetectable. The result is an underestimation of the specific activity for all of the acyl-CoA's relative to the specific activities of the alcohols.

The above results demonstrate that the jojoba wax synthase utilizes a broad range of fatty acyl-CoA and fatty alcohol substrates.

In addition, wax synthase activity towards various acyl-thioester substrates was similarly tested using palmitoyl-CoA, palmitoyl-ACP and N-acetyl-S-palmitoyl cysteamine as acyl substrates. The greatest activity was observed with the acyl-CoA substrate. Significant activity (~10% of that with acyl-CoA) was observed with acyl-ACP, but no activity was detectable with the N-acetyl-S-palmitoyl cysteamine substrate.

D. Effectors of Activity

Various sulphydryl agents were screened for their effect on wax synthase activity. Organomercurial compounds were shown to strongly inhibit activity. Iodoacetamide and N-ethylmaleamide were much less effective. Inhibition by para-hydroxymercuribenzoate was observed, but this inhibition could be reversed by subsequent addition of DTT. These results demonstrate that inhibition by para-hydroxymercuribenzoate involves blocking of an essential sulphydryl group.

Example 3

Purification of Jojoba Wax Synthase

Methods are described which may be used for isolation of a jojoba membrane preparation having wax synthase activity, solubilization of wax synthase activity, and further purification of the wax synthase protein.

A. Microsomal Membrane Preparation

The following modification of the method described in Example 2 is employed and provides an improved membrane fraction useful for purification of wax synthase from solubilized membranes.

Typically, 100 g of jojoba embryos are added to 400 ml of extraction buffer (40 mM Tricine-NaOH, pH 7.8, 200 mM KCl, 10 mM EDTA, 5 mM β-mercaptoethanol), ground in a blender, and homogenized with a Polytron tissue disrupter. All subsequent steps are performed at 4° C. The blended material is filtered through Miracloth (CalBioChem®). Centrifugation (20,000×g; 20 min.) of the filtrate yielded a floating wax layer, a turbid supernatant fraction and a dark green pellet. The supernatant fraction is collected and centrifuged (100,000×g; 2 h) to obtain membrane pellets which are then resuspended in 40 ml of Buffer A (25 mM Tricine-NaOH, pH 7.8, 200 mM KCl, 5 mM EDTA, 5 mM β-mercaptoethanol) containing 50% (w/v) sucrose. This homogenate is distributed into four SW28 centrifuge tubes (Beckman) and each is overlaid with 10 ml Buffer A containing 20% sucrose and then with 13 ml Buffer A. After centrifugation (28,000 rpm; 2 h), a membrane fraction is collected from the 20%/50% sucrose interface, diluted with four volumes Buffer A and collected by centrifugation (200,000×g; 1 h). The membranes are then homogenized in 10 ml storage buffer [25 mM Tricine-NaOH, pH 7.8, 1 M NaCl, 10% (w/v) glycerol, 5 mM β-mercaptoethanol)]. The protein concentration of membranes prepared via this protocol is typically between 7 and 9 mg/ml. Protein concentrations are estimated as described (Bradford, 1976) using BSA as the protein standard.

B. Solubilization of Wax Synthase Protein

The membrane suspension is adjusted to approximately 0.83 mg of protein per ml by dilution with storage buffer (25 mM Tricine-NaOH, pH 7.8, 1M NaCl, 10% glycerol, 5 mM β-mercaptoethanol). Solid 3-([3-cholamidopropyl]dimethyl-ammonio)-1-propanesulfate (CHAPS) is added to achieve a final concentration of 2% (w/v) and a detergent to protein ratio of 24:1. After incubation on ice for 1 hr, the sample is centrifuged (200,000 g for 1 hr), and the supernatant fraction collected.

C. Purification of Wax Synthase Activity

The 200,000 g supernatant fraction is diluted (with 0.57% CHAPS, 25 mM Tricine-NaOH, pH 7.8, 20% glycerol) to yield final concentrations of NaCl and CHAPS of 0.3M and 1%, respectively. The sample is loaded onto a Blue A-agarose (Amicon®, Inc., Beverly, Mass.) column that has been equilibrated with buffer B (25 mM Tricine-NaOH, pH 7.8, 1% CHAPS, 20% glycerol) containing 0.3M NaCl. After washing with equilibration buffer, wax synthase activity is eluted with buffer B containing 2M NaCl. Active fractions eluted from the Blue A column are pooled (Blue Pool) and used for further chromatography.

Two purification protocols were used for band identification and further purification of the wax synthase protein. In Protocol 1 (FIG. 1), the Blue Pool was concentrated 5.4 fold by ultrafiltration in a pressure cell fitted with a YM 30 membrane (Amicon®, Inc., Beverly, Mass.). One-half of the concentrate was applied to a Ceramic Hydroxyapatite (CHT) column (Bio-Scale® CHT-2; Bio-Rad®, Hercules, Calif.) Equilibrated in buffer B containing 2M NaCl. The column was washed with 6 column volumes of equilibration buffer and bound proteins were eluted with buffer B containing 0.1M dipotassium phosphate and 2M NaCl. After reequilibration of the CHT column, the second half of the Blue Pool concentrate was chromatographed in the same manner. In order to detect activity, wax synthase was assayed according to the protocol for samples concentrated by ultrafiltration. Wax synthase activity, measured on CHT-Run 1, was found in the flow through and wash. Protein profiles of the two CHT runs were identical so the CHT-run 2 was not assayed. Active fractions from the two CHT runs were pooled and concentrated 10 fold and applied to a Sephacryl® S100 HR column (2.5×90 cm) equilibrated in buffer B with 1.0 M NaCl. Protein and activity determinations were made and active fractions were selected from the retained portion of the run which maximized activity and minimized protein. The S100 pool (fractions 64-70) was applied to a crystalline hydroxylapatite (HA) column (Bio-Gel® HT; Bio-Rad®, Hercules, Calif., 1×19.3 cm) equilibrated in buffer B with 1 M NaCl. Again, the majority of the wax synthase activity was present in the flow through and wash. Bound proteins were eluted in buffer B with 0.1M dipotassium phosphate, and 1M NaCl. Fractions from the final HA run were examined by SDS-PAGE. A single protein migrating at 33 kD on SDS-PAGE was correlated with the presence of wax synthase activity.

Figure 2:
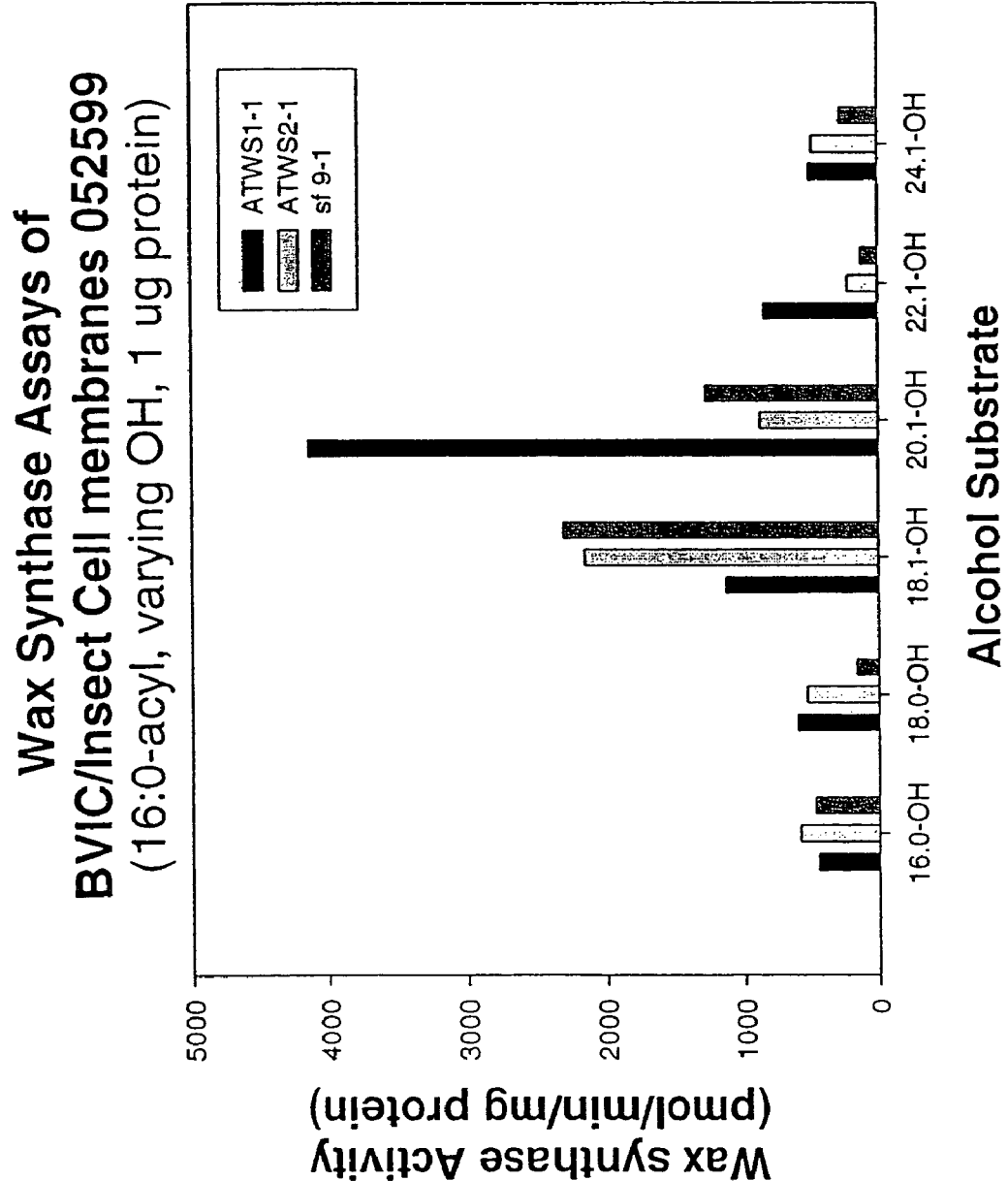
FIG. 2 Results of wax synthase activity assay using various alcohol substrates and 1 ug 16:0-CoA substrate.

In a second preparation (Protocol 2, FIG. 2) the Blue Pool was applied directly to a crystalline HA column (1×11.7 cm), equilibrated in buffer B with 1M NaCl, without concentration. Two fractions were selected for further purification by size exclusion chromatography on a Superdex® 75 HR 10/30 column (Bio-Rad®, Hercules, Calif.; sizing range:5000-75,000 daltons) equilibrated with 25 mM Tricine-NaOH, pH 7.8, 1% CHAPS, 20% glycerol, 1M NaCl. Wax synthase activity was measured according to the protocol described for solubilized samples in Example 1C. One fraction eluted early in the flow through of the HA column (fraction 31) and the other eluted in the wash (fraction 67). The protein profiles of the two fractions were different based on SDS-PAGE analysis. Both Superdex® 75 runs were examined by gradient SDS-PAGE and a protein of approximately 33 kD was identified that chromatographed with activity. A calibration curve was generated using molecular mass standards chromatographed under the same buffer and column conditions. Comparison of the elution volume of the peak of Wax Synthase activity to this standard curve yielded a value of 48 kDa for the molecular mass of the solubilized enzyme.

A chart representing the purification of wax synthase from Protocol 1 (Table 2) shows a 150 fold purification of the enzyme from the solubilized protein fraction.

TABLE 2

Purification of Jojoba Wax Synthase

| Purification Step | Enzyme Activity (nmol/min) | Yield % | Protein (mg) | Specific Activity (nmol/min/mg) | Purification (fold) |
|---|---|---|---|---|---|
| Solubilized Fraction | 274.4 | 100 | 415 | 0.7 | 1 |
| Blue A Agarose | 214.7 | 78.2 | 15 | 14.3 | 22 |
| Ceramic Hydroxyapatite | 176.6 | 64.3 | 6.4 | 27.6 | 42 |
| Sephacryl S-100 (sizing) | 41.3 | 15.1 | 1.2 | 33.1 | 50 |
| Hydroxyapatite (crystalline) | 18.8 | 6.9 | 0.2 | 99.2 | 150 |

D. SDS PAGE Analysis

Samples from the column fractions were diluted in SDS PAGE sample buffer (1×buffer=2% SDS, 250 mM β-mercaptoethanol, 0.0025% bromphenol blue) and analyzed by electrophoresis. Polyacrylamide gradient gel electrophoresis (10-13%) was carried out according to the method of Laemmli (*Nature* (1970) 227:680-685) with some of the modifications of Delepelaire (*Proc. Nat. Acad. Sci.* (1979) 76:111-115). Sodium dodecyl sulfate was used in the upper reservoir buffer at 0.1% but was ommitted from the lower reservoir buffer, stacking and resolving gels. The stacking gel contained 5% of a 30% acrylamide stock (29.2% acrylamide, 0.8% N,N'-bis-methyleneacrylamide, w/v), 0.06% ammonium persulfate (w/v) and 0.1% TEMED (v/v). The resolving gel contained a 10-13% linear gradient of acrylamide stock stabilized by a 0-10% linear gradient of sucrose. Electrophoresis was carried out at room temperature at 150V, constant voltage, for 9-10 hours. Proteins were visualized by staining with silver according to the method of Blum et al. (*Electrophoresis* (1987) 8:93-99 or with Coomassie Blue (0.1% Coomassie Blue R-250, 50% methanol, 10% acetic acid). The 33 kDa protein identified as wax synthase does not appear as a major component of the active fraction until purification through the hydroxyapatite column. Following purification Protocol 1 (Example 3C) the only protein that correlates with activity on the final column is one at 33 kDa.

Example 4

Preparation of Protein for In-Gel Digestion

A. Preparation of Samples for SDS-PAGE by Concentration

Odd numbered fractions from the flow through/wash of the final HA column (Protocol 1) were pooled and concentrated three fold by ultrafiltration in a pressure cell fitted with a YM 30 membrane (Amicon®, Inc., Beverly, Mass.). The sample was further concentrated using two Centricon-30 units (Amicon®, Inc., Beverly, Mass.) to volumes of approximately 50 µl. Each sample was treated with 6 µl SDS Cocktail (4 µl 20% SDS, 1 µl 14.3M β-metcaptoethanol, and 1 µl 0.1% Bromophenol Blue). After sitting at room temperature for 15 minutes, the samples were applied to a 10-13% acrylamide gradient gel (Example 3D) (16×16 cm×1 mm thick) and proteins were resolved by electrophoresis at 150V, constant voltage, for 9.5 hours. The gel was stained with 0.1% Coomassie Blue in 50% methanol, 10% acetic acid for 15 minutes then destained in 50% methanol, 10% acetic acid for 2×20 minutes. The 33 kD Wax Synthase band was excised from the gel and destained in 50% ethanol for 3×20 minutes. One lane contained a streak of protein and was not used in the final digestion.

B. Preparation of Samples for SDS-PAGE by Precipitation

Aliquots (0.8 ml) of the even numbered fractions from the final HA column (Protocol 1) were pooled in groups of three over the column profile. The pools were divided equally into three, 1.5 ml vials. Protein was precipitated by the addition of 0.2 ml 40% TCA. After 30 minutes on ice the samples were centrifuged (12,000×g, 15 minutes at 4 C) to pellet the precipitated protein. The supernatants were removed and the pellets washed twice with 0.6 ml ice cold acetone. The final three pellets for each pooled set of samples were resuspended with the same 50 µl of SDS sample buffer by transfering the buffer from one vial to the next. The emptied vials, that had already been resuspended, were washed with 10 µl of sample buffer for a total resuspended volume of 60 µl for each pooled sample. The samples were applied to a 12% acrylamide Tris/Glycine mini-gel (Novex®, San Diego, Calif.,1.5 mm×10 well) and proteins were resolved by electrophoresis at 150 V, constant voltage, for 20 minutes beyond the elution of dye from the foot of the gel. The gel was stained with Coomassie Blue and destained using Gel-Clear (Novex®, San Diego, Calif.). Wax Synthase was excised from three non-equivalent lanes on the gel representing the peak and tailing fractions from the column. The gel slices were placed in 1.5 ml vials and destained with 1 ml of 50% methanol, 10% acetic acid for 2 hours. The destain solution was removed and the gel slices were frozen in liquid nitrogen and sent on dry ice, overnight, to the W M Keck Foundation Biotechnology Resource Laboratory at Yale University for in-gel-digestion. One gel slice from the sample concentrated by ultrafiltration and three gel slices from the samples concentrated by precipitation were pooled for in-gel tryptic digestion.

Example 5

Determination of Amino Acid Sequence

Protein sequencing was performed at the W. M. Keck Foundation Biotechnology Resource Laboratory, Yale University. Procedures include amino acid analysis of a portion (10-15%) of the gel slice for quantitation and amino acid composition, digestion of the protein with one of the proteolytic enzymes (trypsin or lysyl endopeptidase), and fractionation of the products by reverse phase HPLC. Absorbance peaks are selected from the HPLC run and subjected to laser desorption mass spectrometry to determine the presence, amount, and mass of the peptide prior to protein sequencing. The longest peptides are selected for microsequencing.

Amino acid seqeunces of jojoba wax synthase peptides obtained by trypsin digestion are presented in Table 3 below using the one letter code.

TABLE 3

Amino Acid Sequence of Jojoba Wax Synthase Tryptic Peptides

| | | |
|---|---|---|
| WSpep29 | FVPAVAPHGGALR | (SEQ ID NO:20) |
| WSpep33 | TIDEYPVMFNYTQK | (SEQ ID NO:21) |

Example 6

Purification of Additional Wax Synthases and Reductases

A. Adaptation of jojoba wax synthase solubilization and purification methods to obtain partially purified preparations of wax synthase from other organisms are described.

*Acinetobacter*

Cells of *Acinetobacter calcoaceticus* strain BD413 (ATCC #33305) are grown on ECLB (*E. coli* luria broth), collected during the logarithmic growth phase and washed in a buffer containing either HEPES-NaOH, pH 7.5, or Tricine-NaOH pH 7.8, in 0.1M NaCl, 1 mM DTT and protease inhibitors. Washed cells were resuspended in fresh buffer and ruptured by passage through a French pressure cell (two passes at ~16,000p.s.i.). Unbroken cells are removed by centrifugation at 5000×g for 10 minutes, and membranes are collected by centrifugation at 100,000×g for 1 hour. The membrane pellet is homogenized in storage buffer (25 mM HEPES-NaOH, pH 7.5, or 25 mM Tricine-NaOH, pH 7.8, in 10% (w/v) glycerol, 100 mM NaCl). Wax synthase activity is detected in these membranes using assay conditions described for the jojoba enzyme in Example 1B, using [1-$^{14}$C] palmitoyl-CoA and 18:1 alcohol as the substrates.

Wax synthase activity is solubilized by incubation of the membranes with 2% CHAPS in the presence of 0.5M NaCl, at a detergent to protein ratio of 5:1. Solubilization of the activity is demonstrated by the detection of wax synthase enzyme activity in the supernatant fraction after centrifugation at 200,000 g for 1 hour and by size exclusion chromatography (i.e. the activity elutes from the column in the retained fractions as a symmetrical peak). The activity of the solubilized enzyme is detected by simple dilution of the CHAPS concentration to ~0.3% (i.e. to below its CMC). Incorporation of the enzyme into phospholipid vesicles is not required to detect solubilized activity.

For purification, the solubilized *Acinetobacter* wax synthase activity is subjected to chromatographic procedures similar to those described for the jojoba wax synthase. In one protocol, the soluble protein preparation is loaded to a Blue A agarose column under low salt conditions (100 mM NaCl in a column buffer containing 0.75% % CHAPS, 10% glycerol, 25 mM HEPES-NaOH, pH 7.5) and eluted from the column using 1.0M NaCl in the column buffer.

Size exclusion chromatography on Superose® 12 (Pharmacia®; Piscataway, N.J.) medium is used to obtain an estimate of the size of the native enzyme. Comparison to molecular mass standards chromatographed under identical conditions yields an apparent mass of ~40 kDa for the solubilized wax synthase.

In another protocol, solubilized protein is loaded onto a Blue A column equilibrated with 25 mM Tricine-NaOH, pH 7.8, 1% CHAPS, 20% glycerol containing 0.1M NaCl and eluted in the same buffer containing 1.0M NaCl. The eluted material is then loaded onto a hydroxyapatite column equilibrated with column buffer containing 1.0 M NaCl and unlike the jojoba wax synthase, the acinetobacter wax synthase activity binds the column and is eluted in a gradient of 1-100 mM dipotassium phosphate. When examined by SDS-PAGE, several protein candidates can be correlated with wax synthase activity.

*Euglena*

*Euglena gracilis*, strain Z (ATCC No. 12716) is grown heterotrophically in the dark (Tani et al. (1987) *Agric. Biol. Chem.* 51:225-230) at ~26° C. with moderate shaking. Cells are collected and washed in buffer containing 25 mM Bis-Tris-Propane, pH 7.0, 0.25M NaCl and 1 mM EDTA. Washed cells are resuspended in fresh buffer and ruptured by passage through a French pressure cell (two passes at ~16,000 p.s.i.). Unbroken cells, cell debris and nuclei are removed by centrifugation at 20,000×g for 20 minutes, and microsomal membranes are collected by centrifugation at 200,000×g for 1 hour. The membrane pellet is homogenized in storage buffer (25 mM Bis-Tris-Propane, pH 7.0, 0.25M NaCl, 10% (w/v) glycerol and 1 mM EDTA). Wax synthase activity is detected in these membranes using assay conditions as described for the jojoba enzyme. The radiolabelled substrate is the same as for the jojoba example (i.e. [1-$^{14}$C] palmitoyl-CoA), however, 16:0 rather than 18:1 is used as the alcohol acceptor, and Bis-Tris-Propane buffer at pH 7.0 is utilized.

The *Euglena* wax synthase activity is solubilized by incubation of the membranes with 2% CHAPS in the presence of 0.5M NaCl. Solubilization of the protein is demonstrated by the detection of enzyme activity in the supernatant fraction after centrifugation at 200,000×g for 1 hour. The activity of the solubilized enzyme is detected by dilution of the CHAPS concentration to ~0.3% (i.e. to below its CMC). It is not necessary to incorporate the enzyme into phospholipid vesicles as was the case for the solubilized jojoba wax synthase.

For partial purification, the solubilized *Euglena* wax synthase activity is subjected to chromatographic separation on Blue A agarose medium. The column is equilibrated with 0.1M NaCl in a column buffer containing; 25 mM Bis-Tris-Propane, pH 7.0, 20% (w/v) glycerol, 0.75% CHAPS and 1 mM EDTA. The sample containing solubilized wax synthase activity is diluted to 0.1M NaCl and loaded onto a 1×7 cm column (5.5 ml bed volume). The column is washed with equilibration buffer and subjected to a linear NaCl gradient (0.1M to 1.0M NaCl) in column buffer. Wax synthase activity is eluted as a broad peak in the last half of the salt gradient.

SDS-PAGE analysis of column fractions reveals that the polypeptide complexity of the activity eluted from the column is greatly reduced relative to the loaded material. A polypeptide with an apparent molecular mass of ~41 kD was observed to track with wax synthase activity in the column fractions. Further purification techniques, such as described for jojoba and *Acinetobacter* are conducted to verify the association of wax synthase activity with the ~41 kD peptide.

For further analysis of wax synthase activity in *Euglena*, size exclusion chromatography was conducted as follows. A microsomal membrane preparation was obtained from *Euglena* cells grown on liquid, heterotrophic, medium (Tani et al., supra) in the dark. Wax synthase activity was solubilized by treating the membranes with 2% (w/v) CHAPS and 500 mM NaCl in a buffered solution (25 mM Bis-Tris, pH 7.0, 1 mM EDTA and 10% (w/v) glycerol) for 1 hour on ice. After dilution of the CHAPS to 0.75% and the NaCl to 200 mM by addition of a dilution buffer, the sample was centrifuged at ~200,000×g for 1.5 hours. The supernatant fraction was loaded onto a Blue A dye column pre-equilibrated with Column Buffer (25 mM Bis-Tris pH 7.0, 1 mM EDTA, 10% glycerol, 0.75% CHAPS) which also contained 200 mM NaCl. The column was washed with Column Buffer containing 200 mM NaCl until the A280 of the effluent returned to the preload value. Wax synthase activity which had bound to the column was released by increasing the NaCl concentration in the Column Buffer to 1.5M. The fractions from the Blue A column containing wax synthase activity released by the 1.5M NaCl (~20 ml combined volume) were pooled and concentrated approximately 30-fold via ultrafiltration (Amicon® pressure cell fitted with a YM 30 membrane). The concentrated material from the Blue A column was used as the sample for a separation via size exclusion chromatography on Superose® 12 medium (Pharmacia®).

Approximately 200 μl of the sample was loaded onto a Superose 12 column (HR 10/30), pre-equilibrated with Column Buffer containing 0.5M NaCl, and developed at a flow rate of 0.1 ml/min. The wax synthase activity eluted from the column as a smooth peak. Comparison of the elution volume of the wax synthase activity with the elution profiles of molecular mass standard proteins yielded an estimate of 166 kD for the apparent molecular mass of the enzyme. Fractions which contained wax synthase activity were analyzed via SDS-polyacrylamide gel electrophoresis followed by silver staining. A preliminary analysis of the polypeptide profiles of the various fractions did not reveal any proteins with molecular masses of 100 kD or greater whose staining intensity appeared to match the activity profile. The wax synthase polypeptide may be present as a minor component in the sample mixture that is not readily detectable on the silver-stained gel. Alternatively, the enzyme may be composed of subunits which are dissociated during SDS-PAGE.

Example 7

Isolation of Wax Synthase Nucleic Acid Sequences

DNA sequences encoding wax synthase peptides are obtained from jojoba using synthetic oligonucleotides designed from wax synthase peptide sequences. The wax synthase nucleic acid sequences may be obtained by amplification of DNA by polymerase chain reaction (PCR) using oligonucleotides as primers, or alternatively, by screening a cDNA or genomic DNA library by radiolabeling the oligonucleotides or previously isolated sequences for use as probes.

A. Construction of Jojoba cDNA Libraries

RNA may be isolated using the methods described by Cathala, et al. (1983) *DNA*, 3:329-335. RNA is isolated from jojoba embryos collected at 80-90 days post-anthesis using a polyribosome isolation method, initially described by Jackson and Larkins (*Plant Physiol.* (1976) 57:5-10), as modified by Goldberg et al. (*Developmental Biol.* (1981) 83:201-217). In this procedure all steps, unless specifically stated, are carried out at 4° C. 10 gm of tissue are ground in liquid nitrogen in a Waring blender until the tissue becomes a fine powder. After the liquid nitrogen has evaporated, 170 ml of extraction buffer (200 mM Tris pH 9.0, 160 mM KCl, 25 mM EGTA, 70 mM MgC12, 1% Triton X-100, 05% sodium deoxycholate, 1 mM spermidine, 10 mM β-mercaptoethanol, and 500 mM sucrose) is added and the tissue is homogenized for about 2 minutes. The homogenate is filtered through sterile miracloth and centrifuged at 12,000×g for 20 minutes. The supernatant is decanted into a 500 ml sterile flask, and 1/19 volume of a 20% detergent solution (20% Brij 35, 20% Tween 40, 20% Noidet p-40 w/v) is added at room temperature. The solution is stirred at 4° C. for 30 minutes at a moderate speed and the supernatant is then centrifuged at 12,000×g for 30 minutes.

About 30 ml of supernatant is aliquoted into sterile Ti 60 centrifuge tubes and underlaid with 7 ml of a solution containing 40 mM Tris pH 9.0, 5 mM EGTA, 200 mM KCl, 30 mM MgC12, 1.8M sucrose, 5 mM β-mercaptoethanol. The tubes are filled to the top with extraction buffer, and spun at 60,000 rpm for 4 hours at 4° C. in a Ti60 rotor. Following centrifugation, the supernatant is aspirated off and 0.5 ml of resuspension buffer (40 mM Tris pH 9.0, 5 mM EGTA, 200 mM KCl, 30 mM MgCl$_2$, 5 mM β-mercaptoethanol) is added to each tube. The tubes are placed on ice for 10 minutes, after which the pellets are thoroughly resuspended and pooled. The supernatant is then centrifuged at 120×g for 10 minutes to remove insoluble material. One volume of self-digested 1 mg/ml proteinase K in 20 mM Tris pH 7.6, 200 mM EDTA, 2% N-lauryl-sarcosinate is added to the supernatant and the mixture incubated at room temperature for 30 minutes.

RNA is precipitated by adding 1/10 volume of sodium acetate and 2 volumes of ethanol. After several hours at −20° C. RNA is pelleted by centrifugation at 12,000×g at 4° C. for 30 minutes. The pellet is resuspended in 10 ml of TE buffer (10 mM Tris, 1 mM EDTA) and extracted with an equal volume of Tris pH 7.5 saturated phenol. The phases are separated by centrifuging at 10,000×g for 20 minutes at 4° C. The aqueous phase is removed and the organic phase is re-extracted with one volume of TE buffer. The aqueous phases are then pooled and extracted with one volume of chloroform. The phases are again separated by centrifugation and the aqueous phase ethanol precipitated as previously described, to yield the polyribosomal RNA.

Polysaccharide contaminants in the polyribosomal RNA preparation are removed by running the RNA over a cellulose column (Sigma-cell 50) in high salt buffer (0.5M NaCl, 20 mM Tris pH 7.5, 1 mM EDTA, 0.1% SDS). The contaminant binds to the column and the RNA is collected in the eluant. The eluant fractions are pooled and the RNA is ethanol precipitated. The precipitated total RNA is then resuspended in a smaller volume and applied to an oligo d(T) cellulose column to isolate the polyadenylated RNA.

Polyadenylated RNA is used to construct a cDNA library in the plasmid cloning vector pCGN1703, derived from the commercial cloning vector Bluescribe M13-(Stratagene Cloning Systems; San Diego, Calif.), and made as follows. The polylinker of Bluescribe M13- is altered by digestion with BamHI, treatment with mung bean endonuclease, and blunt-end ligation to create a BamHI-deleted plasmid, pCGN1700. pCGN1700 is digested with EcoRI and SstI (adjacent restriction sites) and annealed with a synthetic linker having restriction sites for BamHI, PstI, XbaI, ApaI and SmaI, a 5' overhang of AATT, and a 3' overhang of TCGA. The insertion of the linker into pCGN1700 eliminates the EcoRI site, recreates the SstI (also, sometimes referred to as "SacI" herein) site found in Bluescribe, and adds the new restriction sites contained on the linker. The resulting plasmid pCGN1702, is digested with HindIII and blunt-ended with Klenow enzyme; the linear DNA is partially digested with PvuII and ligated with T4 DNA wax synthase in dilute solution. A transformant having the lac promoter region deleted is selected (pCGN1703) and is used as the plasmid cloning vector.

Briefly, the cloning method for cDNA synthesis is as follows. The plasmid cloning vector is digested with SstI and homopolymer T-tails are generated on the resulting 3'-overhang stick-ends using terminal deoxynucleotidyl transferase. The tailed plasmid is separated from undigested or un-tailed plasmid by oligo(dA)-cellulose chromatography. The resultant vector serves as the primer for synthesis of cDNA first strands covalently attached to either end of the vector plasmid. The cDNA-mRNA-vector complexes are treated with terminal transferase in the presence of deoxyguanosine triphosphate, generating G-tails at the ends of the cDNA strands. The extra cDNA-mRNA complex, adjacent to the BamHI site, is removed by BamHI digestion, leaving a cDNA-mRNA-vector complex with a BamHI stick-end at one end and a G-tail at the other. This complex is cyclized using an annealed synthetic cyclizing linker which has a 5' BamHI sticky-end, recognition sequences for restriction enzymes NotI, EcoRI and SstI, and a 3° C.-tail end. Following ligation and repair the circular complexes are transformed into *E. coli* strain DH5a (BRL®, Gaithersburg, Md.) to generate the cDNA library. The jojoba embryo cDNA bank contains between approximately 1.5×10$^6$ clones with an average cDNA insert size of approximately 500 base pairs.

Additionally, jojoba polyadenylated RNA is also used to construct a cDNA library in the cloning vector ZAPII/EcoRI (Stratagene®, San Diego, Calif.). The library is constructed using protocols, DNA and bacterial strains as supplied by the manufacturer. Clones are packaged using Gigapack® Gold packaging extracts (Stratagene®), also according to manufacturer's recommendations. The cDNA library constructed in this manner contains approximately 1×10$^6$ clones with an average cDNA insert size of approximately 400 base pairs.

B. Synthetic Oligonucleotides

In general, for use as PCR primers from single stranded DNA template reverse-transcribed from mRNA, oligonucleotides containing the sense orientation sequence corresponding to wax synthase peptide encoding sequences are prepared. These oligonucleotides are used as primers for the "forward" amplification reaction to produce sense strand DNA.

For the "reverse" reaction for amplification of the non-coding DNA strand, an oligonucleotide may be designed to be identical to a portion of a primer used to prepare DNA template for PCR. Alternatively, oligonucleotides which contain sequence complementary to wax synthase peptide encoding sequences may be used in combination with a "forward" wax synthase oligonucleotide primer as described above.

Where the wax synthase peptide sequences contain amino acids which may be encoded by a number of different codons, the forward or reverse primers may be "degenerate" oligonucleotides, i.e. containing a mixture of all or some of the possible encoding sequences for a particular peptide region. To reduce the number of different oligonucleotides present in such a mixture, it is preferable to select peptide regions which have the least number of possible encoding sequences when preparing the synthetic oligonucleotide for PCR primers. Similarly, where the synthetic oligonucleotide is to be used to directly screen a library for wax synthase sequences, lower degeneracy oligonucleotides are preferred.

Following is an example of the sequence of peptide WSPEP29 (center line, SEQ ID NO: 20) and the forward (top line, SEQ ID NO: 22) and reverse (bottom line, SEQ ID NO: 23) DNA sequences that encode the peptide WSPEP29.

```
5' TTY GTN CCN GCN GTN GCN CCN CAY GGN GGN GCN YTN MGN 3'   (SEQ ID NO:22)
    F   V   P   A   V   A   P   H   G   G   A   L   R       (SEQ ID NO:20)
3' AAR CAN GGN CGN CAN CGN GGN GTR CCN CCN CGN RAN KCN 5'   (SEQ ID NO:23)
```

Following is an example of the sequence of peptide WSPEP33 (center line, SEQ ID NO: 21) and the forward (top line, SEQ ID NO: 24) and reverse (bottom line, SEQ ID NO: 25) DNA sequences that encode the peptide WSPEP33.

```
5' ACN ATH GAY GAR TAY CCN GTN ATG TTY AAY TAY ACN CAR AAR 3'   (SEQ ID NO:24)
    T   I   D   E   Y   P   V   M   F   N   Y   T   Q   K       (SEQ ID NO:21)
3' TGN TAD CTR CTY ATR GGN CAN TAC AAR TTR ATR TGN GTY TTY 5'   (SEQ ID NO:25)
```

Following is an example of the sequence of peptide WSPEP14 (center line, SEQ ID NO: 26) and the forward (top line, SEQ ID NO: 27) and reverse (bottom line, SEQ ID NO: 28) DNA sequences that encode the peptide WSPEP14.

```
                                              (SEQ ID NO:27)
5' TTY MGN GAY GAY CCN WSN AAY GAY CAY 3'

(SEQ ID NO:26)
    F   R   D   D   P   S   N   D   H (SEQ ID NO:28)
3' AAR KCN CTR CTR GGN WSN TTR CTR GTR 5'
```

Following are sequences of synthetic oligonucleotides which may be used to obtain wax synthase sequences. The oligonucleotide names reflect the particular wax synthase peptide fragment numbers as listed in Example 5. The letter "F" in the oligonucleotide name designates a PCR forward reaction primer. The letter "R" designates a PCR reverse reaction primer.

```
WSPEP29-F1
5' TTYGTNCCNGCNGTNGC 3'           (SEQ ID NO:29)
```

-continued

```
WSPEP29-F2
5' GCNCCNCAYGGNGGNGC 3'           (SEQ ID NO:30)

WSPEP29-R1
5' GCNCCNCCRTGNGGNGC 3'           (SEQ ID NO:31)

WSPEP29-R2
5' GCNACNGCNGGNACRAA 3'           (SEQ ID NO:32)

WSPEP33-F1
5' ACNATHGAYGARTAYCCNGT 3'        (SEQ ID NO:33)

WSPEP33-F2
5' CCNGTNATGTTYAAYTAYAC 3'        (SEQ ID NO:34)

WSPEP33-R1
5' TTYTGNGTRTARTTRAACAT 3'        (SEQ ID NO:35)

WSPEP33-R2
5' AACATNACNGGRTAYTCRTC 3'        (SEQ ID NO:36)
```

-continued

```
WSPEP14-F1
5' GAYGAYCCNWSNAAYGAYCA           (SEQ ID NO:37)
```

-continued

```
WSPEP14-R1
5' TGRTCRTTNSWNGGRTCRTC           (SEQ ID NO:38)
```

The nucleotide base codes for the above oligonucleotides are as follows:

| | | |
|---|---|---|
| A = adenine | T = thymine | Y = cytosine or thymine |
| C = cytosine | U = uracil | R = adenine or guanine |
| G = guanine | I = inosine | O = inosine or cytosine |
| H = adenine, cytosine or thymine | | |
| N = adenine, cytosine, guanine or thymine | | |
| W = adenine or thymine | | |
| S = guanine or cytosine | | |
| B = guanine, cytosine or thymine | | |
| K = guanine or thymine | | |
| M = adenine or cytosine | | |

C. PCR Reactions

Poly(A)+RNA is isolated from total RNA prepared from jojoba tissue as described above. cDNA is prepared from poly(A)+ or total RNA by reverse transcription using the Marathon® cDNA Amplification Kit (Clontech® Laboratories Inc.) according to the manufacturer's directions. The jojoba cDNA is used in PCR reactions 1-16 set forth below.

PCR is conducted in a Perkin Elmer® Cetus™ Gene-Amp® PCR System 9600 PCR machine using reverse transcribed single-stranded cDNA as template. Commercially available PCR reaction and optimization reagents are used according to manufacturer's specifications

| Reaction | Forward Primer | Reverse Primer |
|---|---|---|
| 1 | WSPEP14-F1 (SEQ ID NO:37) | WSPEP29-R1 (SEQ ID NO:31) |
| 2 | WSPEP14-F1 (SEQ ID NO:37) | WSPEP29-R2 (SEQ ID NO:32) |
| 3 | WSPEP14-F1 (SEQ ID NO:37) | WSPEP33-R1 (SEQ ID NO:35) |
| 4 | WSPEP14-F1 (SEQ ID NO:37) | WSPEP33-R2 (SEQ ID NO:36) |
| 5 | WSPEP29-F1 (SEQ ID NO:29) | WSPEP14-R1 (SEQ ID NO:38) |
| 6 | WSPEP29-F1 (SEQ ID NO:29) | WSPEP33-R1 (SEQ ID NO:35) |
| 7 | WSPEP29-F1 (SEQ ID NO:29) | WSPEP33-R2 (SEQ ID NO:36) |
| 8 | WSPEP29-F2 (SEQ ID NO:30) | WSPEP14-R1 (SEQ ID NO:38) |
| 9 | WSPEP29-F2 (SEQ ID NO:30) | WSPEP33-R1 (SEQ ID NO:35) |
| 10 | WSPEP29-F2 (SEQ ID NO:30) | WSPEP33-R2 (SEQ ID NO:36) |
| 11 | WSPEP33-F1 (SEQ ID NO:33) | WSPEP14-R1 (SEQ ID NO:38) |
| 12 | WSPEP33-F1 (SEQ ID NO:33) | WSPEP29-R1 (SEQ ID NO:31) |
| 13 | WSPEP33-F1 (SEQ ID NO:33) | WSPEP29-R2 (SEQ ID NO:32) |
| 14 | WSPEP33-F2 (SEQ ID NO:34) | WSPEP14-R1 (SEQ ID NO:38) |
| 15 | WSPEP33-F2 (SEQ ID NO:34) | WSPEP29-R1 (SEQ ID NO:31) |
| 16 | WSPEP33-F2 (SEQ ID NO:34) | WSPEP29-R2 (SEQ ID NO:32) |

The temperature program used for PCR amplification is as follows: 1 cycle of 95 degrees C. for 2 minutes; 4 cycles of 95 degrees C. for 30 seconds, 60 degrees C. for 1 minute, and 72 degrees C. for 4 minutes; 4 cycles of 95 degrees C. for 30 seconds, 57 degrees C. for 1 minute, and 72 degrees C. for 4 minutes; 4 cycles of 95 degrees C. for 30 seconds, 54 degrees C. for 1 minute, and 72 degrees C. for 4 minutes; 4 cycles of 95 degrees C. for 30 seconds, 51 degrees C. for 1 minute, and 72 degrees C. for 4 minutes; and 25 cycles of 95 degrees C. for 30 seconds, 48 degrees C. for 1 minute, and 72 degrees C. for 4 minutes.

Figure 3:
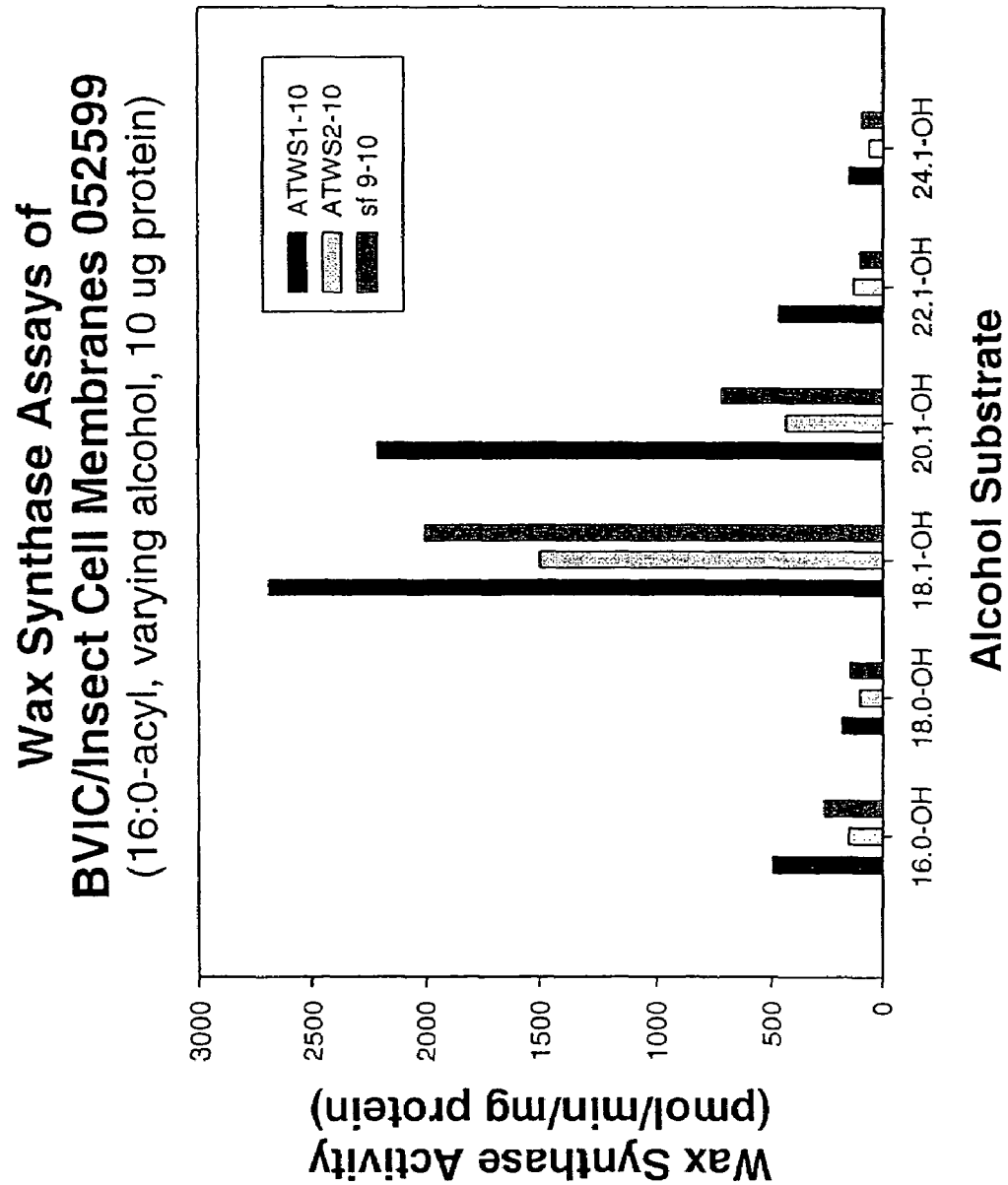
FIG. 3 Results of wax synthase activity assay using various alcohol substrates and 10 ug 16:0-CoA substrate.
Figure 4:
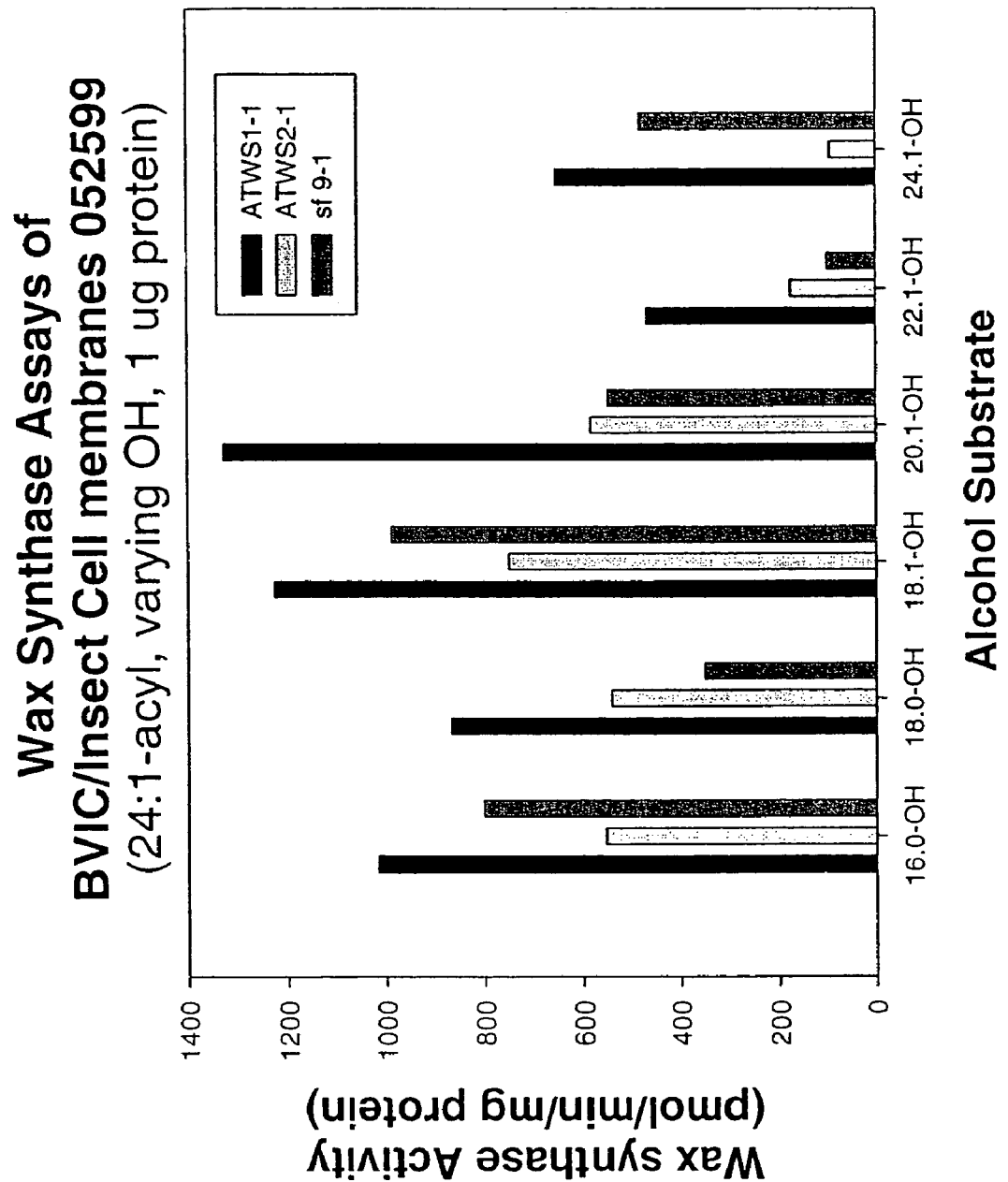
FIG. 4 Results of wax synthase activity assay using various alcohol substrates and 1 ug 24:1-CoA substrate.
Figure 5:
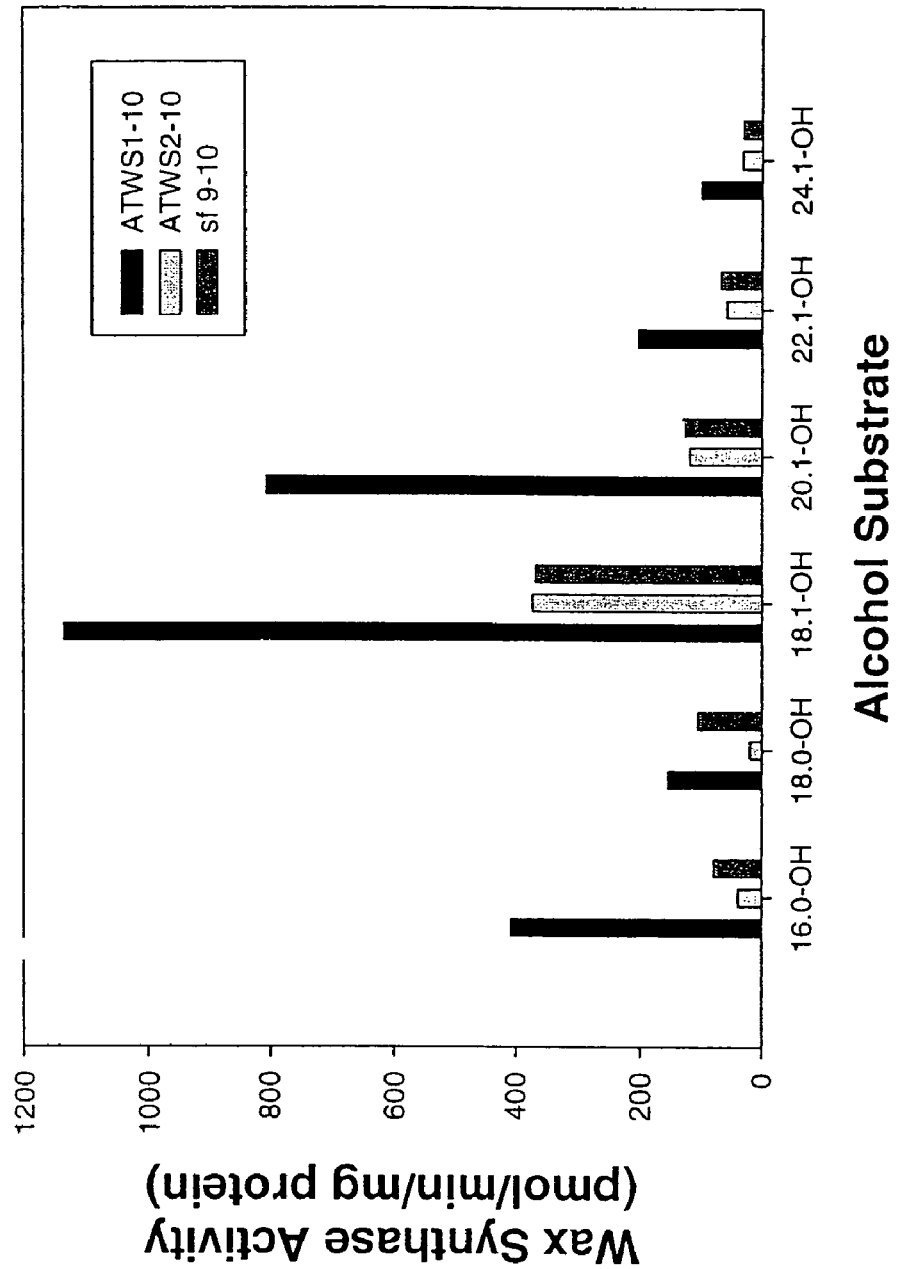
FIG. 5 Results of wax synthase activity assay using various alcohol substrates and 10 ug 24:1-CoA substrate.

From reactions 3 and 4, a PCR product approximately 700 nucleotides in length was detected. The PCR product was purified using gel electrophoresis and cloned into pCR2.1 using a Topo® TA cloning kit (Invitrogen® Corp.). The DNA sequence of the cloned PCR product was determined and was 708 nucleotides long (FIG. 3).

The entire cDNA can be amplified using 5' and 3' RACE (Frohman et al., 1988) using the Marathon cDNA Amplification Kit (Clontech® Laboratories Inc.) according to the manufacturers instructions. From the sequence of the 708 nucleotide PCR fragment (SEQ ID NO: 39) derived using primers WSPEP14-F1 and WSPEP33-R2 the following primers were synthesized:

```
WSRACEF1
GATTTGCCTCATTTTGTGATCTCGGTGCT     (SEQ ID NO:39)

WSRACEF2
GACCTATACCCCCAGTTCAACGAGCCATAC    (SEQ ID NO:40)

WSRACEF3
TTCAACGAGCCATACTTAGCCACCTCGCTG    (SEQ ID NO:41)

WSRACER1
AACAACCACCCTCCAGTCACCATCACGAAC    (SEQ ID NO:42)

WSRACER2
TTGCCTGAAACCGCCTTCTTCACCACCATC    (SEQ ID NO:61)

WSRACER3
AAGATGTCTGACACCATGAGGTTCCACCTG    (SEQ ID NO:43)
```

3'RACE reactions were set up using primers WSRACEF1, WSRACEF2, and WSRACEF3. 5'RACE reactions were set up using primers WSRACER1, WSRACER2, and WSRACER3. PCR reactions were performed according to the manufacturer's protocol (Clontech® Laboratories Inc.). All 6 PCR reactions gave visible PCR products ranging in size from approximately 700 nucleotides to 1000 nucleotides. The PCR products were gel purified and cloned into pCR2.1 according to the manufacturer's protocol (Invitrogen® Corp.). The DNA sequence of several clones from both the 5' and 3' RACE reactions and the previous PCR product derived from primers WSPEP14-F1 and WSPEP33-R2 were assembled using sequencher software (Gene Codes Corp.®). The assembled sequence of all the PCR products contains the coding region of the cDNA sequence.

To isolate a gene fragment suitable for cloning the wax synthase gene into expression cassettes for plant lipid modification, the coding region of the gene can be amplified from cDNA using the primers WAXSYNFOR (SEQ ID NO: 22) and WASXYNREV (SEQ ID NO: 23). The sequence of WAXSYNFOR is GGATCCGTCGACACAATGGAGGTGGAGAAGGAGCTAAAG, and the sequence of WASXYNREV is GCATGCAGATCTCACCACCCCAACAAACCCATC. The PCR reaction is performed using the Marathon® CDNA (Clontech® Laboratories Inc.) according to the manufacturer's instructions. The PCR program consists of 30 cycles of 94 degrees C. for 15 seconds, 60 degrees C. for 1 minute, 72 degrees C. for 2 minutes. The PCR products were cloned into pCR2.1 according to the manufacturers protocol (Invitrogen® Corp.). The resulting plasmid was designated pCGN8538. The nucleic acid sequence and the derived amino acid sequence of the jojoba wax synthase is determine and provided in FIGS. 10 and 11, respectively.

Example 8

Generation of Transgenic Plants Containing the Wax Synthase cDNA

Two plant binary vectors were constructed. Plasmid pCGN8559 contains 3 genes necessary for wax biosynthesis: the condensing enzyme involved in fatty acid elongation to chain lengths greater than 18 carbons (KCS), the acyl-CoA reductase involved in formation of fatty alcohols, and the wax synthase. A control plasmid, pCGN8557, contains the KCS and acyl-CoA reductase genes. The Asp718 fragment of pCGN7698, which contains the jojoba acyl-CoA reductase under control of napin regulatory sequences, was cloned into the Asp718 site of binary vector pCGN5139 to form pCGN8555. The NotI fragment of pCGN7844, which contains the Lunaria KCS under control of napin regulatory sequences, was cloned into the NotI site of pCGN8555 to form pCGN 8557. The SalI-BglII fragment from pCGN8538 which contains the coding region of the jojoba wax synthase gene, was cloned into the napin expression cassette of pCGN7770 digested with the same two restriction endonucleases to form pCGN8553. The Sse8387 fragment of pCGN8553, which contains the jojoba wax synthase under control of napin regulatory sequences, was cloned into the Sse8387 site of pCGN8557 to form pCGN8559. The binary vectors were introduced into *Agrobacterium tumefaciens* EHA105 via electroporation. The vectors were used to transform *Arabidopsis thaliana* ecotype No-O according to the vacuum infiltration protocol of Bent et al. (1994, Science 265:1856-1860).

Example 9

Analysis of Developing *Arabidopsis* Seed

Siliques were harvested from seven *Arabidopsis* plants transformed with pCGN8559 which were in various stages of development. Developing seed was removed from ten siliques collected from each plant and homogenized in 275 µl of buffer (100 mM HEPES/NaOH pH 7.5, 250 mM NaCl). A portion of the homogenate (200 µl) was centrifuged at 16000×g for 20 minutes at 4° C. resulting in a supernatant and pellet. The pellet was resuspended in 200 µl of the same buffer. The homogenate and the two fractions were assayed for wax synthase activity according to the protocol detailed in Example 1B. 25 µl of sample were used per assay in a final volume of 250 µl. The assay buffer contained 40 µM $1\text{-}^{14}C$ 16:0-CoA (specific activity 5 µCi/µmol), 200 µM 18:1 alcohol, 50 mM HEPES/NaOH pH 7.5, 250 mM NaCl and 2 mM β-mercaptoethanol. TLC analysis showed the incorporation of radiolabel from $1\text{-}^{14}C$ 16:0-CoA into a band which comigrated with a wax standard in 5 of the 7 plants analyzed. This activity was detected in the homogenate and pellet fractions but not in the supernatant fraction. The wax synthase activity detected in these samples is several orders of magnitude greater than an endogenous wax synthase activity previously shown to be present in developing *Arabidopsis* seed. The activity detected in 8612-3 and 8613-2 is indicative of this endogenous "background" activity. A positive control for wax activity was the jojoba (DP2) membrane fraction.

Example 10

Analysis of the Seed Oil

A. Thin-Layer Chromatographic Analysis

Seeds from *Arabidopsis* plants were homogenized in hexane using a mortar and pestle. The hexane was transferred to a new vial and evaporated under nitrogen gas and the oil was resuspended in hexane at a concentration of 10 mg/ml. 10 µl of the oil solution was spotted on a silica gel-G TLC plate and the chromatogram was developed in hexane: diethyl ether:acetic acid (80:20:1). The lipids were stained with iodine. Elevated levels of wax were seen in the oil extracted from plants expressing pCGN8559 that also tested positive for wax synthase activity by assay. Intermediate levels of wax were detected in seeds from pCGN8557 which contained only reductase/KCS and low, background levels of wax were detected in *Arabidopsis* No-O controls.

B. Gas Chromatographic Analysis

The oil in about 10 mg of *Arabidopsis* seed was derivatized to form fatty acid methyl esters (FAME) and free alcohol. The extractable lipid was analyzed for FAME and alcohol content by gas chromatography. Internal standard 17:0 TAG was spiked into the lipid fraction and derivatization was carried out at 90° C. in the presence of acidic methanol and toluene. Lipid products were extracted by adding hexane and 1M aqueous NaCl. The fatty acid methyl esters (FAME) and alcohols were separated on a 0.25 mm×15 m Supelcowax-10 column. Percent composition of the products was determined by their weight contribution to the sample (Table 3A). A correction factor for the Flame Ionization Detector (FID) response, determined experimentally to be 1.155, was used to adjust the quantitation of the alcohol peak relative to the 17:0 methyl ester standard. The weight composition was used to determine the percentage of very long chain carbon groups (>18C) present (Table 3B).

| A | Fatty Acyl Groups | | | | | | | | | | | | | |
|---|---|---|---|---|---|---|---|---|---|---|---|---|---|---|
| Sample | 16:0 | 16:1 | 18:0 | 18:1 | 18:2 | 18:3 | 20:0 | 20:1 | 20:2 | 22:0 | 22:1 | 22:2 | 24:0 | 24:1 |
| 8559-3 | 6.1 | 0.3 | 2.3 | 14.7 | 21.5 | 19.3 | 1.1 | 12.2 | 1.0 | 0.8 | 9.8 | 0.1 | 1.0 | 3.4 |
| 8559-4 | 6.1 | 0.3 | 2.8 | 17.5 | 25.1 | 18.9 | 2.2 | 22.1 | 1.9 | 0.3 | 2.4 | 0.1 | 0.1 | 0.2 |
| 8559-5 | 6.1 | 0.3 | 2.8 | 17.2 | 25.4 | 18.9 | 2.3 | 22.0 | 1.9 | 0.3 | 2.4 | 0.1 | 0.1 | 0.2 |
| 8559-6 | 6.0 | 0.3 | 2.7 | 17.9 | 25.4 | 18.9 | 2.2 | 21.7 | 1.9 | 0.3 | 2.4 | 0.1 | 0.1 | 0.2 |
| 8559-7 | 6.0 | 0.3 | 2.6 | 17.0 | 25.2 | 19.6 | 2.2 | 22.1 | 1.9 | 0.3 | 2.4 | 0.1 | 0.1 | 0.2 |
| 8559-8 | 5.9 | 0.3 | 2.2 | 14.9 | 21.4 | 18.7 | 1.1 | 13.5 | 1.1 | 0.7 | 8.7 | 0.2 | 0.6 | 2.0 |
| 8559-9 | 5.9 | 0.4 | 2.0 | 13.3 | 21.7 | 14.8 | 1.2 | 12.9 | 1.1 | 0.7 | 8.8 | 0.2 | 1.7 | 6.5 |
| 8559-10 | 5.7 | 0.4 | 1.9 | 13.5 | 20.6 | 19.0 | 1.0 | 10.7 | 0.9 | 0.8 | 10.1 | 0.2 | 1.3 | 5.5 |
| 8559-11 | 5.5 | 0.2 | 1.6 | 10.9 | 17.5 | 17.8 | 0.7 | 8.9 | 0.7 | 0.9 | 11.3 | 0.2 | 1.3 | 5.3 |
| 8559-13 | 6.1 | 0.3 | 2.8 | 16.8 | 24.3 | 18.8 | 2.1 | 19.4 | 1.6 | 0.5 | 5.3 | 0.1 | 0.4 | 1.3 |
| 8559-14 | 5.6 | 0.3 | 2.7 | 18.3 | 24.4 | 18.5 | 2.2 | 22.5 | 2.0 | 0.3 | 2.8 | 0.1 | 0.1 | 0.2 |
| 8559-15 | 6.1 | 0.5 | 1.8 | 12.6 | 20.8 | 16.4 | 1.0 | 11.8 | 1.0 | 0.8 | 9.4 | 0.2 | 1.1 | 4.5 |
| 8559-16 | 5.9 | 0.3 | 2.8 | 17.9 | 24.4 | 18.5 | 2.3 | 22.6 | 1.9 | 0.3 | 2.6 | 0.1 | 0.2 | 0.2 |
| 8559-17 | 5.8 | 0.3 | 2.5 | 16.7 | 23.2 | 18.9 | 1.7 | 17.2 | 1.4 | 0.6 | 7.3 | 0.1 | 0.5 | 2.3 |
| 8559-18 | 5.7 | 0.4 | 1.7 | 10.9 | 18.5 | 16.4 | 1.0 | 12.4 | 1.0 | 0.8 | 8.3 | 0.2 | 1.2 | 4.3 |
| 8557-1 | 5.6 | 0.3 | 2.4 | 16.6 | 22.5 | 19.6 | 1.5 | 15.4 | 1.3 | 0.6 | 8.0 | 0.2 | 0.5 | 2.7 |
| 8557-3 | 5.9 | 0.3 | 2.6 | 16.6 | 22.3 | 21.1 | 2.1 | 21.4 | 2.1 | 0.3 | 2.8 | 0.1 | 0.1 | 0.2 |
| 8557-4 | 6.4 | 0.4 | 2.5 | 14.1 | 23.0 | 17.7 | 1.4 | 12.8 | 1.3 | 0.8 | 8.8 | 0.2 | 0.8 | 2.5 |
| 8557-5 | 5.6 | 0.2 | 2.3 | 13.6 | 21.9 | 21.8 | 1.1 | 11.3 | 1.3 | 0.8 | 10.9 | 0.2 | 0.7 | 3.2 |
| 8557-6 | 5.8 | 0.4 | 2.6 | 14.4 | 23.1 | 19.6 | 1.4 | 14.3 | 1.4 | 0.7 | 8.8 | 0.2 | 0.7 | 3.1 |
| 8557-7 | 5.5 | 0.3 | 2.4 | 13.7 | 23.2 | 21.0 | 1.6 | 17.4 | 1.7 | 0.6 | 8.9 | 0.2 | 0.5 | 2.8 |
| 8557-8 | 6.0 | 0.4 | 2.3 | 12.6 | 21.5 | 20.9 | 0.9 | 8.7 | 1.0 | 0.9 | 12.3 | 0.3 | 0.9 | 4.3 |

-continued

| Sample | | | | | | | | | | | | | | |
|---|---|---|---|---|---|---|---|---|---|---|---|---|---|---|
| 8557-9 | 5.6 | 0.3 | 2.4 | 14.4 | 22.5 | 21.7 | 1.2 | 12.6 | 1.3 | 0.7 | 10.5 | 0.2 | 0.6 | 3.1 |
| 8557-10 | 6.0 | 0.3 | 2.5 | 14.3 | 22.6 | 21.1 | 1.2 | 11.7 | 1.3 | 0.8 | 10.1 | 0.2 | 0.7 | 3.0 |
| 8557-11 | 6.0 | 0.4 | 2.5 | 13.2 | 22.4 | 19.5 | 1.2 | 11.8 | 1.2 | 0.8 | 10.1 | 0.2 | 0.9 | 3.8 |
| 8557-12 | 5.7 | 0.3 | 2.8 | 16.3 | 24.5 | 19.4 | 2.1 | 23.4 | 2.1 | 0.3 | 2.6 | 0.1 | 0.1 | 0.2 |
| 8557-13 | 6.1 | 0.3 | 2.5 | 13.3 | 22.3 | 21.2 | 1.1 | 11.2 | 1.2 | 0.8 | 10.6 | 0.2 | 0.7 | 3.0 |
| 8557-14 | 5.9 | 0.2 | 2.5 | 13.4 | 23.0 | 19.4 | 1.1 | 11.4 | 1.3 | 0.8 | 10.9 | 0.2 | 0.7 | 2.9 |
| No-O-1 | 6.5 | 0.4 | 3.1 | 15.6 | 26.3 | 17.7 | 2.7 | 22.1 | 2.1 | 0.4 | 2.6 | 0.2 | 0.2 | 0.2 |
| No-O-2 | 6.4 | 0.4 | 3.1 | 15.6 | 26.2 | 17.9 | 2.7 | 22.0 | 2.1 | 0.4 | 2.6 | 0.2 | 0.2 | 0.2 |
| No-O-3 | 6.4 | 0.4 | 3.1 | 15.6 | 26.3 | 17.6 | 2.7 | 22.1 | 2.1 | 0.4 | 2.6 | 0.2 | 0.2 | 0.2 |

| A | B | | | | |
|---|---|---|---|---|---|
| | Fatty Alcohols | | | | VLCFA |
| Sample | OH18:1 | OH20:1 | OH22:1 | OH24:1 | wt % |
| 8559-3 | 0.1 | 0.5 | 3.3 | 2.4 | 35.7 |
| 8559-4 | 0.0 | 0.0 | 0.0 | 0.0 | 29.4 |
| 8559-5 | 0.0 | 0.0 | 0.0 | 0.0 | 29.3 |
| 8559-6 | 0.0 | 0.0 | 0.0 | 0.0 | 28.8 |
| 8559-7 | 0.0 | 0.0 | 0.0 | 0.0 | 29.4 |
| 8559-8 | 0.1 | 1.0 | 5.3 | 2.2 | 36.5 |
| 8559-9 | 0.1 | 0.4 | 3.8 | 4.4 | 42.0 |
| 8559-10 | 0.0 | 0.5 | 4.2 | 3.6 | 38.9 |
| 8559-11 | 0.2 | 1.1 | 9.3 | 6.5 | 46.5 |
| 8559-13 | 0.0 | 0.1 | 0.1 | 0.1 | 31.0 |
| 8559-14 | 0.0 | 0.0 | 0.0 | 0.0 | 30.2 |
| 8559-15 | 0.2 | 0.8 | 6.7 | 4.3 | 41.9 |
| 8559-16 | 0.0 | 0.0 | 0.0 | 0.0 | 30.2 |
| 8559-17 | 0.0 | 0.2 | 0.7 | 0.5 | 32.5 |
| 8559-18 | 0.0 | 1.3 | 9.9 | 5.9 | 46.4 |
| 8557-1 | 0.0 | 0.1 | 1.1 | 1.5 | 33.0 |
| 8557-3 | 0.0 | 1.8 | 0.2 | 0.0 | 31.1 |
| 8557-4 | 0.0 | 0.3 | 2.9 | 4.2 | 35.9 |
| 8557-5 | 0.0 | 0.2 | 2.1 | 2.8 | 34.6 |
| 8557-6 | 0.0 | 0.1 | 1.3 | 2.1 | 34.1 |
| 8557-7 | 0.0 | 0.0 | 0.1 | 0.2 | 34.0 |
| 8557-8 | 0.0 | 0.2 | 2.6 | 4.0 | 36.2 |
| 8557-9 | 0.0 | 0.1 | 1.2 | 1.4 | 33.1 |
| 8557-10 | 0.0 | 0.2 | 1.9 | 2.4 | 33.3 |
| 8557-11 | 0.0 | 0.2 | 2.2 | 3.6 | 36.0 |
| 8557-12 | 0.0 | 0.0 | 0.0 | 0.0 | 30.9 |
| 8557-13 | 0.0 | 0.2 | 2.1 | 3.0 | 34.2 |
| 8557-14 | 0.0 | 0.2 | 2.7 | 3.2 | 35.5 |
| No-O-1 | 0.0 | 0.0 | 0.0 | 0.0 | 30.5 |
| No-O-2 | 0.0 | 0.0 | 0.0 | 0.0 | 30.4 |
| No-O-3 | 0.0 | 0.0 | 0.0 | 0.0 | 30.6 |

C. $^{13}$C-NMR Analysis of Intact *Arabidopsis* Seed

TLC analysis showed that plants expressing pCGN8559 did not contain any free alcohol therefore the alcohol peak present in the transmethylated samples was likely due to the derivatization of wax present in the seed oil. Based on this evidence it is estimated the amount of wax in plants expressing pCGN8559 at twice the weight of the alcohol detected by gas chromatography (Table 4A). This was not the case for plants expressing pCGN8557 where both alcohol and wax spots were visible by TLC after exposure to iodine vapor. In order to find a more direct measure of the amount of wax present, $^{13}$C-NMR spectra is obtained for intact mature *Arabidopsis* seed to determine the molar ratio of wax and TAG. A region of the spectra between 60-70 ppm was identified as containing unique carbon shifts for the sn-2 carbon of the glycerol backbone at 69.5 ppm, representing the molar amount of TAG, and the first carbon on the alcohol side of the wax ester linkage at 64.2 ppm, representing the molar amount of wax. Ratios of these two unique carbons were determined. From these ratios the mole percent wax was calculated (Table 4B). The mole percent data was converted to weight percent data using the following conversion:

$$\text{Wt \%} = 100 * \frac{(\text{mole \% wax} * \text{molecular weight wax})}{(\text{mole \% wax} * \text{MW wax}) + [(100 - \text{mole \% wax}) * \text{MW TAG}]}$$

The molecular weight of wax and TAG was assigned as 20:1-20:1 wax and tri 20:1 TAG.

The weight percent of wax calculated by the GC method was in agreement with the weight percent wax determined by the nondestructive measurement using $^{13}$C-NMR. Using this method a determination of the mole percent wax present in the plants expressing pCGN8557 is obtained. A calculation of the contribution of wax synthase to the production of very long chain fatty acids (VLCFAs) is shown in FIG. 1.

TABLE 4

| Sample | GC wt % OH | GC wt % wax | NMR wt % wax | Wax mole % wax |
|---|---|---|---|---|
| 8559-3 | 6.2 | 12.4 | 12.8 | 19.4 |
| 8559-4 | 0.0 | 0.0 | 0.0 | 0.0 |

TABLE 4-continued

| Sample | GC wt % OH | GC wt % wax | NMR wt % wax | Wax mole % wax |
|---|---|---|---|---|
| 8559-5 | 0.0 | 0.0 | 0.0 | 0.0 |
| 8559-6 | 0.0 | 0.0 | 0.0 | 0.0 |
| 8559-7 | 0.0 | 0.0 | 0.0 | 0.0 |
| 8559-8 | 8.6 | 17.1 | 17.2 | 25.4 |
| 8559-9 | 8.7 | 17.5 | nd | nd |
| 8559-10 | 8.4 | 16.7 | 15.5 | 23.1 |
| 8559-11 | 17.1 | 34.1 | 37.2 | 49.2 |
| 8559-13 | 0.3 | 0.5 | nd | nd |
| 8559-14 | 0.0 | 0.0 | nd | nd |
| 8559-15 | 12.0 | 24.1 | 24.4 | 34.6 |
| 8559-16 | 0.0 | 0.0 | 0.0 | 0.0 |
| 8559-17 | 1.4 | 2.8 | 1.9 | 3.0 |
| 8559-18 | 17.2 | 34.3 | 34.9 | 46.8 |
| 8557-1 | 2.7 | — | nd | nd |
| 8557-3 | 2.0 | — | 1.2 | 2.0 |
| 8557-4 | 7.4 | — | 9.9 | 15.3 |
| 8557-5 | 5.1 | — | 5.8 | 9.1 |
| 8557-6 | 3.6 | — | 3.8 | 6.0 |
| 8557-7 | 0.2 | — | 0.0 | 0.0 |
| 8557-8 | 6.8 | — | 10.4 | 16.0 |
| 8557-9 | 2.8 | — | 2.4 | 3.8 |
| 8557-10 | 4.4 | — | 6.3 | 9.9 |
| 8557-11 | 6.0 | — | 9.9 | 15.3 |
| 8557-12 | 0.0 | — | 0.0 | 0.0 |
| 8557-13 | 5.4 | — | 4.4 | 7.0 |
| 8557-14 | 6.1 | — | 7.4 | 11.5 |
| No-O-1 | 0.0 | — | 0.0 | |
| No-O-2 | 0.0 | — | 0.0 | |
| No-O-3 | 0.0 | — | nd | |

Example 11

Analysis of Transgenic *Arabidopsis* Leaves

Rosette leaves from plants transformed with construct pCGN 8593, expressing wax synthase under the control of the 35S promoter, were analyzed for wax synthase activity. Leaves were homogenized in 200 μl homogenization buffer (100 mM Tricine/NaOH, pH 7.8, 280 mM NaCl, 10% glycerol, and protease inhibitors 0.1 uM Aprotinin, 1 μM Leupeptin, and 100 μM Pefabloc) and the solids were pelleted by centrifugation at 16,000×g for 10 min and 4° C. The supernatant was removed and the pellet resuspended in 200 μl homogenization buffer. This fraction was referred to as the P1 fraction. Five control leaves harvested from *Arabidopsis cultivar* No-O were assayed as controls. The P1 fractions were assayed for wax synthase activity as described in Example 1B. Wax synthase activity in the plants expressing pCGN8593 was compared with the average activity found in the No-O controls. Eleven of the 24 plants analyzed demonstrated activity more than twice the average background level found in No-O. One plant demonstrated nearly a 10-fold increase in activity.

Example 12

Identification of Additional Wax Synthase Sequences

The protein sequence of the jojoba wax synthase (FIG. 11) is used to query the *Arabidopsis* DNA sequence database (available on the World Wide Web at genome-www-stanford.edu/*Arabidopsis*/). One of the accessions, P1 clone MTE17(Genbank® accession AB015479), contains 7 repeats of open reading frames with similarity to the jojoba wax synthase. The open reading frames have been designated ATWS1 to ATWS7 (FIGS. 12-18, respectively). They are found between nucleotides 23670 and 11479 of MTE17 using the numbering system of the Genbank® entry. The inferred protein sequences are aligned with the jojoba wax synthase sequence (FIG. 19) and a dendogram (FIG. 20) of their relationships is constructed using the Clustal W algorithm of MacVector® 6.5 (Oxford Molecular®). The sequence alignment in FIG. 19 shows a series of peptide sequences which are conserved between the amino acid sequences (Table 5). The percent identities and similarities are also determined, and are presented in table 6.

TABLE 5

| | SEQUENCE | SEQ ID NO: |
|---|---|---|
| 1 | LXLF(A/S)(F/L)XX(G/E) | 46 |
| 2 | PYL(A/S)TSL(Q/H)(D/E)FW(G/S)(R/H)RWNL(M/I)V | 47 |
| 3 | FX(V/T)SGXXHEXX(F/Y)FYX(I/T)R | 48 |
| 4 | P(S/T)(W/G)EV(T/A)XFF(V/L)LHG | 49 |

TABLE 6

| SEQUENCES COMPARED | PERCENT IDENTITY | PERCENT SIMILARITY |
|---|---|---|
| JoWS (SEQ ID NO:2) vs ATWS1 (SEQ ID NO:3) | 41% | 17% |
| JoWS (SEQ ID NO:2) vs ATWS2 (SEQ ID NO:5) | 37% | 19% |
| JoWS (SEQ ID NO:2) vs ATWS3 (SEQ ID NO:7) | 42% | 15% |
| JoWS (SEQ ID NO:2) vs ATWS4 (SEQ ID NO:9) | 42% | 16% |
| JoWS (SEQ ID NO:2) vs ATWS5 (SEQ ID NO:11) | 44% | 13% |
| JoWS (SEQ ID NO:2) vs ATWS6 (SEQ ID NO:13) | 41% | 17% |

TABLE 6-continued

| SEQUENCES COMPARED | PERCENT IDENTITY | PERCENT SIMILARITY |
|---|---|---|
| JoWS (SEQ ID NO:2) vs ATWS7 (SEQ ID NO:15) | 36% | 16% |
| ATWS3 (SEQ ID NO:7) vs ATWS6 (SEQ ID NO:13) | 59% | 14% |
| ATWS3 (SEQ ID NO:7) vs ATWS1 (SEQ ID NO:3) | 49% | 17% |
| ATWS3 (SEQ ID NO:7) vs ATWS4 (SEQ ID NO:9) | 71% | 10% |
| ATWS3 (SEQ ID NO:7) vs ATWS7 (SEQ ID NO:15) | 55% | 15% |
| ATWS3 (SEQ ID NO:7) vs ATWS2 (SEQ ID NO:5) | 49% | 21% |
| ATWS3 (SEQ ID NO:7) vs ATWS5 (SEQ ID NO:11) | 64% | 14% |
| ATWS6 (SEQ ID NO:13) vs ATWS1 (SEQ ID NO:3) | 47% | 18% |
| ATWS6 (SEQ ID NO:13) vs ATWS4 (SEQ ID NO:9) | 57% | 15% |
| ATWS6 (SEQ ID NO:13) vs ATWS7 (SEQ ID NO:15) | 51% | 17% |
| ATWS6 (SEQ ID NO:13) vs ATWS2 (SEQ ID NO:5) | 45% | 18% |
| ATWS6 (SEQ ID NO:13) vs ATWS5 (SEQ ID NO:11) | 57% | 15% |
| ATWS1 (SEQ ID NO:3) vs ATWS4 (SEQ ID NO:9) | 52% | 17% |
| ATWS1 (SEQ ID NO:3) vs ATWS7 (SEQ ID NO:15) | 46% | 19% |
| ATWS1 (SEQ ID NO:3) vs ATWS2 (SEQ ID NO:5) | 65% | 12% |
| ATWS1 (SEQ ID NO:3) vs ATWS5 (SEQ ID NO:11) | 49% | 17% |
| ATWS4 (SEQ ID NO:9) vs ATWS7 (SEQ ID NO:15) | 58% | 13% |
| ATWS4 (SEQ ID NO:9) vs ATWS2 (SEQ ID NO:5) | 50% | 19% |
| ATWS4 (SEQ ID NO:9) vs ATWS5 (SEQ ID NO:11) | 65% | 13% |
| ATWS7 (SEQ ID NO:15) vs ATWS2 (SEQ ID NO:5) | 45% | 18% |
| ATWS7 (SEQ ID NO:15) vs ATWS5 (SEQ ID NO:11) | 55% | 16% |
| ATWS2 (SEQ ID NO:5) vs ATWS5 (SEQ ID NO:11) | 49% | 17% |

Complementary DNA (cDNA) is constructed from *Arabidopsis* RNA isolated from immature seeds, whole seedlings (vegetative tissue), and inflorescences (flowers and flower stalks) using the SMART® PCR cDNA Library construction kit according to the manufacturer's protocol (Clontech®). SMART® cDNA is also constructed from RNA from *Brassica napus* leaves, and immature seeds harvested at 15 days after pollination (DAP), 18 DAP, and 30 DAP. The SMART cDNAs are used for virtual Northern analysis, according to the protocol in the SMART cDNA manual from Clontech®, of expression of the *Arabidopsis* ATWS cDNAs. ATWS2 is most highly expressed in *Arabidopsis* immature seeds and *Brassica* 30 DAP seeds. Expression is not detected in *Brassica* leaves or *Arabidopsis* seedlings. This is an expression pattern consistent with that expected for DAGAT, since triglycerides are primarily formed in developing seeds of these plants.

In addition, an expressed sequence tag (EST) sequence is identified from databases containing protein and nucleic acid sequences obtained from soybean (*Glycine max*). This sequence is provided in SEQ ID NO:19.

Example 13

Expression Constructs for AT-WS Homologues

13A. Expression in Insect Cell Cultures

Constructs are prepared to direct the expression of the *Arabidopsis* wax synthase homologous sequence in cultured insect cells. The entire coding region of the *Arabidopsis* wax synthase sequences, ATWS1 (SEQ ID NO:3) and ATWS2, (SEQ ID NO:5) and ATWS3 (SEQ ID NO:7) are amplified in a polymerase chain reaction (PCR) and subcloned into pCR2.1 (Invitrogen) to produce pCGN9705, pCGN9706 and pCGN9707, repsectively. Double stranded DNA sequence was obtained to verify that no errors were introduced by PCR amplification.

The fragment containing the entire coding region of the *Arabidopsis* ATWS1 (SEQ ID NO: 3) and ATWS2 (SEQ ID NO: 5) sequences was subcloned into baculovirus expression vector pFastBac1 (Gibco-BRL, Gaithersburg, Md.).

A baculovirus expression construct containing the ATWS1 (SEQ ID NO: 3) and ATWS2 (SEQ ID NO: 5) sequences is transformed and expressed using the BAC-to-BAC Baculovirus Expression System (Gibco-BRL, Gaithersburg, Md.) according to the manufacturer's directions, except harvesting of recombinant viruses was done 5 days post-transfection. The supernatant from the transfection mixture is used for generating virus stock which in turn is used for infecting Sf9 cells for use in the assay.

The transformed insect cells are assayed for wax synthase activity using methods described herein. Insect cells are centrifuged and the resulting pelletted cells were resuspended in Medium I (0.25 M sucrose and 1 mM EDTA in 10 mM Tris-Cl, pH 7.4) and homogenized on ice. The homogenate is centrifuged at 105,000×g for 1 at 4° C. Total membranes are resuspended in Medium I.

Wax synthase activity is determined using two different acyl-CoA substrates, 16:0-CoA, and 24:1-CoA, and five different alcohol substrates, 16:0-OH, 18:0-OH, 18:1-OH, 20:1-OH, 22:1-OH, and 24:1-OH. Wax synthase activity is assayed in a 0.25 ml reaction mixture containing 50 mM Tricine, pH 7.8, 2 mM β-mercaptoethanol, 250 mM sodium chloride, 200 μM respective alcohol (40 μM 18:1-OH) and, 20 μM 1-$^{14}$C palmitoyl-CoA, or 1-$^{14}$C nervonoyl-CoA. The reactions were run at 25° C. for 10 minutes.

The results of the wax synthase activity assay demonstrate that the protein encoded by the ATWS1 sequence (SEQ ID NO: 3) has wax synthase activity for all acyl-CoA and alcohol substrates tested (FIGS. 2, 3, 4, and 5). The wax synthase particularly has greater activity for longer chain substrates, particularly C20 and greater substrates.

13B. Plant Expression

To characterize the *Arabidopsis* sequence which is preferentially expressed in the developing seeds, constructs are prepared to direct the expression of the sequence in host plant cells.

A plasmid containing the napin cassette derived from pCGN3223 (described in U.S. Pat. No. 5,639,790, the entirety of which is incorporated herein by reference) was modified to make it more useful for cloning large DNA fragments containing multiple restriction sites, and to allow the cloning of multiple napin fusion genes into plant binary transformation vectors. An adapter comprised of the self annealed oligonucleotide of sequence 5'-CGCGATTTAAATGGCGCGCCCTGCAGGCGGCCGCCTGCAGGGCGCGCCATTTAAAT (SEQ ID NO:50) was ligated into the cloning vector pBC SK+ (Stratagene) after digestion with the restriction endonuclease BssHII to construct vector pCGN7765. Plasmids pCGN3223 and pCGN7765 were digested with NotI and ligated together. The resultant vector, pCGN7770, contains the pCGN7765 backbone with the napin seed specific expression cassette from pCGN3223.

The cloning cassette, pCGN7787, essentially the same regulatory elements as pCGN7770, with the exception of the napin regulatory regions of pCGN7770 have been replaced with the double CAMV 35S promoter and the tml polyadenylation and transcriptional termination region.

A binary vector for plant transformation, pCGN5139, was constructed from pCGN1558 (McBride and Summerfelt, (1990) Plant Molecular Biology, 14:269-276). The polylinker of pCGN1558 was replaced as a HindIII/Asp718 fragment with a polylinker containing unique restriction endonuclease sites, AscI, PacI, XbaI, SwaI, BamHI, and NotI. The Asp718 and HindIII restriction endonuclease sites are retained in pCGN5139.

A series of turbo binary vectors are constructed to allow for the rapid cloning of DNA sequences into binary vectors containing transcriptional initiation regions (promoters) and transcriptional termination regions.

The plasmid pCGN8618 was constructed by ligating oligonucleotides 5'-TCGAGGATCCGCGGCCGCAAGCTTCCTGCAGG-3' (SEQ ID NO:51) and 5'-TCGACCTGCAGGAAGCTTGCGGCCGCGGATCC-3' (SEQ ID NO:52) into SalI/XhoI-digested pCGN7770. A fragment containing the napin promoter, polylinker and napin 3' region was excised from pCGN8618 by digestion with Asp718I; the fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the napin promoter was closest to the blunted Asp718I site of pCGN5139 and the napin 3' was closest to the blunted HindIII site was subjected to sequence analysis to confirm both the insert orientation and the integrity of cloning junctions. The resulting plasmid was designated pCGN8622.

The plasmid pCGN8619 was constructed by ligating oligonucleotides 5'-TCGACCTGCAGGAAGCTTGCGGCCGCGGATCC-3' (SEQ ID NO:53) and 5'-TCGAGGATCCGCGGCCGCAAGCTTCCTGCAGG-3' (SEQ ID NO:54) into SalI/XhoI-digested pCGN7770. A fragment containing the napin promoter, polylinker and napin 3' region was removed from pCGN8619 by digestion with Asp718I; the fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the napin promoter was closest to the blunted Asp718I site of pCGN5139 and the napin 3' was closest to the blunted HindIII site was subjected to sequence analysis to confirm both the insert orientation and the integrity of cloning junctions. The resulting plasmid was designated pCGN8623.

The plasmid pCGN8620 was constructed by ligating oligonucleotides 5'-TCGAGGATCCGCGGCCGCAAGCTTCCTGCAGGAGCT-3' (SEQ ID NO:55) and 5'-CCTGCAGGAAGCTTGCGGCCGCGGATCC-3' (SEQ ID NO:56) into SalI/SacI-digested pCGN7787. A fragment containing the d35S promoter, polylinker and tml 3' region was removed from pCGN8620 by complete digestion with Asp718I and partial digestion with NotI. The fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the d35S promoter was closest to the blunted Asp718I site of pCGN5139 and the tml 3' was closest to the blunted HindIII site was subjected to sequence analysis to confirm both the insert orientation and the integrity of cloning junctions. The resulting plasmid was designated pCGN8624.

The plasmid pCGN8621 was constructed by ligating oligonucleotides 5'-TCGACCTGCAGGAAGCTTGCGGCCGCGGATCCAGCT-3' (SEQ ID NO:57) and 5'-GGATCCGCGGCCGCAAGCTTCCTGCAGG-3' (SEQ ID NO:58) into SalI/SacI-digested pCGN7787. A fragment containing the d35S promoter, polylinker and tml 3' region was removed from pCGN8621 by complete digestion with Asp718I and partial digestion with NotI. The fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the d35S promoter was closest to the blunted Asp718I site of pCGN5139 and the tml 3' was closest to the blunted HindIII site was subjected to sequence analysis to confirm both the insert orientation and the integrity of cloning junctions. The resulting plasmid was designated pCGN8625.

The open reading frame of AT-WS2 was PCR amplified from *Arabidopsis* genomic DNA using the primers 5'-GGATCCGCGGCCGCATTATGAAACAGTTAGCAACCAACAGA-3' (SEQ ID NO: 37) and 5'-GGATCCCCTGCAGGTTACATAAAATACAGACAACGTGCC-3' (SEQ ID NO: 38). The PCR product is cloned into plasmid pCR 2.1 according to the manufacturer's protocol (Clontech®) to generate the plasmid pCGN9706. To direct transcription of a sense transcript under control of a napin expression cassette in transgenic plants, plasmid pCGN9712 is constructed by cloning the NotI/Sse83871I fragment from pCGN9706 into NotI/PstI digested binary vector pCGN8622. To direct transcription of an antisense transcript under control of a napin expression cassette in transgenic plants, plasmid pCGN9713 was constructed by cloning the NotI/Sse83871 fragment from pCGN9706 into NotI/PstI digested binary vector pCGN8623. To direct transcription of a sense transcript under control of a double 35S expression cassette in transgenic plants, plasmid pCGN9714 was constructed by cloning the NotI/Sse83871 fragment from pCGN9706 into NotI/PstI digested binary vector pCGN8624. Plasmids pCGN9712, pCGN9713, and pCGN9714 were introduced into *Agrobacterium tumefaciens* EHA 105 by electroporation, and the resultant *Agrobacterium* strains were used to transform *Arabidopsis thaliana* plants by vacuum infiltration.

The open reading frame of the ATWS1 sequence (SEQ ID NO: 3) was amplified using PCR and cloned into pCGN8622, pCGN8623, and pCGN8624 to create the plant expression constructs pCGN9708, pCGN9709, and pCGN9710, respectively.

Example 14

Plant Transformation Methods and Analyses

A variety of methods have been developed to insert a DNA sequence of interest into the genome of a plant host to obtain the transcription or transcription and translation of the sequence to effect phenotypic changes.

High erucic acid varieties, such as cultivar Reston, or Canola-type varieties of *Brassica napus* may be transformed using *Agrobacterium* mediated transformation methods as described by Radke et al. (*Theor. Appl. Genet.* (1988) 75:685-694; *Plant Cell Reports* (1992) 11:499-505). Transgenic *Arabidopsis thaliana* plants may be obtained by *Agrobacterium*-mediated transformation as described by Valverkens et al., (*Proc. Nat. Acad. Sci.* (1988) 85:5536-5540), or as described by Bent et al. ((1994), *Science* 265:1856-1860), or Bechtold et al. ((1993), *C. R. Acad. Sci, Life Sciences* 316:1194-1199). Other plant species may be similarly transformed using related techniques.

Alternatively, microprojectile bombardment methods, such as described by Klein et al. (*Bio/Technology* 10:286-291) may also be used to obtain transformed plants comprising the reductase and wax synthase expression constructs described herein.

Seed oils obtained from transgenic *Arabidopsis* plants expressing ATWS1 (SEQ ID NO: 3) (pCGN9708) or ATWS2 (SEQ ID NO: 5)(pCGN9712) from the napin promoter are analyzed for triglyceride production by thin layer chromatography (TLC) and fatty acid methyl ester (FAME) analysis using methods described above.

Results of the analyses demonstrate that lines expressing the ATWS1 sequence (SEQ ID NO: 3) have a reduced amount of triglycerides as well as a reduced amount of total fatty acids. Lines 9708-AT001-7 and 9708-AT001-23 contained 27.34% and 24.85% FAME by dry weight compared to non-transformed *Arabidopsis* seed, which contain approximately 34% FAME. In addition, lines expressing ATWS2 (SEQ ID NO: 5) have about 31% FAME (FIG. 6).

The above results demonstrate nucleic acid sequences obtained from partially purified wax synthase proteins are active in the formation of wax esters from fatty alcohol and fatty acyl substrates. Methods to obtain the wax synthase proteins and amino acid sequences thereof are provided. Such nucleic acid sequences may be manipulated to provide for transcription of the sequences and/or expression of wax synthase proteins in host cells, which proteins may be used for a variety of applications. Such applications include the production of wax ester compounds when the wax synthase is used in host cells having a source of fatty alcohol substrates, which substrates may be native to the host cells or supplied by use of recombinant constructs encoding a fatty acyl reductase protein which is active in the formation of alcohols from fatty acyl substrates.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teaching of this invention that certain changes and modifications may be made thereto without departing from the spirit or scope of the appended claims.

What is claimed is:

1. A method of producing a wax ester in a host cell comprising the steps of growing a host cell having a recombinant nucleic acid construct comprising a promoter functional in said host cell and a nucleic acid sequence encoding a wax synthase, wherein the amino acid sequence of said wax synthase is SEQ ID NO: 2 and said host cell comprises an endogenous fatty acyl-CoA reductase and a β-ketoacyl-CoA synthase;

and obtaining expression of said nucleic acid encoding said wax synthase, wherein said host cell comprises a fatty alcohol substrate of said wax synthase, and said wax ester is produced in said host cell.

2. The method according to claim 1, wherein said wax ester is produced from a fatty alcohol and a fatty-CoA substrate.

3. The method according to claim 1, wherein said host cell is selected from the group consisting of a bacterial cell, an insect cell, and a plant cell.

4. The method according to claim 1, wherein said promoter is functional in a plant cell.

5. The method according to claim 4, wherein said promoter is preferentially expressed in a specific plant tissue.

6. The method according to claim 5, wherein said promoter is preferentially expressed in a plant seed cell.

7. The method according to claim 1, wherein the triglyceride content of said cell is reduced.

8. The method according to claim 1, wherein said β-ketoacyl-CoA synthase is recombinant and under the regulatory control of a promoter functional in said host cell.

9. The method according to claim 8, wherein the triglyceride content of said cell is reduced.

10. A method for altering the oil content of a host cell comprising growing a host cell having a recombinant nucleic acid construct comprising a promoter functional in said host cell and a nucleic acid sequence encoding an a wax synthase, wherein the amino acid sequence of said wax synthase is SEQ ID NO: 2 and said host cell comprises an endogenous fatty acyl-CoA reductase and a β-ketoacyl-CoA synthase;

and obtaining expression of said nucleic acid encoding said wax synthase.

11. The method according to claim 10, wherein said host cell is selected from the group consisting of a bacterial cell, an insect cell, and a plant cell.

12. The method according to claim 10, wherein the triglyceride content of said cell is reduced.

13. The method according to claim 10, wherein the content of very long chain fatty acids is increased.

* * * * *

SEQUENCE LISTING

```
<160> NUMBER OF SEQ ID NOS: 61

<210> SEQ ID NO 1
<211> LENGTH: 1335
<212> TYPE: DNA
<213> ORGANISM: Simmondsia chinensis

<400> SEQUENCE: 1
gtctccatta caatggaggt ggagaaggag ctaaagacct tctcagaggt atggatctcc      60
gccatagccg ccgcctgcta ctgccgcttc gtcccgccg ttgcccctca cggcggcgct     120
ctccgcctcc tcctcctcct ccccgtcgtc ctcctcttca ttttcctccc cctccgcctc     180
tcctccttcc acctcggcgg gcccaccgcc ttgtatctcg tctggcttgc caacttcaag     240
ctccttctct tcgcctttca tcttggccct ttatctaacc cctctctctc tctccttcac     300
ttcatctcca ccacctcct ccccatcaag ttcagagatg acccatctaa tgatcatgag      360
aaaaacaaga gaactctgag ttttgagtgg cgtaaagttg ttcttttgt tgctaagttg     420 gtgtttttg cgggtatttt aaagatttat gagtttagaa aagatttgcc tcattttgtg     480
atctcggtgc tttactgttt tcacttctat ctcgggacgg agatcacctt agcagcaagc     540
gcagtcatag ctcgagccac gctagggtta gacctatacc cccagttcaa cgagccatac     600
```

```
ttagccacct cgctgcaaga cttctggggg cgcaggtgga acctcatggt gtcagacatc    660
ttggggttga caacatacca gcctgtccgg cgtgtcctct cgaggtgggt caggctgcgg    720
tgggaggtcg ccggcgcaat gttggtggcg ttcacggtgt cggggctaat gcatgaagtg    780
tttttcttct acttaactcg cgcgaggccc tcgtgggagg tgacggggtt ctttgtgttg    840 catgggttt gcacagccgt ggagatggtg gtgaagaagg cggtttcagg caaggtgcgg     900
ctgcgccggg aggtgtcagg ggcgctgacg gtggggttcg tgatggtgac tggagggtgg    960 ttgttttgc cgcagctggt gaggcatggg gtagatttga agaccattga tgagtatcct    1020
gtcatgttta attatactca gaagaaattg atgggtttgt tggggtggtg atgaatgatg    1080
agatgatgat catgcatctt cttttcgga gatcggttgt acgtcacgag gagaacccat     1140
gaaaaatgca gatcaracgg caagacaggt cgggaaaaaa aaatgatcaa ttttccctta    1200
agtagccggc ctgccaccct gtccgattgt ggcattttg tggtcacttt ttcatatcgt     1260
gtagtatttt tggttttttg tttttaatgt tttctatgaa ttttgaataa tttgtgcttc    1320
atgaaaattt ttttt                                                   1335
```

<210> SEQ ID NO 2
<211> LENGTH: 352
<212> TYPE: PRT
<213> ORGANISM: Simmondsia chinensis

<400> SEQUENCE: 2

```
Met Glu Val Glu Lys Glu Leu Lys Thr Phe Ser Glu Val Trp Ile Ser
 1               5                  10                  15

Ala Ile Ala Ala Ala Cys Tyr Cys Arg Phe Val Pro Ala Val Ala Pro
            20                  25                  30

His Gly Gly Ala Leu Arg Leu Leu Leu Leu Pro Val Val Leu Leu
        35                  40                  45

Phe Ile Phe Leu Pro Leu Arg Leu Ser Ser Phe His Leu Gly Gly Pro
    50                  55                  60

Thr Ala Leu Tyr Leu Val Trp Leu Ala Asn Phe Lys Leu Leu Leu Phe
65                  70                  75                  80

Ala Phe His Leu Gly Pro Leu Ser Asn Pro Ser Leu Ser Leu His
            85                  90                  95

Phe Ile Ser Thr Thr Leu Leu Pro Ile Lys Phe Arg Asp Asp Pro Ser
           100                 105                 110

Asn Asp His Glu Lys Asn Lys Arg Thr Leu Ser Phe Glu Trp Arg Lys
       115                 120                 125

Val Val Leu Phe Val Ala Lys Leu Val Phe Phe Ala Gly Ile Leu Lys
   130                 135                 140

Ile Tyr Glu Phe Arg Lys Asp Leu Pro His Phe Val Ile Ser Val Leu
145                 150                 155                 160

Tyr Cys Phe His Phe Tyr Leu Gly Thr Glu Ile Thr Leu Ala Ala Ser
               165                 170                 175

Ala Val Ile Ala Arg Ala Thr Leu Gly Leu Asp Leu Tyr Pro Gln Phe
           180                 185                 190

Asn Glu Pro Tyr Leu Ala Thr Ser Leu Gln Asp Phe Trp Gly Arg Arg
       195                 200                 205

Trp Asn Leu Met Val Ser Asp Ile Leu Gly Leu Thr Thr Tyr Gln Pro
   210                 215                 220

Val Arg Arg Val Leu Ser Arg Trp Val Arg Leu Arg Trp Glu Val Ala
225                 230                 235                 240
```

```
Gly Ala Met Leu Val Ala Phe Thr Val Ser Gly Leu Met His Glu Val
                245                 250                 255
Phe Phe Phe Tyr Leu Thr Arg Ala Arg Pro Ser Trp Glu Val Thr Gly
            260                 265                 270
Phe Phe Val Leu His Gly Val Cys Thr Ala Val Glu Met Val Val Lys
        275                 280                 285
Lys Ala Val Ser Gly Lys Val Arg Leu Arg Arg Glu Val Ser Gly Ala
    290                 295                 300
Leu Thr Val Gly Phe Val Met Val Thr Gly Gly Trp Leu Phe Leu Pro
305                 310                 315                 320
Gln Leu Val Arg His Gly Val Asp Leu Lys Thr Ile Asp Glu Tyr Pro
                325                 330                 335
Val Met Phe Asn Tyr Thr Gln Lys Lys Leu Met Gly Leu Leu Gly Trp
            340                 345                 350

<210> SEQ ID NO 3
<211> LENGTH: 1026
<212> TYPE: DNA
<213> ORGANISM: Arabidopsis sp

<400> SEQUENCE: 3
atggaagaaa agtttagaaa cttaatcgag gtatggatct ctgctttaat ctctctatct      60
tactgttatt acatatcgtc taaactctcc aaaggtgttc ttcgtctcct ctctattctt     120
ccagtctgca ttctgtttct tgttcttcct ctgttcctct cttgtgtgca cttttgcgcc     180
atttcagttc tttttctttc atggcttgca aactttaagc ttcttctatt tgcctttgat     240
gagggacctt tgttcccact tcctccaaaa ctctcccgtt tcatctgctt cgcttgttta     300
cccatcaaaa tcagacaaga cccttctcca aatgcgatac aaatcttca tcctaaacct      360
atgcctaaat gggttttggc tgttaaaatt ttggtcttgg gcgtcttgtt acatgtttat     420
gaatacaggg atggtttgcc tcggtttgtt gtcttggctc tctattgtct ccatatttac     480
cttgaggtag aacttgtctt ggtctttgtt ggagccgtgg tatctactct tcttgggtgt     540
aacatcgagc cggtgttcaa tgagccctac ctagctacct ccctacaaga cttctggagc     600
cgcagatgga acctcatggt ttcagccgtc ctacgctcaa ccgttcacat tccggttcag     660
cgttttttca aacgcatact cagtccagac ggggctatgt ttgctggggt catggcatcg     720
ttctttgtct caggcttgat gcatgagctg ctctactttt acatgatccg taagcctcca     780
acttgggaag tcacttgttt ctttgtgttg catggtgctg ccactgccac tgagatagcg     840
gtgaagagaa cacaatggtt gaggccaccg caccgggctg tctctggtct tgtagttctg     900
acgtttgtga gtgtgacggg cgtttggcta ttcctcgctc aagtgctgag aaacaatgtc     960
catgagaaag cgattggaga atgtttattg gttcttgacc tagccaagtt attcacttct    1020
tcatga                                                              1026

<210> SEQ ID NO 4
<211> LENGTH: 341
<212> TYPE: PRT
<213> ORGANISM: Arabidopsis sp

<400> SEQUENCE: 4

Met Glu Glu Lys Phe Arg Asn Leu Ile Glu Val Trp Ile Ser Ala Leu
1               5                   10                  15
Ile Ser Leu Ser Tyr Cys Tyr Tyr Ile Ser Ser Lys Leu Ser Lys Gly
            20                  25                  30
```

```
Val Leu Arg Leu Leu Ser Ile Leu Pro Val Cys Ile Leu Phe Leu Val
            35                  40                  45
Leu Pro Leu Phe Leu Ser Cys Val His Phe Cys Ala Ile Ser Val Leu
         50                  55                  60
Phe Leu Ser Trp Leu Ala Asn Phe Lys Leu Leu Phe Ala Phe Asp
 65                  70                  75                  80
Glu Gly Pro Leu Phe Pro Leu Pro Pro Lys Leu Ser Arg Phe Ile Cys
                 85                  90                  95
Phe Ala Cys Leu Pro Ile Lys Ile Arg Gln Asp Pro Ser Pro Asn Ala
            100                 105                 110
Ile Pro Asn Leu His Pro Lys Pro Met Pro Lys Trp Val Leu Ala Val
            115                 120                 125
Lys Ile Leu Val Leu Gly Val Leu Leu His Val Tyr Glu Tyr Arg Asp
        130                 135                 140
Gly Leu Pro Arg Phe Val Val Leu Ala Leu Tyr Cys Leu His Ile Tyr
145                 150                 155                 160
Leu Glu Val Glu Leu Val Leu Val Phe Val Gly Ala Val Val Ser Thr
                165                 170                 175
Leu Leu Gly Cys Asn Ile Glu Pro Val Phe Asn Glu Pro Tyr Leu Ala
            180                 185                 190
Thr Ser Leu Gln Asp Phe Trp Ser Arg Arg Trp Asn Leu Met Val Ser
        195                 200                 205
Ala Val Leu Arg Ser Thr Val His Ile Pro Val Gln Arg Phe Phe Lys
210                 215                 220
Arg Ile Leu Ser Pro Asp Gly Ala Met Phe Ala Gly Val Met Ala Ser
225                 230                 235                 240
Phe Phe Val Ser Gly Leu Met His Glu Leu Leu Tyr Phe Tyr Met Ile
                245                 250                 255
Arg Lys Pro Pro Thr Trp Glu Val Thr Cys Phe Phe Val Leu His Gly
            260                 265                 270
Ala Ala Thr Ala Thr Glu Ile Ala Val Lys Arg Thr Gln Trp Leu Arg
        275                 280                 285
Pro Pro His Arg Ala Val Ser Gly Leu Val Val Leu Thr Phe Val Ser
290                 295                 300
Val Thr Gly Val Trp Leu Phe Leu Ala Gln Val Leu Arg Asn Asn Val
305                 310                 315                 320
His Glu Lys Ala Ile Gly Glu Cys Leu Leu Val Leu Asp Leu Ala Lys
                325                 330                 335
Leu Phe Thr Ser Ser
            340

<210> SEQ ID NO 5
<211> LENGTH: 1071
<212> TYPE: DNA
<213> ORGANISM: Arabidopsis sp

<400> SEQUENCE: 5
atgaaacagt tagcaaccaa cagaaccaag agagaaaaga tggaagaaga gttgagaaac      60
ctaatcaagg tttggatctc tgccttaatc tccatatctt actgttacta catctcatca     120
aaaatctcca aggtgttct tcgtctcctc tctcttcttc ccatcttcat catctttctt      180
cttcttcctc tcttcttctc ttctgtccac ttctgcgtca tctcaggttt cttcttcaca     240
tggctcgcaa atttcaagct ctttctcttt gctttcgatc aagaaccttt aagcccactt     300
```

```
ccctcaaatc tcacccgttt cttctgcttc gcttgtttcc ccatcaaaat caataaaaac    360
ccttcttcaa atcgaatcca caacaaacct atgtctaaat gggtccttgc tttcaaactt    420
ttgatctttt ccttcttatt acatgtgtat agaaacaact atgattccgg tttatcacgg    480
ttcgctttct tggctctctt taccattcat gtttacctcg aggcagaact tatcttagtc    540
ttcgtcggtg ccttgatgtc tatgcttctt ggttgtgaaa tggaaccggt attcaatgat    600
ccttacttag ccacttcttt acaagagttt tggagccgta gatggaacct catggtccca    660
gccgtactcc gtccagccgt ccacataccg gttcagcgat tttgtgcacc gttactcggt    720
ctacaccggg cttttacgc tggaatgtta gccacgttta ttgtctctgg tttaatgcat    780
gagctgattt actttatgt tatccgcaaa tctccaactt gggaagtcac ttgcttcttt    840
cttttgcatg gagttgtaac ttgcctagag atagcgatga agaggatgcg gtggcttcct    900
acgccacgtc gggcggtctc gggtcttgca attacggtgt ttttgctcgt tacagctggt    960
tggttgtttt accctcaaat gttaagaaat gatgtgcata agagagtgat aagtgaatgt   1020
ttgttggtta ttgacgttgt taaaaggcac gttgtctgta ttttaatgta a           1071

<210> SEQ ID NO 6
<211> LENGTH: 356
<212> TYPE: PRT
<213> ORGANISM: Arabidopsis sp

<400> SEQUENCE: 6

Met Lys Gln Leu Ala Thr Asn Arg Thr Lys Arg Glu Lys Met Glu Glu
 1               5                  10                  15

Glu Leu Arg Asn Leu Ile Lys Val Trp Ile Ser Ala Leu Ile Ser Ile
                20                  25                  30

Ser Tyr Cys Tyr Tyr Ile Ser Ser Lys Ile Ser Lys Gly Val Leu Arg
            35                  40                  45

Leu Leu Ser Leu Leu Pro Ile Phe Ile Ile Phe Leu Leu Leu Pro Leu
        50                  55                  60

Phe Phe Ser Ser Val His Phe Cys Val Ile Ser Gly Phe Phe Phe Thr
65                  70                  75                  80

Trp Leu Ala Asn Phe Lys Leu Phe Leu Phe Ala Phe Asp Gln Glu Pro
                85                  90                  95

Leu Ser Pro Leu Pro Ser Asn Leu Thr Arg Phe Cys Phe Ala Cys
            100                 105                 110

Phe Pro Ile Lys Ile Asn Lys Asn Pro Ser Ser Asn Arg Ile His Asn
        115                 120                 125

Lys Pro Met Ser Lys Trp Val Leu Ala Phe Lys Leu Leu Ile Phe Ser
    130                 135                 140

Phe Leu Leu His Val Tyr Arg Asn Asn Tyr Asp Ser Gly Leu Ser Arg
145                 150                 155                 160

Phe Ala Phe Leu Ala Leu Phe Thr Ile His Val Tyr Leu Glu Ala Glu
                165                 170                 175

Leu Ile Leu Val Phe Val Gly Ala Leu Met Ser Met Leu Leu Gly Cys
            180                 185                 190

Glu Met Glu Pro Val Phe Asn Asp Pro Tyr Leu Ala Thr Ser Leu Gln
        195                 200                 205

Glu Phe Trp Ser Arg Arg Trp Asn Leu Met Val Pro Ala Val Leu Arg
    210                 215                 220

Pro Ala Val His Ile Pro Val Gln Arg Phe Cys Ala Pro Leu Leu Gly
225                 230                 235                 240
```

```
Leu His Arg Ala Phe Tyr Ala Gly Met Leu Ala Thr Phe Ile Val Ser
            245                 250                 255

Gly Leu Met His Glu Leu Ile Tyr Phe Tyr Val Ile Arg Lys Ser Pro
            260                 265                 270

Thr Trp Glu Val Thr Cys Phe Phe Leu Leu His Gly Val Val Thr Cys
        275                 280                 285

Leu Glu Ile Ala Met Lys Arg Met Arg Trp Leu Pro Thr Pro Arg Arg
    290                 295                 300

Ala Val Ser Gly Leu Ala Ile Thr Val Phe Leu Leu Val Thr Ala Gly
305                 310                 315                 320

Trp Leu Phe Tyr Pro Gln Met Leu Arg Asn Asp Val His Lys Arg Val
                325                 330                 335

Ile Ser Glu Cys Leu Leu Val Ile Asp Val Val Lys Arg His Val Val
            340                 345                 350

Cys Ile Leu Met
            355

<210> SEQ ID NO 7
<211> LENGTH: 1029
<212> TYPE: DNA
<213> ORGANISM: Arabidopsis sp

<400> SEQUENCE: 7
atggaagaag aactcaagaa cttcatcaag ctttggattt cagcaataat ctccatatct      60
tactgttact acttatcaac aggaatcaaa gctggtgttt ttcgattact ctctgttctt     120
cctgtatgtg ctctgtttct tgtttttcct ctgtttttct cctatgttca cttctctggt     180
tgcatggctt ttttcctctc atggctcgca aatttcaaac tcatcctctt ctccttcgat     240
caaggtcctc tttccccact tcctcgaact ctctcccgat tcatatgcat cacttgcttc     300
cccatcaagc tcaacaaaaa ccctaatatt caaaattata aaatccccat atggcttttc     360
gccattaaag ttgtcatctt tgttgtcttg ttacaaatgt atgaatacaa acaatatctg     420
tctccggctt tattattggt ttttaattct ctacatatat tcttggagct tgagattgtc     480
tttatgctcg tcaaagcatt ggtctttatc actcttggct gcgatctaga gccacagtcc     540
aatgaaccat acttagccac ttctcttcaa gacttctggg gtcgtcggtg aacctcatg     600
gtcccggcga ttctccggcc ggctgtctac ctcccggcga gacgaatggc ctgtcggaaa     660
gttaactccg atcaggctat gttcttggga gttttcgcag cgtttctcgt ctccggtgcg     720
gttcatgaga tgctcttctt ctatcttacc cgtgaggttc ctacagggga agtcacttgg     780
ttcttttttgt tacatggagt ttgcacggtg gcggaagtgg cggtgaagaa gagtacattt     840
gtgcggcgat ggtggagagt gagtccgacg gtgtcacgtc ttctgacggt cggttttgtt     900
gttgtgacga gtggttggtt cttttttccct cttataagga gtggcatcat cgaaagactc     960
gctagcgaag cctaatgtg cattgatttc gtcaagcaca gtttcttct gttactttg    1020
ggtgattaa                                                         1029

<210> SEQ ID NO 8
<211> LENGTH: 342
<212> TYPE: PRT
<213> ORGANISM: Arabidopsis sp

<400> SEQUENCE: 8

Met Glu Glu Glu Leu Lys Asn Phe Ile Lys Leu Trp Ile Ser Ala Ile
1               5                   10                  15
```

Ile Ser Ile Ser Tyr Cys Tyr Tyr Leu Ser Thr Gly Ile Lys Ala Gly
            20                  25                  30

Val Phe Arg Leu Leu Ser Val Leu Pro Val Cys Ala Leu Phe Leu Val
        35                  40                  45

Phe Pro Leu Phe Phe Ser Tyr Val His Phe Ser Gly Cys Met Ala Phe
    50                  55                  60

Phe Leu Ser Trp Leu Ala Asn Phe Lys Leu Ile Leu Phe Ser Phe Asp
65                  70                  75                  80

Gln Gly Pro Leu Ser Pro Leu Pro Arg Thr Leu Ser Arg Phe Ile Cys
                85                  90                  95

Ile Thr Cys Phe Pro Ile Lys Pro Gln Gln Asn Pro Asn Ile Gln Asn
            100                 105                 110

Tyr Lys Ile Pro Ile Trp Leu Phe Ala Ile Lys Val Val Ile Phe Val
        115                 120                 125

Val Leu Leu Gln Met Tyr Glu Tyr Lys Gln Tyr Leu Ser Pro Ala Leu
    130                 135                 140

Leu Leu Val Phe Asn Ser Leu His Ile Phe Leu Glu Leu Glu Ile Val
145                 150                 155                 160

Phe Met Leu Val Lys Ala Leu Val Phe Ile Thr Leu Gly Cys Asp Leu
                165                 170                 175

Glu Pro Gln Ser Asn Glu Pro Tyr Leu Ala Thr Ser Leu Gln Asp Phe
            180                 185                 190

Trp Gly Arg Arg Trp Asn Leu Met Val Pro Ala Ile Leu Arg Pro Ala
        195                 200                 205

Val Tyr Leu Pro Ala Arg Arg Met Ala Cys Arg Lys Val Asn Ser Asp
    210                 215                 220

Gln Ala Met Phe Leu Gly Val Phe Ala Ala Phe Leu Val Ser Gly Ala
225                 230                 235                 240

Val His Glu Met Leu Phe Phe Tyr Leu Thr Arg Glu Val Pro Thr Gly
                245                 250                 255

Glu Val Thr Trp Phe Phe Leu Leu His Gly Val Cys Thr Val Ala Glu
            260                 265                 270

Val Ala Val Lys Lys Ser Thr Phe Val Arg Arg Trp Arg Val Ser
        275                 280                 285

Pro Thr Val Ser Arg Leu Leu Thr Val Gly Phe Val Val Val Thr Ser
    290                 295                 300

Gly Trp Phe Phe Phe Pro Leu Ile Arg Ser Gly Ile Ile Glu Arg Leu
305                 310                 315                 320

Ala Ser Glu Ala Leu Met Cys Ile Asp Phe Val Lys His Lys Phe Leu
                325                 330                 335

Leu Leu Leu Leu Gly Asp
            340

<210> SEQ ID NO 9
<211> LENGTH: 1038
<212> TYPE: DNA
<213> ORGANISM: Arabidopsis sp

<400> SEQUENCE: 9
atggaggaag aactcatgag cttaatcaaa gtatgggttt atgcaataat ctccatatct      60
tactgttact acacatcaac aagaatcaaa tctggtgttt tcgattact atctgttctt      120 cctgtttgtg ttctgtttct tgttctccct ctgtttgttt cctctgttca cttttctggt     180
tccacagcat ttttcctctc atggcttgcc aatttcaaac taatcctctt ctccttcgac      240

```
caaggtccac ttttcccagt tccctcaaat ctctcccgat tcgtctgctt cacttgcttc    300
cccatcaagc ttcaacaaaa ccctaaacct caaaatcaaa tgcctaaatg gggtttcgca    360
gttaaacttg ccttctttgg tgtgttgttg catatgtatg aatacaaaca acatatgtct    420
ccgactgttc tattggttct ctattctctg catatatact tggagtatga gattctctta    480
gctcccttga agttctgct tagtatctct ctttggtgcg acctcgagcc gcatttcaat    540
gaaccatact tatccacctc tcttcaagac ttctggggtc gtcgatggaa cctcatggtc    600
ccggcgattc tccggccggc tgtctacctc ccggtgcgac aaatggccgg tcggaaaatg    660
aactctgatc aggctttgtt cttgggagtt tttgcctcgt tccttgtttc cggtgtggtt    720
cacgagctta ttttcttcta ttttacacgt gaatcgccga caggtgaagt cactttgttc    780
tttgtattac atggagtttg cactgccgct gaatgcgctg cgaagaggac gaggttggtg    840
cggcgatgga aggtgagtca gatggtttca cgactgctca cggtgggatt tgttgttatg    900
accggtggtt ggttgttttt ccctcacctt gcaaggagtg gcatgatcga gagactagct    960
gacgaagcct ttttgtttat tggtttcgtc aagcacaagt ttttctacct ttgtagaaac   1020
caatcgctaa aatcgtag                                                 1038
```

<210> SEQ ID NO 10
<211> LENGTH: 345
<212> TYPE: PRT
<213> ORGANISM: Arabidopsis sp

<400> SEQUENCE: 10

```
Met Glu Glu Glu Leu Met Ser Leu Ile Lys Val Trp Val Tyr Ala Ile
1               5                   10                  15

Ile Ser Ile Ser Tyr Cys Tyr Tyr Thr Ser Thr Arg Ile Lys Ser Gly
            20                  25                  30

Val Phe Arg Leu Leu Ser Val Leu Pro Val Cys Val Leu Phe Leu Val
        35                  40                  45

Leu Pro Leu Phe Val Ser Ser Val His Phe Ser Gly Ser Thr Ala Phe
    50                  55                  60

Phe Leu Ser Trp Leu Ala Asn Phe Lys Leu Ile Leu Phe Ser Phe Asp
65                  70                  75                  80

Gln Gly Pro Leu Phe Pro Val Pro Ser Asn Leu Ser Arg Phe Val Cys
                85                  90                  95

Phe Thr Cys Phe Pro Ile Lys Leu Gln Gln Asn Pro Lys Pro Gln Asn
            100                 105                 110

Gln Met Pro Lys Trp Gly Phe Ala Val Lys Leu Ala Phe Phe Gly Val
        115                 120                 125

Leu Leu His Met Tyr Glu Tyr Lys Gln His Met Ser Pro Thr Val Leu
    130                 135                 140

Leu Val Leu Tyr Ser Leu His Ile Tyr Leu Glu Tyr Glu Ile Leu Leu
145                 150                 155                 160

Ala Pro Leu Lys Val Leu Leu Ser Ile Ser Leu Trp Cys Asp Leu Glu
                165                 170                 175

Pro His Phe Asn Glu Pro Tyr Leu Ser Thr Ser Leu Gln Asp Phe Trp
            180                 185                 190

Gly Arg Arg Trp Asn Leu Met Val Pro Ala Ile Leu Arg Pro Ala Val
        195                 200                 205

Tyr Leu Pro Val Arg Gln Met Ala Gly Arg Lys Met Asn Ser Asp Gln
    210                 215                 220

Ala Leu Phe Leu Gly Val Phe Ala Ser Phe Leu Val Ser Gly Val Val
```

```
            225                 230                 235                 240

His Glu Leu Ile Phe Phe Tyr Phe Thr Arg Glu Ser Pro Thr Gly Glu
                245                 250                 255

Val Thr Leu Phe Phe Val Leu His Gly Val Cys Thr Ala Ala Glu Cys
            260                 265                 270

Ala Ala Lys Arg Thr Arg Leu Val Arg Arg Trp Lys Val Ser Gln Met
        275                 280                 285

Val Ser Arg Leu Leu Thr Val Gly Phe Val Val Met Thr Gly Gly Trp
    290                 295                 300

Leu Phe Phe Pro His Leu Ala Arg Ser Gly Met Ile Glu Arg Leu Ala
305                 310                 315                 320

Asp Glu Ala Phe Leu Phe Ile Gly Phe Val Lys His Lys Phe Phe Tyr
                325                 330                 335

Leu Cys Arg Asn Gln Ser Leu Lys Ser
            340                 345

<210> SEQ ID NO 11
<211> LENGTH: 1002
<212> TYPE: DNA
<213> ORGANISM: Arabidopsis sp

<400> SEQUENCE: 11
atggatgaag aactcaagaa cttgatcaaa gtatgggttt ctgcaataat ctcgatatct      60
tattgttact acataccacc tagaatcaaa tctggtgctc ctcgattcct ctctgtttcc     120
cctgttcttg ctctgtttct tgttcttcct ctgttttttct cctctctgca tttatcttta     180
atcacagcgt ttttcctcac atggcttgct aatttcaaac tcatcctctt ctccttcgat     240
aaaggtcctt aatcccaat tccaacaaat ttccctcgat tcttctgctt cacttgcttc     300
cccatcaagg ttcagcaaaa ccctaaatct caaaaccatt tgcccaaatt ggttttcgcc     360
attaaacttg caatctttgc agtgctatta catttgtata gctacagaca aaatctgtct     420
ccgactatac tattaggtct ctattttgtg catctctact tagagattga gattatatta     480
acgtttgtta agttgttgt ttttatctct cttggctgcg atcttgagcc acagtccaat     540
aaaccgtact agccacatc tctacaagac ttctggggtc gccggtggaa tctcatggtt     600
ccggcgattc tccggccagc cgtttacgca ccaatgcggc gagtctctga acgcaaaatg     660
agttccggtt gggctctgtt tccggggatt ttggcagcgt ttatcgtctc cggtttggtt     720
cacgaattgc tcttcttcta tttgatacgt gagatgccta caggagaagt tactctgttc     780
tttgtgttac atggcgtttg tactgctgta gaattggcgg tgaagaagaa aacgacggta     840
gcacagcggt ggcggttgag tccggggtg tcgcgggttc tcacggtggg gtttgtgttt     900
gtgactggtg gttggttgtt tacacctcag cttaaaagga gcggggtgat ggagagattc     960
acatctgaag ctgtgttgct cgttgagttc attaagcgat aa                      1002

<210> SEQ ID NO 12
<211> LENGTH: 333
<212> TYPE: PRT
<213> ORGANISM: Arabidopsis sp

<400> SEQUENCE: 12

Met Asp Glu Glu Leu Lys Asn Leu Ile Lys Val Trp Val Ser Ala Ile
1               5                   10                  15

Ile Ser Ile Ser Tyr Cys Tyr Tyr Ile Pro Pro Arg Ile Lys Ser Gly
            20                  25                  30
```

```
Ala Pro Arg Phe Leu Ser Val Ser Pro Val Leu Ala Leu Phe Leu Val
        35                  40                  45

Leu Pro Leu Phe Phe Ser Ser Leu His Leu Ser Leu Ile Thr Ala Phe
 50                  55                  60

Phe Leu Thr Trp Leu Ala Asn Phe Lys Leu Ile Leu Phe Ser Phe Asp
 65                  70                  75                  80

Lys Gly Pro Leu Ile Pro Ile Pro Thr Asn Phe Pro Arg Phe Cys
                 85                  90                  95

Phe Thr Cys Phe Pro Ile Lys Val Gln Gln Asn Pro Lys Ser Gln Asn
                100                 105                 110

His Leu Pro Lys Leu Val Phe Ala Ile Lys Leu Ala Ile Phe Ala Val
                115                 120                 125

Leu Leu His Leu Tyr Ser Tyr Arg Gln Asn Leu Ser Pro Thr Ile Leu
    130                 135                 140

Leu Gly Leu Tyr Phe Val His Leu Tyr Leu Glu Ile Glu Ile Leu
145                 150                 155                 160

Thr Phe Val Lys Val Val Phe Ile Ser Leu Gly Cys Asp Leu Glu
                165                 170                 175

Pro Gln Ser Asn Lys Pro Tyr Leu Ala Thr Ser Leu Gln Asp Phe Trp
                180                 185                 190

Gly Arg Arg Trp Asn Leu Met Val Pro Ala Ile Leu Arg Pro Ala Val
                195                 200                 205

Tyr Ala Pro Met Arg Arg Val Ser Glu Arg Lys Met Ser Ser Gly Trp
    210                 215                 220

Ala Leu Phe Pro Gly Ile Leu Ala Ala Phe Ile Val Ser Gly Leu Val
225                 230                 235                 240

His Glu Leu Leu Phe Pro Tyr Leu Ile Arg Glu Met Pro Thr Gly Glu
                245                 250                 255

Val Thr Leu Phe Phe Val Leu His Gly Val Cys Thr Ala Val Glu Leu
                260                 265                 270

Ala Val Lys Lys Lys Thr Thr Val Ala Gln Arg Trp Arg Leu Ser Pro
    275                 280                 285

Gly Val Ser Arg Val Leu Thr Val Gly Phe Val Phe Val Thr Gly Gly
    290                 295                 300

Trp Leu Phe Thr Pro Gln Leu Lys Arg Ser Gly Val Met Glu Arg Phe
305                 310                 315                 320

Thr Ser Glu Ala Val Leu Leu Val Glu Phe Ile Lys Arg
                325                 330

<210> SEQ ID NO 13
<211> LENGTH: 1041
<212> TYPE: DNA
<213> ORGANISM: Arabidopsis sp

<400> SEQUENCE: 13
atggaggaag aactcaagtt attcatccaa gtatgggttt ctgcaatcat ttcagtaact      60
tattgttact acttaacacc caaaatcaaa accagtcttc ttcgattact atctgttctt     120
cctgtttgtg ttttgtttct tattattcct atctttttct ccactgttca ttcctctttc     180
actattgcat ttttcctctc aggtcttgca gttccaaaac tcatcctctt tgcattagaa     240
aaaggtcctc tttttccact tcctcctaat ctccctcatt tcgtctgctt tgcttgcttc     300
cccatcaagc ttcaaaaaaa acctaaccct gaaaatacta accatttccc caaatgggtt     360
tttgccctga agttttcat ctttggtgcc ttgttactac aagcgtatca ttacaaacaa      420
```

-continued

```
tttctatcta cgaattttct attgggtctc tatgctctgc atatatactt ggagcttgag    480
atttccttaa ccttgataaa atttctcgtc agtatcactc ttgggtgtga cctcgagcca    540
caattcaacg aaccatactt agccacctct ctacatgact tctggggtca ccgatggaac    600
ctcatggtct cgaagattct ctggctcgca gtgtacaacc ccatacggca atggcgagcc    660
aagagctccg agtgggatcg gttcttcgcg attttcgcca cgttcctcgt ctctggtgtg    720
gctcacgaga ttctctactt ctatttgaca cgtgagaagc ctacatggga ggtgacttgg    780
ttctttgtgt acatgggtt ttgcatggcg gctgaagtgg cactgaagag aagacgaag     840 ttggtgcagc ggtggccggt gaatccggca gtgtcgagac tgcttacggt ggggtttgtg    900
tttgtgactg gtgtttggct attttccccc cagcctatta ggcacggctt gatggagagg    960
ttcatcaatg aagacttgtt tctaattgat ttctttaatc gtaagttata tatcctctta    1020
gggttgttta cgagtcttta a                                              1041
```

<210> SEQ ID NO 14
<211> LENGTH: 346
<212> TYPE: PRT
<213> ORGANISM: Arabidopsis sp

<400> SEQUENCE: 14

```
Met Glu Glu Glu Leu Lys Leu Phe Ile Gln Val Trp Val Ser Ala Ile
 1               5                   10                  15

Ile Ser Val Thr Tyr Cys Tyr Tyr Leu Thr Pro Lys Ile Lys Thr Ser
                20                  25                  30

Leu Leu Arg Leu Leu Ser Val Leu Pro Val Cys Val Leu Phe Leu Ile
            35                  40                  45

Ile Pro Ile Phe Phe Ser Thr Val His Ser Ser Phe Thr Ile Ala Phe
        50                  55                  60

Phe Leu Ser Gly Leu Ala Val Pro Lys Leu Ile Leu Phe Ala Leu Glu
65                  70                  75                  80

Lys Gly Pro Leu Phe Pro Leu Pro Pro Asn Leu Pro His Phe Val Cys
                85                  90                  95

Phe Ala Cys Phe Pro Ile Lys Leu Gln Lys Lys Pro Asn Pro Glu Asn
                100                 105                 110

Thr Asn His Phe Pro Lys Trp Val Phe Ala Leu Lys Val Phe Ile Phe
            115                 120                 125

Gly Ala Leu Leu Leu Gln Ala Tyr His Tyr Lys Gln Phe Leu Ser Thr
        130                 135                 140

Asn Phe Leu Leu Gly Leu Tyr Ala Leu His Ile Tyr Leu Glu Leu Glu
145                 150                 155                 160

Ile Ser Leu Thr Leu Ile Lys Phe Leu Val Ser Ile Thr Leu Gly Cys
                165                 170                 175

Asp Leu Glu Pro Gln Phe Asn Glu Pro Tyr Leu Ala Thr Ser Leu His
            180                 185                 190

Asp Phe Trp Gly His Arg Trp Asn Leu Met Val Ser Lys Ile Leu Trp
        195                 200                 205

Leu Ala Val Tyr Asn Pro Ile Arg Gln Trp Arg Ala Lys Ser Ser Glu
    210                 215                 220

Trp Asp Arg Phe Phe Ala Ile Phe Ala Thr Phe Leu Val Ser Gly Val
225                 230                 235                 240

Ala His Glu Ile Leu Tyr Phe Tyr Leu Thr Arg Glu Lys Pro Thr Trp
                245                 250                 255

Glu Val Thr Trp Phe Phe Val Leu His Gly Phe Cys Met Ala Ala Glu
```

-continued

```
                260                 265                 270
Val Ala Leu Lys Arg Lys Thr Lys Leu Val Gln Arg Trp Pro Val Asn
            275                 280                 285

Pro Ala Val Ser Arg Leu Leu Thr Val Gly Phe Val Phe Val Thr Gly
        290                 295                 300

Val Trp Leu Phe Ser Pro Gln Pro Ile Arg His Gly Leu Met Glu Arg
305                 310                 315                 320

Phe Ile Asn Glu Asp Leu Phe Leu Ile Asp Phe Asn Arg Lys Leu
                325                 330                 335

Tyr Ile Leu Leu Gly Leu Phe Thr Ser Leu
            340                 345
```

<210> SEQ ID NO 15
<211> LENGTH: 1020
<212> TYPE: DNA
<213> ORGANISM: Arabidopsis sp

<400> SEQUENCE: 15

```
atggaggaag aaatcaagag cttgatcaat gtagggtttt taacaattat ctcagtatct     60
tactgctact gcttaccacc aagaatcaaa tctggtgttc ttcgattact ctctattttt    120
ccggtctgtg ttttgttagt tgttcttcct ctgttcttct ccttttcaat tttcacttcc    180
accacagcgt ttttcttatc agctattgcc aattcaagac tcatcctctt ttcctttgat    240
caaggtcctc ttttttccact accttcaaat ctattcagat ttacctgctt tacttgcttc    300
ccaatccagc gtcaacaaaa ccctaaatct caagatcatt tgtccacgta tgttttccc     360
gttaaaattg caatctttgt tgtgttgtta tatgtgcata cgacataca aaaccttcct     420
cgtactttc tattgtgtct ccatccactg tatgtatatt tgttacttga attctctta     480
acgctcctta gaattctaat gactatcatt cttggttgtg acctagagcc acattttcac    540
gaaccatact tagccacatc tcttcaagac ttttggggtc gcaggtggaa cctcatagtc    600
tcggcaagtc ttcgggcaat cgtctacact cctgtgcggc gtgtctgcca acgagtaatg    660
agctctgatt atgcaatgtt gattggtgtt tttgcgacgt tgtaacctc tggtgtggct    720
catgaagtgg ttttcttta taaaccgt gcgatgccta caggggaagt cgctttattc    780
tttctcttac atggagtttg cacggtggcg aagtggcag cgaagaggac ggcgtttgta    840
cggaggtggc cggtgagacc agtcgtatct ggatgttca cgatagcgtt tgtaaatgtg    900
accgctggtt ggctgttttt tcctcagttg attcggaaca acctggggga gagatgctcc    960
aatgaaatct ccttgctcat tgatttcttc agaagcaagt tatttattt tccccagtga   1020
```

<210> SEQ ID NO 16
<211> LENGTH: 339
<212> TYPE: PRT
<213> ORGANISM: Arabidopsis sp

<400> SEQUENCE: 16

```
Met Glu Glu Glu Ile Lys Ser Leu Ile Asn Val Gly Phe Leu Thr Ile
1               5                   10                  15

Ile Ser Val Ser Tyr Cys Tyr Cys Leu Pro Pro Arg Ile Lys Ser Gly
            20                  25                  30

Val Leu Arg Leu Leu Ser Ile Phe Pro Val Cys Val Leu Leu Val Val
        35                  40                  45

Leu Pro Leu Phe Phe Ser Phe Ser Ile Phe Thr Ser Thr Thr Ala Phe
    50                  55                  60
```

```
Phe Leu Ser Ala Ile Ala Asn Ser Arg Leu Ile Leu Phe Ser Phe Asp
 65                  70                  75                  80

Gln Gly Pro Leu Phe Pro Leu Pro Ser Asn Leu Phe Arg Phe Thr Cys
                 85                  90                  95

Phe Thr Cys Phe Pro Ile Gln Arg Gln Gln Asn Pro Lys Ser Gln Asp
            100                 105                 110

His Leu Ser Thr Tyr Val Phe Pro Val Lys Ile Ala Ile Phe Val Val
        115                 120                 125

Leu Leu Tyr Val His Asn Asp Ile Gln Asn Leu Pro Arg Thr Phe Leu
    130                 135                 140

Leu Cys Leu His Pro Leu Tyr Val Tyr Leu Leu Glu Ile Leu Leu
145                 150                 155                 160

Thr Leu Leu Arg Ile Leu Met Thr Ile Ile Leu Gly Cys Asp Leu Glu
                165                 170                 175

Pro His Phe His Glu Pro Tyr Leu Ala Thr Ser Leu Gln Asp Phe Trp
            180                 185                 190

Gly Arg Arg Trp Asn Leu Ile Val Ser Ala Ser Leu Arg Ala Ile Val
        195                 200                 205

Tyr Thr Pro Val Arg Arg Val Cys Gln Arg Val Met Ser Ser Asp Tyr
    210                 215                 220

Ala Met Leu Ile Gly Val Phe Ala Thr Phe Val Thr Ser Gly Val Ala
225                 230                 235                 240

His Glu Val Val Phe Phe Tyr Ile Thr Arg Ala Met Pro Thr Gly Glu
                245                 250                 255

Val Ala Leu Phe Phe Leu Leu His Gly Val Cys Thr Val Ala Glu Val
            260                 265                 270

Ala Ala Lys Arg Thr Ala Phe Val Arg Arg Trp Pro Val Arg Pro Val
        275                 280                 285

Val Ser Trp Met Phe Thr Ile Ala Phe Val Asn Val Thr Ala Gly Trp
    290                 295                 300

Leu Phe Phe Pro Gln Leu Ile Arg Asn Asn Leu Gly Glu Arg Cys Ser
305                 310                 315                 320

Asn Glu Ile Ser Leu Leu Ile Asp Phe Phe Arg Ser Lys Leu Phe Tyr
                325                 330                 335

Phe Pro Gln

<210> SEQ ID NO 17
<211> LENGTH: 708
<212> TYPE: DNA
<213> ORGANISM: Simmondsia chinensis
<220> FEATURE:
<221> NAME/KEY: misc_feature
<222> LOCATION: (1)...(708)
<223> OTHER INFORMATION: n = A,T,C or G

<400> SEQUENCE: 17
gatgacccaw snaaygacca tgagaaaaac aagagaactc tgagttttga gtggcgtaaa      60
gttgttcttt tgttgctaa gttggtgttt tttgcgggta ttttaaagat ttatgagttt     120
agaaaagatt tgcctcattt tgtgatctcg gtgctttact gttttcactt ctatctcggg    180
acggagatca ccttagcagc aagcgcagtc atagctcgag ccacgctagg gttagaccta    240 taccccagt tcaacgagcc atacttagcc acctcgctgc aagacttctg ggggcgcagg     300 tggaaccta tggtgtcaga catcttgggg ttgacaacat accagcctgt ccggcgtgtc     360
ctctcgaggt gggtcaggct gcggtgggag gtcgccggcg caatgttggt ggcgttcacg    420
```

```
gtgtcggggc taatgcatga agtgtttttc ttntacttaa ctcgcgcgag gccctcgtgg      480
gaggtgacgg ggttctttgt bttgcatggg gtttgcacag ccgtggagat ggtggtgaag      540
aaggcggttt caggcaaggt gcggctgcgc cgggaggtgt caggggcgct gacggtgggg      600
ttcgtgatgg tgactggagg gtggttgttt ttgccgcagc tggtgaggca tggggtagat      660
ttgaagacca ttgatgagta tcctgtcatg ttyaaytaya cccagaaa                   708
```

<210> SEQ ID NO 18
<211> LENGTH: 1335
<212> TYPE: DNA
<213> ORGANISM: Simmondsia chinensis

<400> SEQUENCE: 18

```
gtctccatta caatggaggt ggagaaggag ctaaagacct tctcagaggt atggatctcc       60
gccatagccg ccgcctgcta ctgccgcttc gtccccgccg ttgcccctca cggcggcgct      120
ctccgcctcc tcctcctcct ccccgtcgtc ctcctcttca ttttcctccc cctccgcctc      180
tcctccttcc acctcggcgg gcccaccgcc ttgtatctcg tctggcttgc caacttcaag      240
ctccttctct tcgcctttca tcttggcccc ttatctaacc cctctctctc tctccttcac      300
ttcatctcca ccaccctcct ccccatcaag ttcagagatg acccatctaa tgatcatgag      360
aaaaacaaga gaactctgag ttttgagtgg cgtaaagttg ttcttttttgt tgctaagttg      420 gtgttttttg cgggtatttt aaagatttat gagtttagaa aagatttgcc tcattttgtg      480
atctcggtgc tttactgttt tcacttctat ctcgggacgg agatcacctt agcagcaagc      540
gcagtcatag ctcgagccac gctagggtta gacctatacc cccagttcaa cgagccatac      600
ttagccacct cgctgcaaga cttctgggg cgcaggtgga acctcatggt gtcagacatc      660
ttggggttga caacatacca gcctgtccgg cgtgtcctct cgaggtgggt caggctgcgg      720
tgggaggtcg ccggcgcaat gttggtggcg ttcacggtgt cggggctaat gcatgaagtg      780 ttttcttct acttaactcg cgcgaggccc tcgtgggagg tgacggggtt ctttgtgttg      840 catgggggttt gcacagccgt ggagatggtg gtgaagaagg cggtttcagg caaggtgcgg      900
ctgcgccggg aggtgtcagg ggcgctgacg gtggggttcg tgatggtgac tggagggtgg      960 ttgttttttgc cgcagctggt gaggcatggg gtagatttga agaccattga tgagtatcct     1020
gtcatgttta attatactca aagaaattg atgggtttgt tggggtggtg atgaatgatg     1080
agatgatgat catgcatctt ctttttcgga gatcggttgt acgtcacgag agaacccat     1140 gaaaaatgca gatcaracgg caagacaggt cgggaaaaaa aatgatcaa ttttttcctta     1200 agtagccggc ctgccaccct gtccgattgt ggcattttg tggtcactttt ttcatatcgt     1260 gtagtatttt tggttttttg tttttaatgt tttctatgaa ttttgaataa tttgtgcttc     1320
atgaaaattt ttttt                                                     1335
```

<210> SEQ ID NO 19
<211> LENGTH: 436
<212> TYPE: DNA
<213> ORGANISM: Glycine sp

<400> SEQUENCE: 19

```
aaacccgtga ggtcattatt aatgtccaag accgtgttgg gcccccagtg ggcctcggtg       60
tccggagtca tgggcaactt tcttggtgtc tggtctaatg cacgagctga ttttctacta      120
cgtcacacgt gttagtccca cgtgggaggt cacgtgcttc ttttttgctcc atggggtgtg      180 tgccgttgcg ragtttggtg cggtraagtg gttgggcgct aaatggagac tgcattgggc      240
```

```
cttgtgtggg cccattacgg tggcgtttgt gatagtcacc gccgcgtggc tcttctttcc    300
accgttgatg catgatggca cagatgagag aaccatcaag gagttcaacg atgtagttga    360
gtgtgtgatg ggaaaatttt actagtccca tttcattgaa cattacctgt ttcccttatg    420
tcaaattttc cattat                                                    436
```

<210> SEQ ID NO 20
<211> LENGTH: 13
<212> TYPE: PRT
<213> ORGANISM: Unknown
<220> FEATURE:
<223> OTHER INFORMATION: WSpep-29 peptide

<400> SEQUENCE: 20

Phe Val Pro Ala Val Ala Pro His Gly Gly Ala Leu Arg
 1               5                  10

<210> SEQ ID NO 21
<211> LENGTH: 14
<212> TYPE: PRT
<213> ORGANISM: Unknown
<220> FEATURE:
<223> OTHER INFORMATION: WSpep-33 peptide

<400> SEQUENCE: 21

Thr Ile Asp Glu Tyr Pro Val Met Phe Asn Tyr Thr Gln Lys
 1               5                  10

<210> SEQ ID NO 22
<211> LENGTH: 39
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(39)
<223> OTHER INFORMATION: n = A,T,C or G

<400> SEQUENCE: 22
ttygtnccng cngtngcncc ncayggnggn gcnytnmgn                            39

<210> SEQ ID NO 23
<211> LENGTH: 39
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(39)
<223> OTHER INFORMATION: n = A,T,C or G

<400> SEQUENCE: 23
ncknarngcn ccnccrtgng gngcnacngc nggnacraa                            39

<210> SEQ ID NO 24
<211> LENGTH: 42
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(42)
<223> OTHER INFORMATION: n = A,T,C or G

```
<400> SEQUENCE: 24
acnathgayg artayccngt natgttyaay tayacncara ar                    42

<210> SEQ ID NO 25
<211> LENGTH: 42
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(42)
<223> OTHER INFORMATION: n = A,T,C or G

<400> SEQUENCE: 25
yttytgngtr tarttraaca tnacnggrta ytcrtcdatn gt                    42

<210> SEQ ID NO 26
<211> LENGTH: 9
<212> TYPE: PRT
<213> ORGANISM: unknown
<220> FEATURE:
<223> OTHER INFORMATION: WSpep-14 peptide

<400> SEQUENCE: 26

Phe Arg Asp Asp Pro Ser Asn Asp His
 1               5

<210> SEQ ID NO 27
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(27)
<223> OTHER INFORMATION: n = A,T,C or G

<400> SEQUENCE: 27
ttymgngayg ayccnwsnaa ygaycay                                     27

<210> SEQ ID NO 28
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(27)
<223> OTHER INFORMATION: n = A,T,C or G

<400> SEQUENCE: 28
rtgrtcrttn swnggrtcrt cnckraa                                     27

<210> SEQ ID NO 29
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(17)
<223> OTHER INFORMATION: n = A,T,C or G

<400> SEQUENCE: 29
```
ttygtnccng cngtngc                                                    17

<210> SEQ ID NO 30
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(17)
<223> OTHER INFORMATION: n = A,T,C or G

<400> SEQUENCE: 30
gcnccncayg gnggngc                                                    17

<210> SEQ ID NO 31
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(17)
<223> OTHER INFORMATION: n = A,T,C or G

<400> SEQUENCE: 31
gcnccnccrt gnggngc                                                    17

<210> SEQ ID NO 32
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(17)
<223> OTHER INFORMATION: n = A,T,C or G

<400> SEQUENCE: 32
gcnacngcng gnacraa                                                    17

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(20)
<223> OTHER INFORMATION: n = A,T,C or G

<400> SEQUENCE: 33
acnathgayg artayccngt                                                 20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(20)
<223> OTHER INFORMATION: n = A,T,C or G

<400> SEQUENCE: 34
ccngtnatgt tyaaytayac                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(20)
<223> OTHER INFORMATION: n = A,T,C or G

<400> SEQUENCE: 35
ttytgngtrt arttraacat                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(20)
<223> OTHER INFORMATION: n = A,T,C or G

<400> SEQUENCE: 36
aacatnacng grtaytcrtc                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(20)
<223> OTHER INFORMATION: n = A,T,C or G

<400> SEQUENCE: 37
gaygayccnw snaaygayca                                              20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(20)
<223> OTHER INFORMATION: n = A,T,C or G

<400> SEQUENCE: 38
tgrtcrttns wnggrtcrtc                                              20

<210> SEQ ID NO 39
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 39
gatttgcctc attttgtgat ctcggtgct                                    29

<210> SEQ ID NO 40
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 40
gacctatacc cccagttcaa cgagccatac                              30

<210> SEQ ID NO 41
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 41
aacaaccacc ctccagtcac catcacgaac                              30

<210> SEQ ID NO 42
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 42
ttgcctgaaa ccgccttctt caccaccatc                              30

<210> SEQ ID NO 43
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 43
aagatgtctg acaccatgag gttccacctg                              30

<210> SEQ ID NO 44
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 44
ggatccgtcg acacaatgga ggtggagaag gagctaaag                    39

<210> SEQ ID NO 45
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 45
gcatgcagat ctcaccaccc caacaaaccc atc                          33

<210> SEQ ID NO 46
<211> LENGTH: 9
<212> TYPE: PRT
<213> ORGANISM: Artificial Sequence
<220> FEATURE:
<223> OTHER INFORMATION: Conserved peptide

```
<220> FEATURE:
<221> NAME/KEY: misc_feature
<222> LOCATION: (1)...(9)
<223> OTHER INFORMATION: Xaa = Any Amino Acid

<400> SEQUENCE: 46

Leu Xaa Leu Phe Xaa Xaa Xaa Xaa Xaa
 1               5

<210> SEQ ID NO 47
<211> LENGTH: 19
<212> TYPE: PRT
<213> ORGANISM: Artificial Sequence
<220> FEATURE:
<223> OTHER INFORMATION: Conserved peptide
<220> FEATURE:
<221> NAME/KEY: misc_feature
<222> LOCATION: (1)...(19)
<223> OTHER INFORMATION: Xaa = Any Amino Acid

<400> SEQUENCE: 47

Pro Tyr Leu Xaa Thr Ser Leu Xaa Xaa Phe Trp Xaa Xaa Arg Trp Asn
 1               5                  10                  15

Leu Xaa Val

<210> SEQ ID NO 48
<211> LENGTH: 17
<212> TYPE: PRT
<213> ORGANISM: Artificial Sequence
<220> FEATURE:
<223> OTHER INFORMATION: Conserved peptide
<220> FEATURE:
<221> NAME/KEY: misc_feature
<222> LOCATION: (1)...(17)
<223> OTHER INFORMATION: Xaa = Any Amino Acid

<400> SEQUENCE: 48

Phe Xaa Xaa Ser Gly Xaa Xaa His Glu Xaa Xaa Xaa Phe Tyr Xaa Xaa
 1               5                  10                  15

Arg

<210> SEQ ID NO 49
<211> LENGTH: 13
<212> TYPE: PRT
<213> ORGANISM: Artificial Sequence
<220> FEATURE:
<223> OTHER INFORMATION: Conserved peptide
<220> FEATURE:
<221> NAME/KEY: misc_feature
<222> LOCATION: (1)...(13)
<223> OTHER INFORMATION: Xaa = Any Amino Acid

<400> SEQUENCE: 49

Pro Xaa Xaa Glu Val Xaa Xaa Phe Phe Xaa Leu His Gly
 1               5                  10

<210> SEQ ID NO 50
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 50
cgcgatttaa atggcgcgcc ctgcaggcgg ccgcctgcag ggcgcgccat ttaaat        56

<210> SEQ ID NO 51
```

```
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 51
tcgaggatcc gcggccgcaa gcttcctgca gg                                    32

<210> SEQ ID NO 52
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 52
tcgacctgca ggaagcttgc ggccgcggat cc                                    32

<210> SEQ ID NO 53
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 53
tcgacctgca ggaagcttgc ggccgcggat cc                                    32

<210> SEQ ID NO 54
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 54
tcgaggatcc gcggccgcaa gcttcctgca gg                                    32

<210> SEQ ID NO 55
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 55
tcgaggatcc gcggccgcaa gcttcctgca ggagct                                36

<210> SEQ ID NO 56
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 56
cctgcaggaa gcttgcggcc gcggatcc                                         28

<210> SEQ ID NO 57
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 57
```

-continued

```
tcgacctgca ggaagcttgc ggccgcggat ccagct                                36

<210> SEQ ID NO 58
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 58
ggatccgcgg ccgcaagctt cctgcagg                                         28

<210> SEQ ID NO 59
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 59
ggatccgcgg ccgcattatg aaacagttag caaccaacag a                          41

<210> SEQ ID NO 60
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 60
ggatcccctg caggttacat taaaatacag acaacgtgcc                            40

<210> SEQ ID NO 61
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 61
ttgcctgaaa ccgccttctt caccaccatc                                       30
```